US012668803B2

(12) United States Patent
Lee et al.

(10) Patent No.: US 12,668,803 B2
(45) Date of Patent: Jun. 30, 2026

(54) GLYPICAN-3-SPECIFIC MODIFIED APTAMER AND USE THEREOF

(71) Applicant: APTAMER SCIENCES INC., Gyeonggi-do (KR)

(72) Inventors: Jo Woon Yi Lee, Gyeonggi-do (KR); Youndong Kim, Gyeonggi-do (KR); Da Som Lee, Seoul (KR); Jeong Kyun Lee, Gyeonggi-do (KR); Daekyun Lee, Gyeonggi-do (KR); So Ryong Lim, Gyeonggi-do (KR)

(73) Assignee: APTAMER SCIENCES INC., Gyeonggi-do (KR)

( * ) Notice: Subject to any disclaimer, the term of this patent is extended or adjusted under 35 U.S.C. 154(b) by 1092 days.

(21) Appl. No.: 17/774,601

(22) PCT Filed: Nov. 6, 2020

(86) PCT No.: PCT/KR2020/015536
§ 371 (c)(1),
(2) Date: May 5, 2022

(87) PCT Pub. No.: WO2021/091319
PCT Pub. Date: May 14, 2021

(65) Prior Publication Data
US 2023/0127087 A1 Apr. 27, 2023

(30) Foreign Application Priority Data

Nov. 8, 2019 (KR) ........................ 10-2019-0142363

(51) Int. Cl.
| | |
|---|---|
| *C12N 15/115* | (2010.01) |
| *A61K 31/282* | (2006.01) |
| *A61K 31/337* | (2006.01) |
| *A61K 31/404* | (2006.01) |
| *A61K 31/4545* | (2006.01) |
| *A61K 31/475* | (2006.01) |
| *A61K 31/519* | (2006.01) |
| *A61K 31/675* | (2006.01) |
| *A61K 31/704* | (2006.01) |
| *A61K 31/7068* | (2006.01) |
| *A61K 33/243* | (2019.01) |
| *A61P 1/16* | (2006.01) |
| *A61P 35/00* | (2006.01) |
| *C12N 15/11* | (2006.01) |

(52) U.S. Cl.
CPC .......... *C12N 15/115* (2013.01); *A61K 31/282* (2013.01); *A61K 31/337* (2013.01); *A61K 31/404* (2013.01); *A61K 31/4545* (2013.01); *A61K 31/475* (2013.01); *A61K 31/519* (2013.01); *A61K 31/675* (2013.01); *A61K 31/704* (2013.01); *A61K 31/7068* (2013.01); *A61K 33/243* (2019.01); *A61P 1/16* (2018.01); *A61P 35/00* (2018.01); *C12N 15/111*

(2013.01); *C12N 2310/16* (2013.01); *C12N 2310/335* (2013.01); *C12N 2310/531* (2013.01)

(58) Field of Classification Search
CPC .............. C12N 15/115; C12N 2310/16; A61K 31/282; A61P 35/00
See application file for complete search history.

(56) References Cited

U.S. PATENT DOCUMENTS

| | | | |
|---|---|---|---|
| 2008/0138827 A1 | 6/2008 | Watanabe et al. | |
| 2019/0136239 A1* | 5/2019 | Oh ...................... | A61K 31/7088 |

FOREIGN PATENT DOCUMENTS

| | | |
|---|---|---|
| JP | 2011-068682 A | 4/2011 |
| JP | 2017-506074 A | 3/2017 |
| JP | 2017-517260 A | 6/2017 |
| KR | 10-2015-0096384 A | 8/2015 |
| KR | 10-2017-0104398 A | 9/2017 |
| KR | 10-2018-0013082 A | 2/2018 |
| KR | 10-2154683 B1 | 9/2020 |
| WO | 2010/143714 A1 | 12/2010 |
| WO | 2017/173247 A1 | 10/2017 |

OTHER PUBLICATIONS

Park et al. (Pharmaceutics (2020) 20(10), 985: 15 pages; published Oct. 18, 2020). (Year: 2020).*
Park et al. (Mol. Ther. Nucleic Acids (2018) 12:543-553) (Year: 2018).*
Fu et al. (Hepatology (2019) 70(20):563-576) (Year: 2019).*
Jang et al., "Management of viral hepatitis in patients with hepatocellular carcinoma," Journal of the Korean Medical Association, 56(11): 1001-1011 (2013) (see English abstract).
International Search Report issued in corresponding International Patent Application No. PCT/KR2020/015536 dated Mar. 4, 2021.
Written Opinion of the International Searching Authority issued in corresponding International Patent Application No. PCT/KR2020/015536 dated Mar. 4, 2021.
Extended European Search Report issued in the corresponding Application No. 20885612.0, dated Nov. 14, 2023.
Ying Fu et al., Hepatology, John Wiley & Sons, Inc, US, 2019, vol. 70, No. 2, pp. 563-576.
Jun Young Park et al., Molecular Therapy-Nucleic Acids, 2018, vol. 12, pp. 543-553.
Park Jun Young et al., Pharmaceutics, 2020, vol. 12, No. 10, p. 985.

* cited by examiner

*Primary Examiner* — J. E. Angell
(74) *Attorney, Agent, or Firm* — Morgan, Lewis & Bockius LLP

(57) ABSTRACT

Provided are a glypican-3 (GPC3)-specific modified aptamer, and prevention or treatment of hepatoma using the same. The glypican-3-specific modified aptamer of the present invention specifically binds to glypican-3 to be internalized into hepatoma cells, and exhibits anticancer activity through an anticancer agent bound to the aptamer, and therefore, has a selective anticancer effect only for GPC3-expressing hepatoma cells without affecting normal hepatocytes.

11 Claims, 30 Drawing Sheets
Specification includes a Sequence Listing.

[Fig. 1]
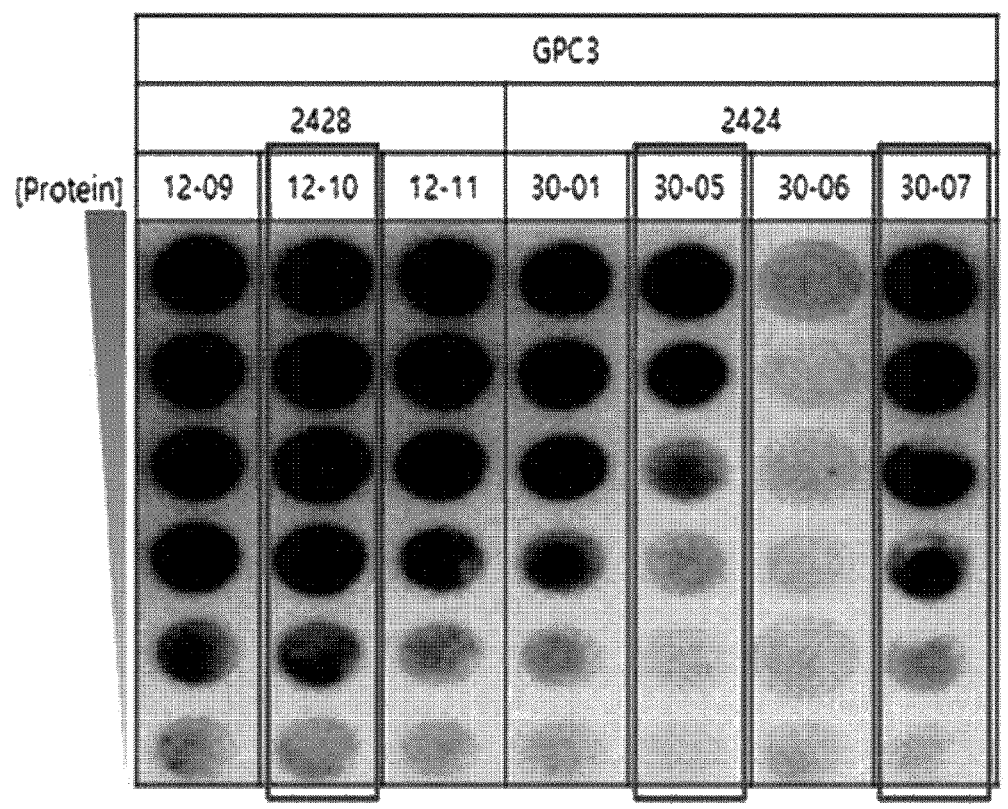
| | GPC3 | | | | | | |
|---|---|---|---|---|---|---|---|
| | 2428 | | | 2424 | | | |
| | 12-09 | 12-10 | 12-11 | 30-01 | 30-05 | 30-06 | 30-07 |
| Bmax | 0.73 | 0.79 | 1.00 | 0.65 | 1.03 | 0.07 | 1.00 |
| Kd(nM) | 1.64 | 1.50 | 4.36 | 4.67 | 71.35 | 29.40 | 5.32 |
| NT # | 58 | 40 | 29 | 73 | 58 | 48 | 57 |

[Fig. 2]
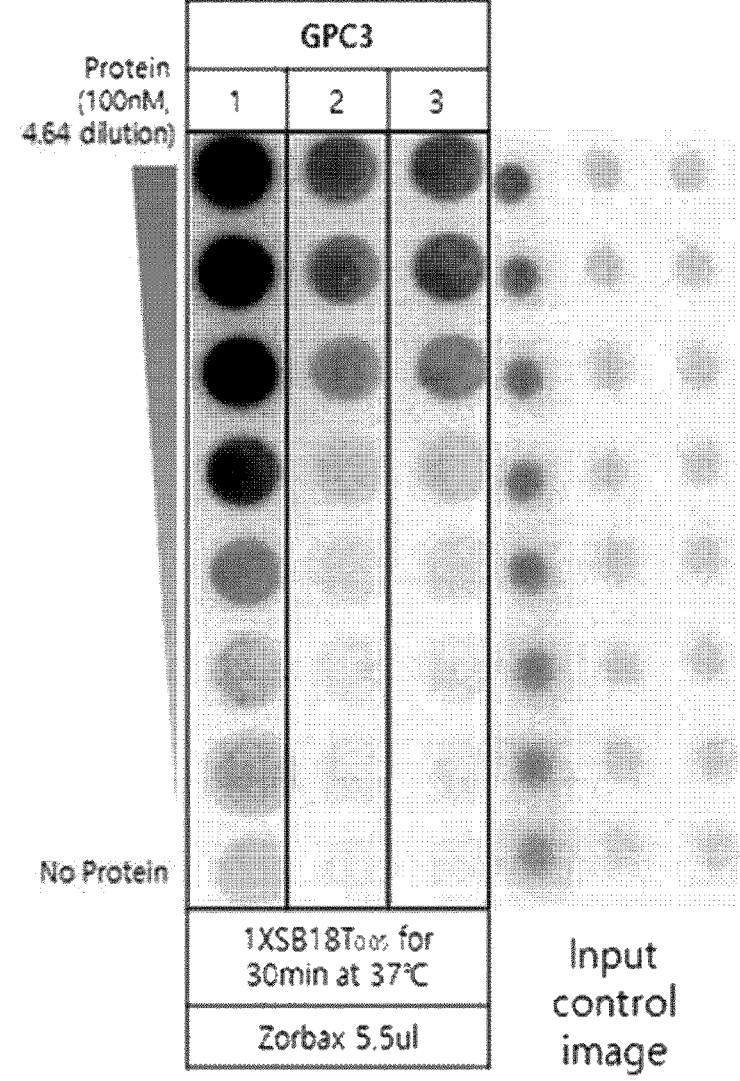
| | GPC3 | | | | Sample name | Seq ID |
|---|---|---|---|---|---|---|
| | 1 | 2 | 3 | 1 | GPC3_40mer | 2428-12-10-idT |
| Bmax | 0.68 | 0.68 | 0.82 | 2 | GPC3_40mer | Cy5-2428-12-10 |
| Kd(nM) | 1.59 | 4.37 | 4.42 | 3 | GPC3_35mer | Cy5-2428-12-12 |

[Fig. 3]
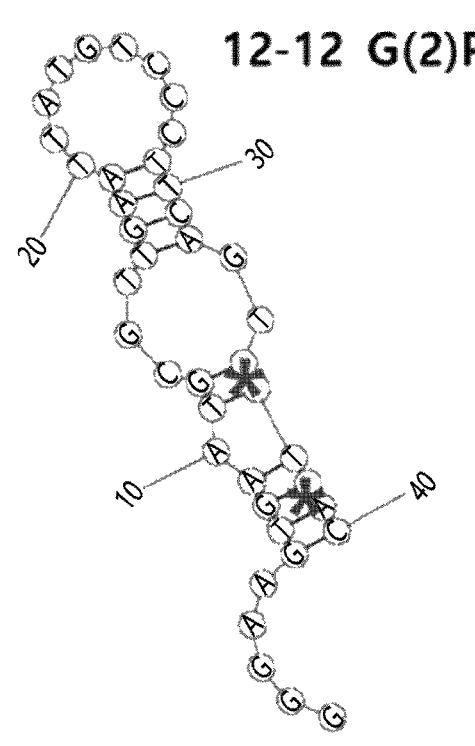
12-12 G(2)P
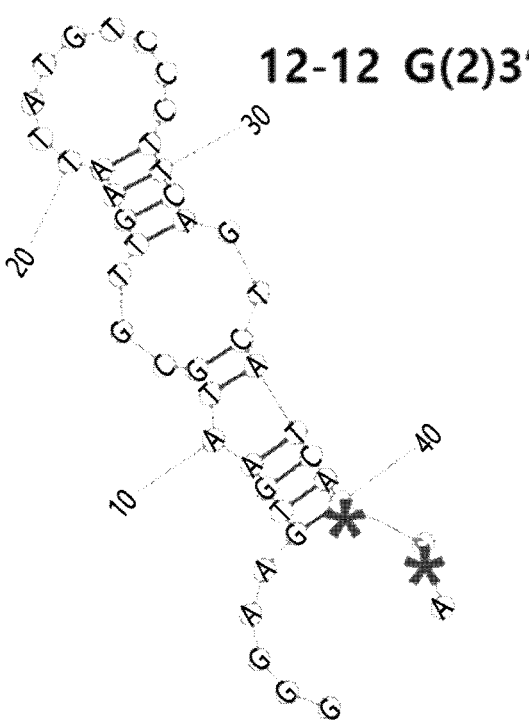
12-12 G(2)3′
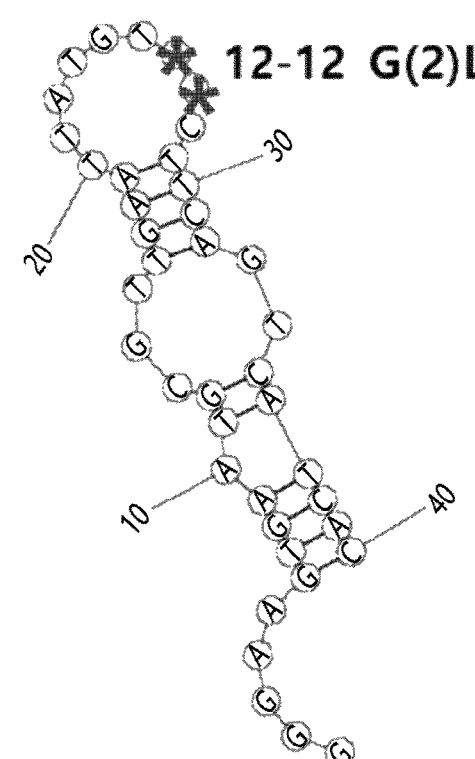
12-12 G(2)L
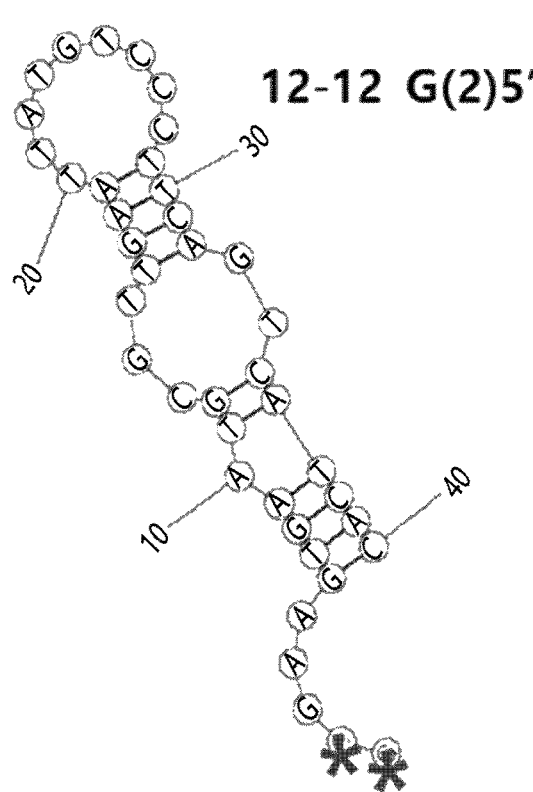
12-12 G(2)5′

[Fig. 4A]
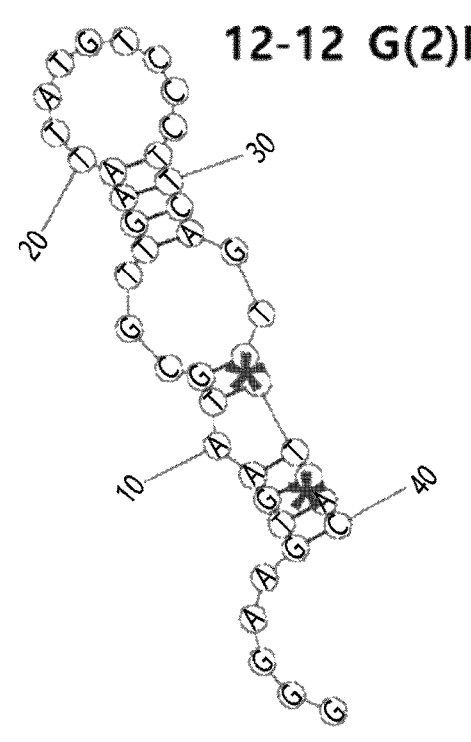
12-12 G(2)P
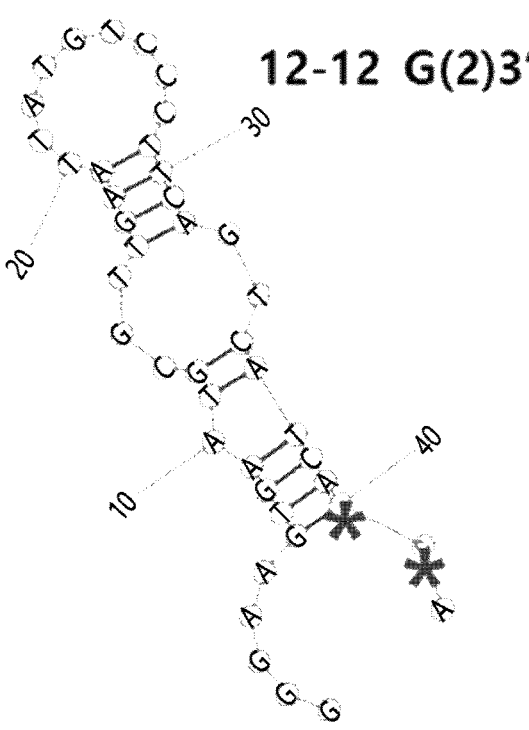
12-12 G(2)3'
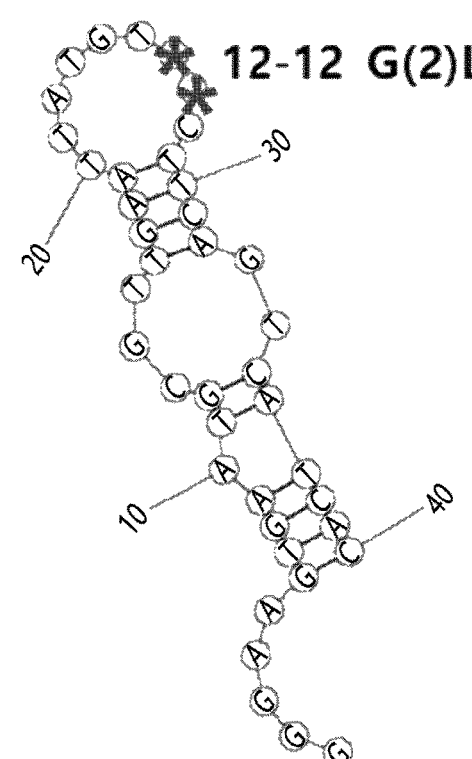
12-12 G(2)L
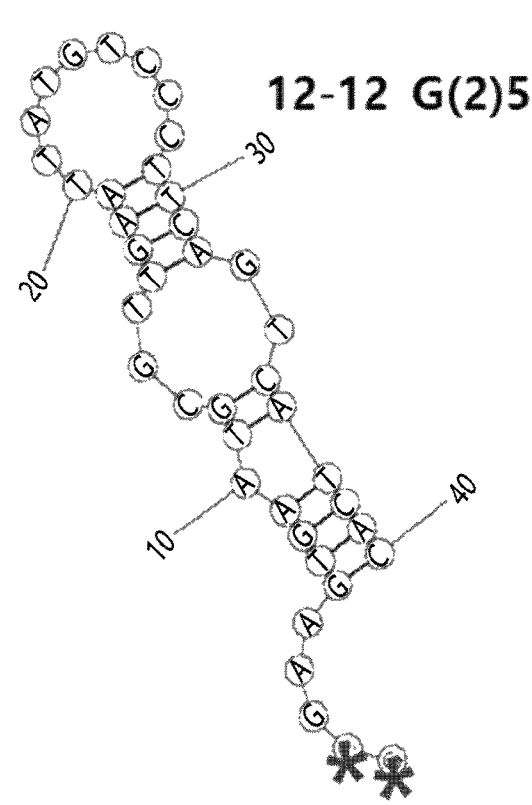
12-12 G(2)5'

[Fig. 4B]
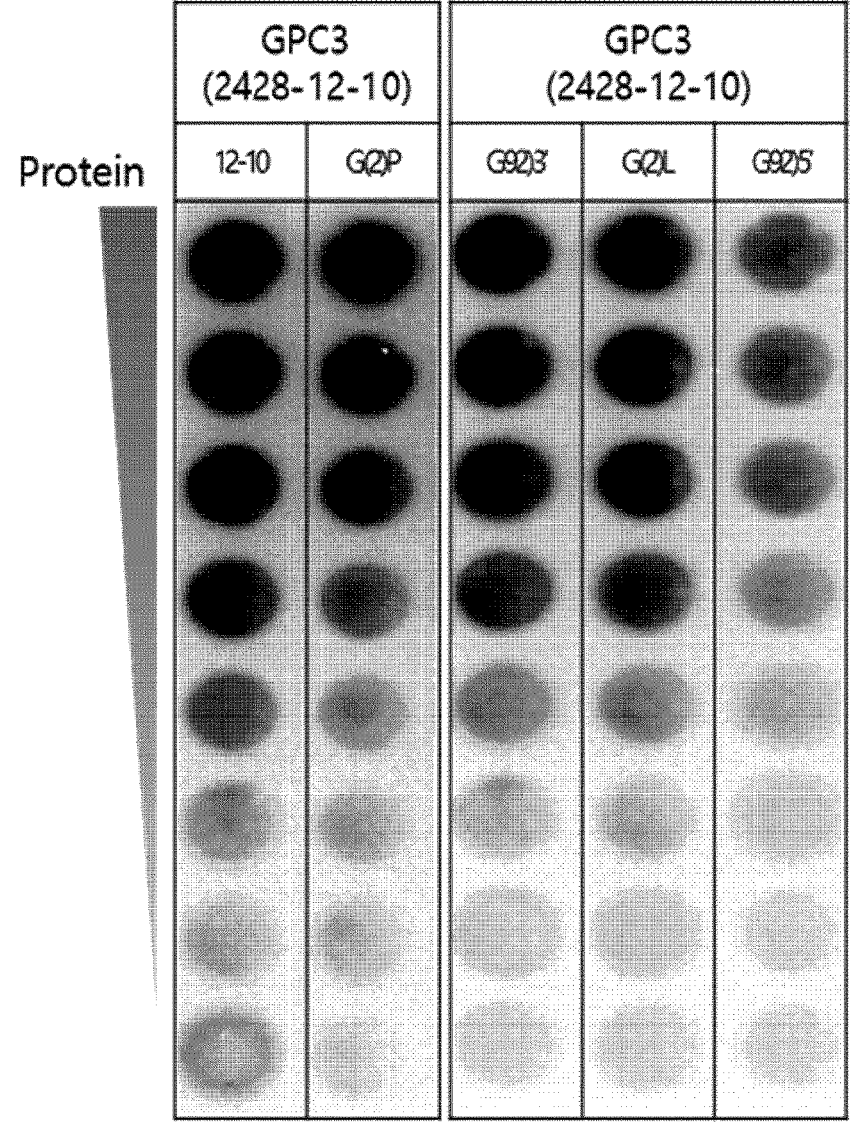
| Avg. | GPC3(2428-12-10) | | GPC3(2428-12-10) | | |
|---|---|---|---|---|---|
| | 12-10 | 12-10 G(2)P | 12-10 G(2)3' | 12-10 G(2)L | 12-10 G(2)5' |
| Bmax | 0.74 | 0.70 | 0.64 | 0.61 | 0.30 |
| Kd(nM) | 1.26 | 4.31 | 1.08 | 0.98 | 1.31 |

[Fig. 5]
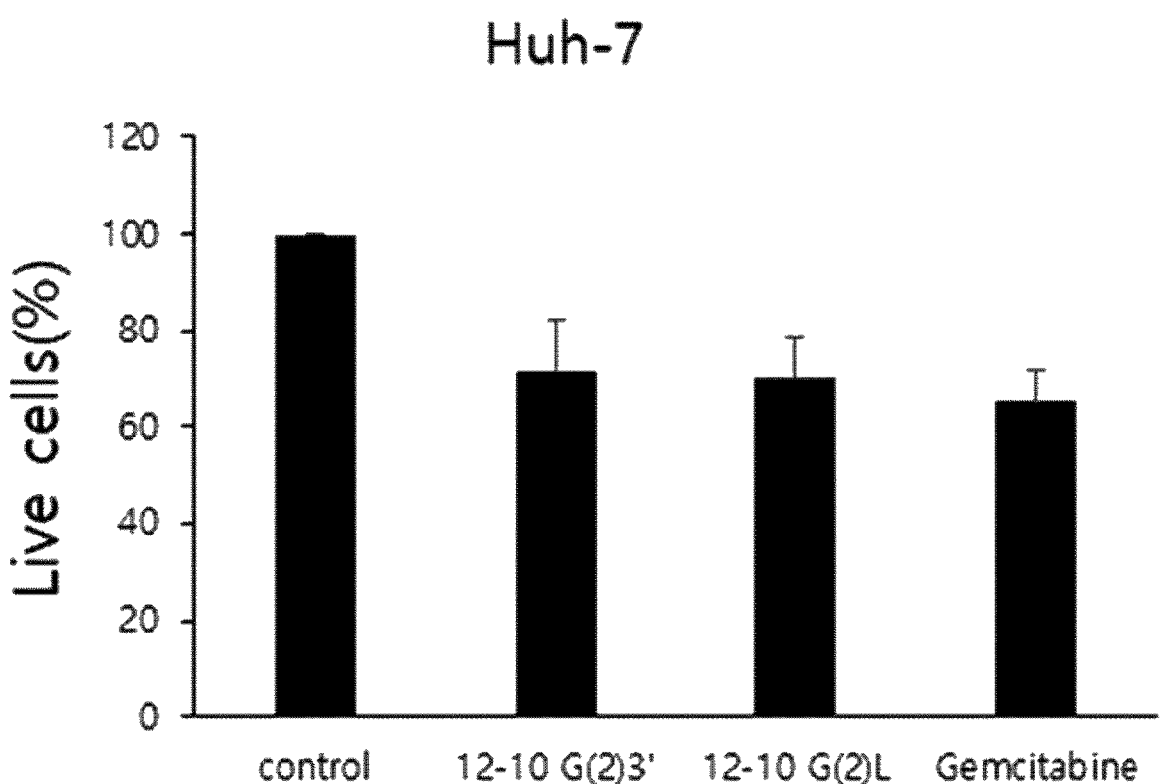

[Fig. 6]
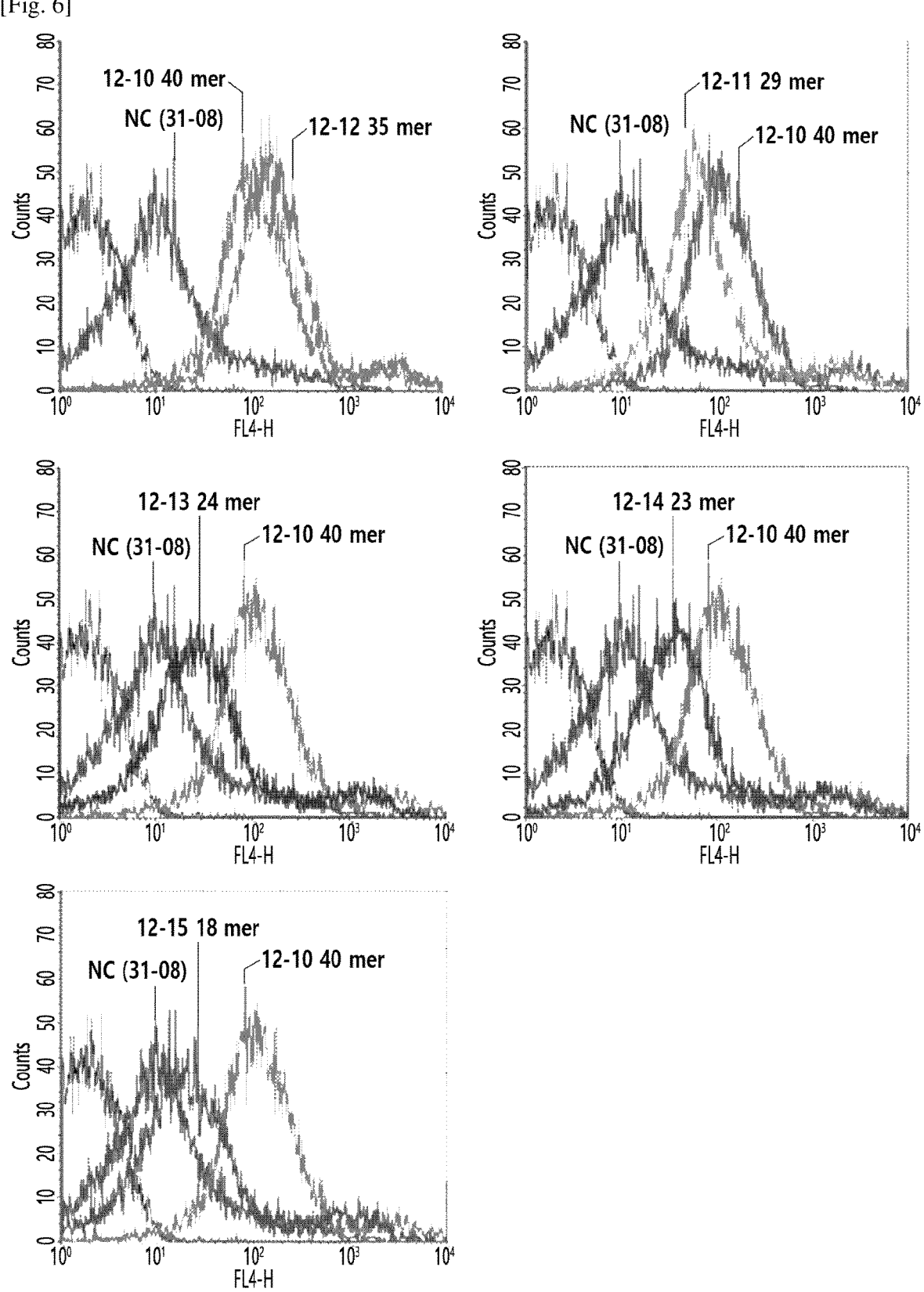

[Fig. 7]
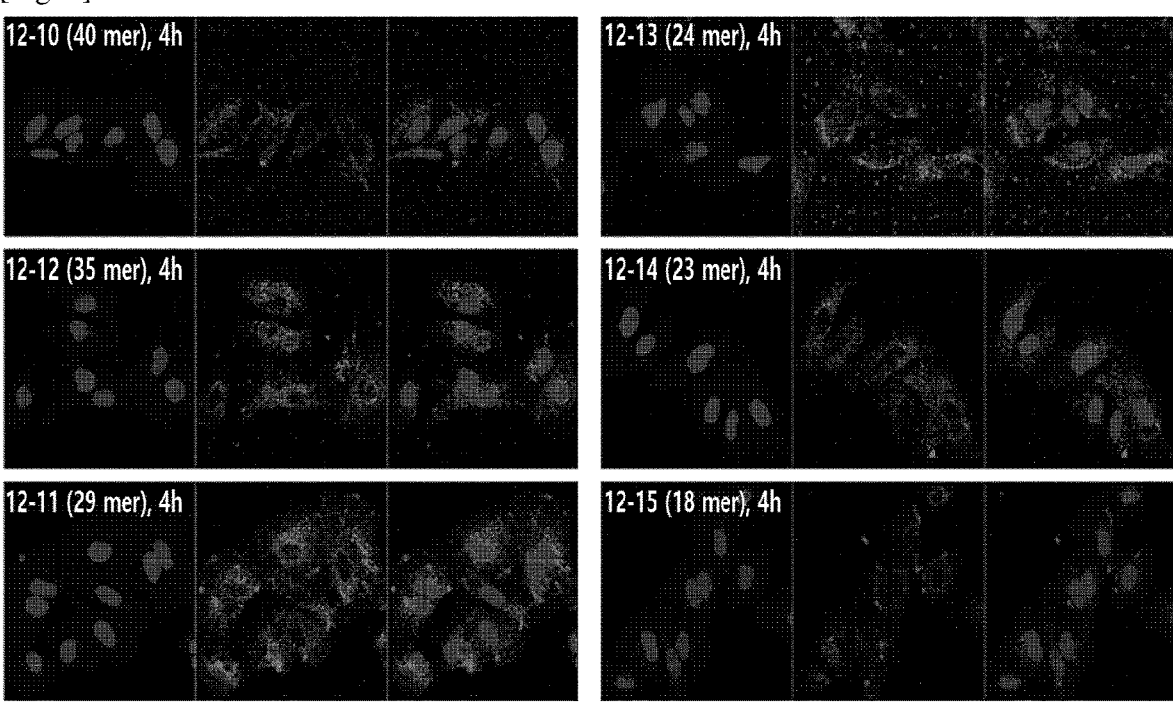

[Fig. 8]
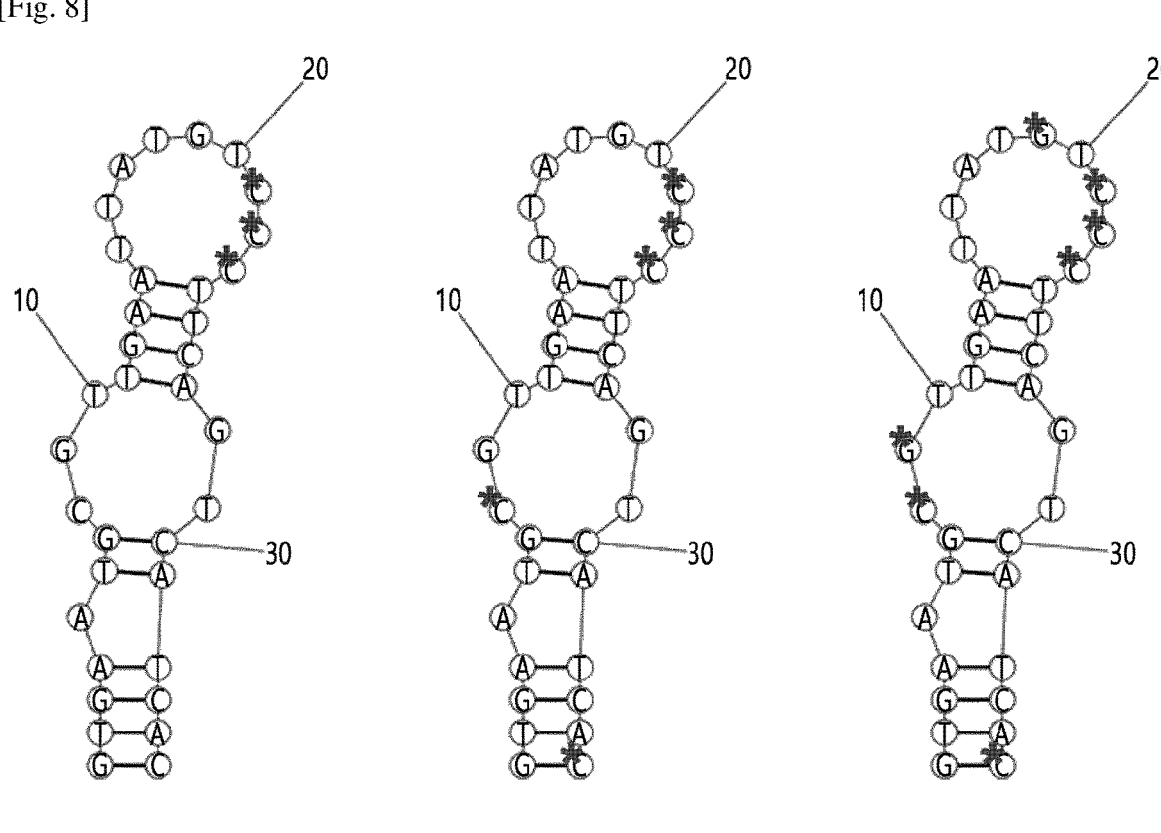
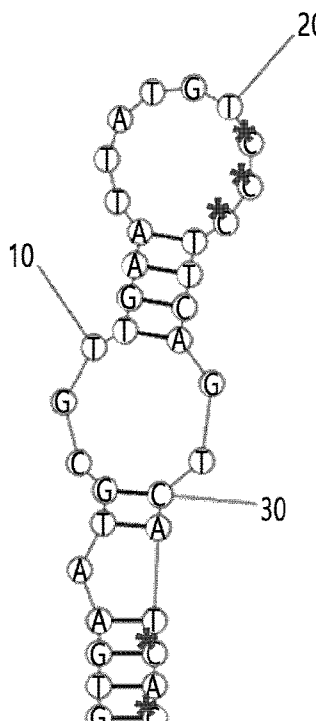

[Fig. 9]
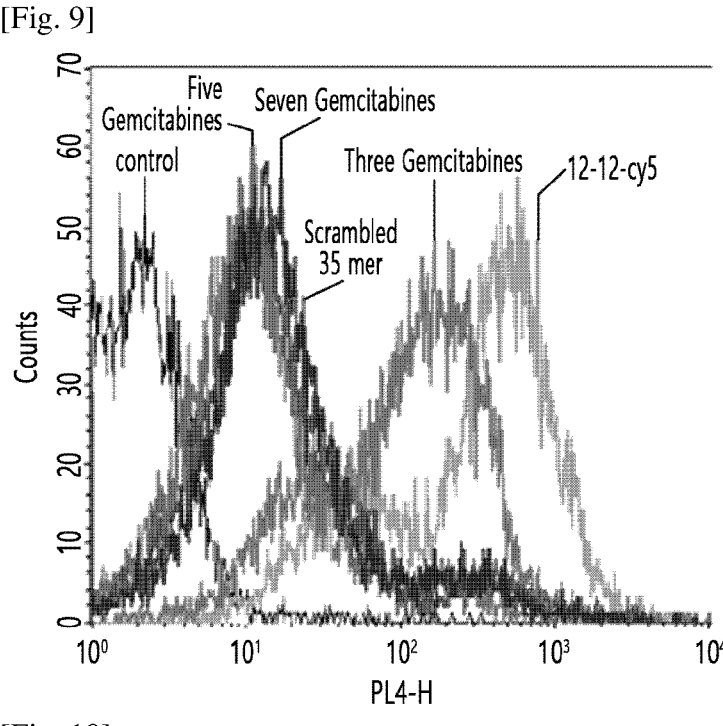
[Fig. 10]
Hep3B, GPC3 Aptamer
1212, SC(35mer), Gemcitabine  4h, x400

[Fig. 11]
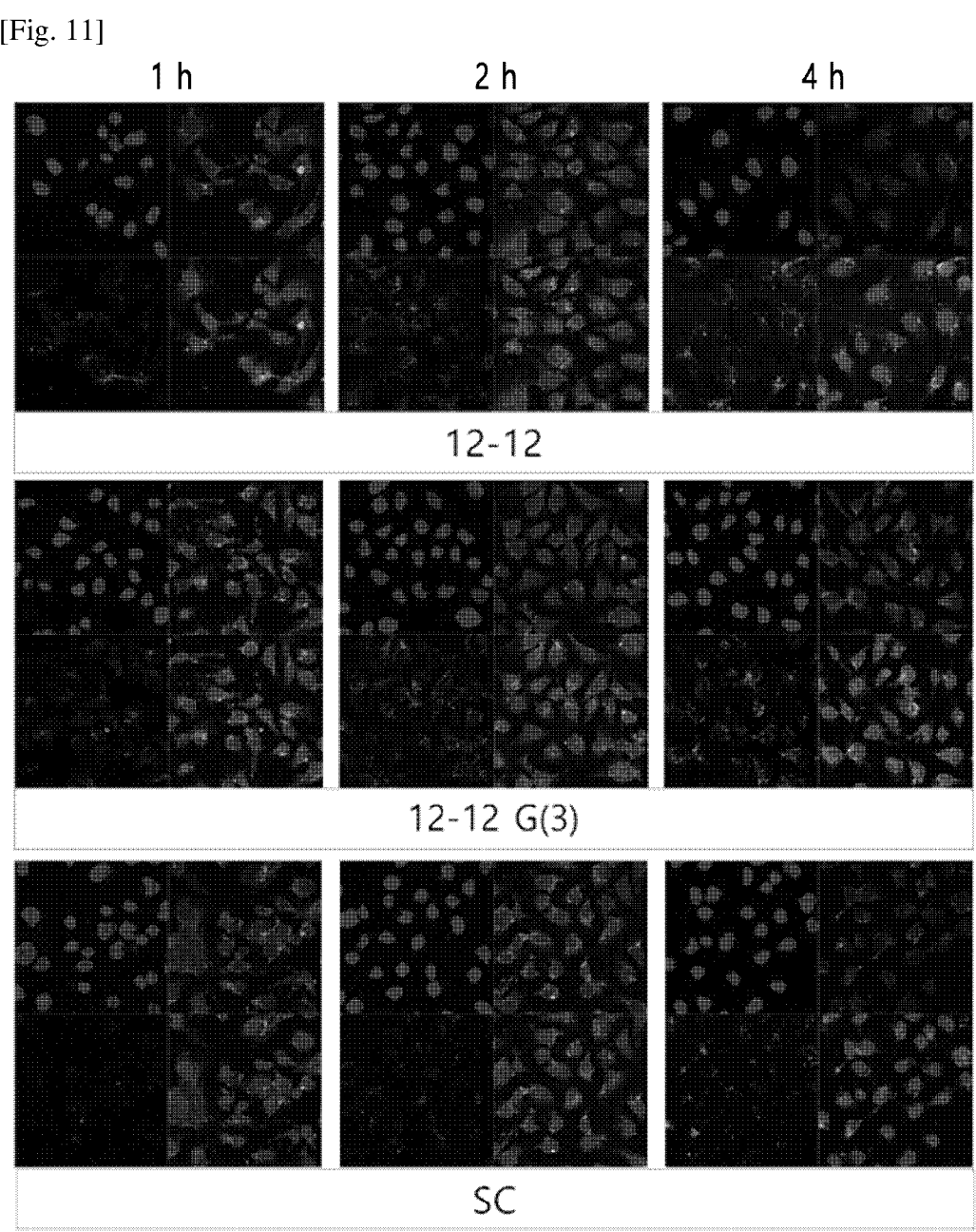
Hep3B, GPC3 Aptamer(25 nM) over time/ lysotracker (150 nM, 37℃, 1h) x400

[Fig. 12]
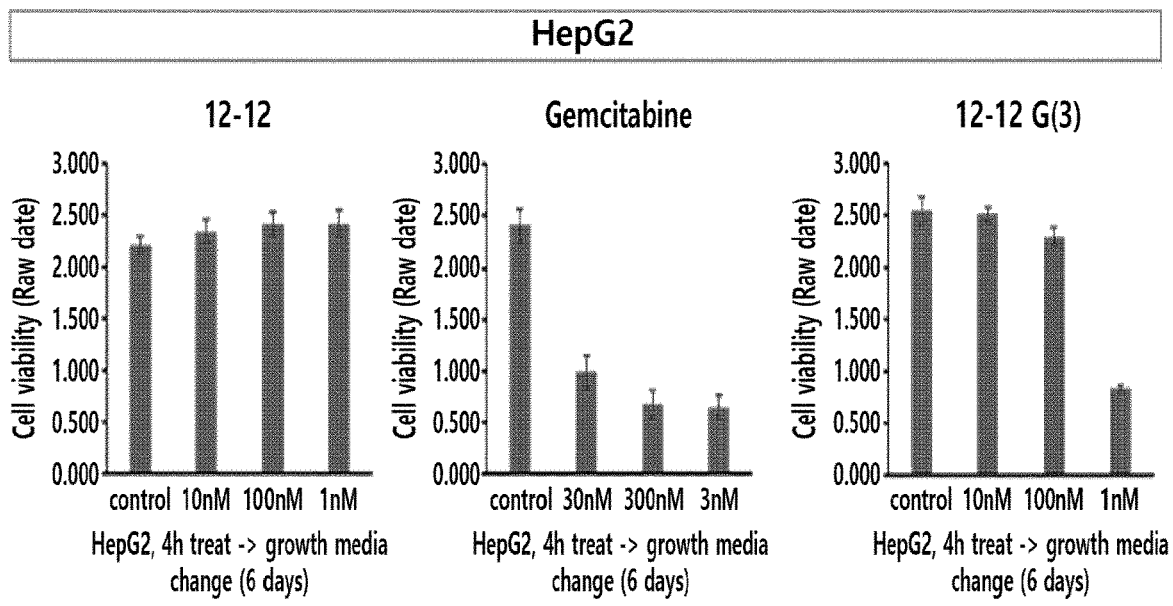
HepG2
Aptamer: GPC3 12-12 10, 100, 1000nM
12-12-G(3)_Granlen 10, 100, 1000nM
Gemcitabine 30, 300, 3000nM
Serum free: 1h aptamer treat -> growth media change 6 days incubation
Heat 95℃, 5 min Cool: RT, 15min
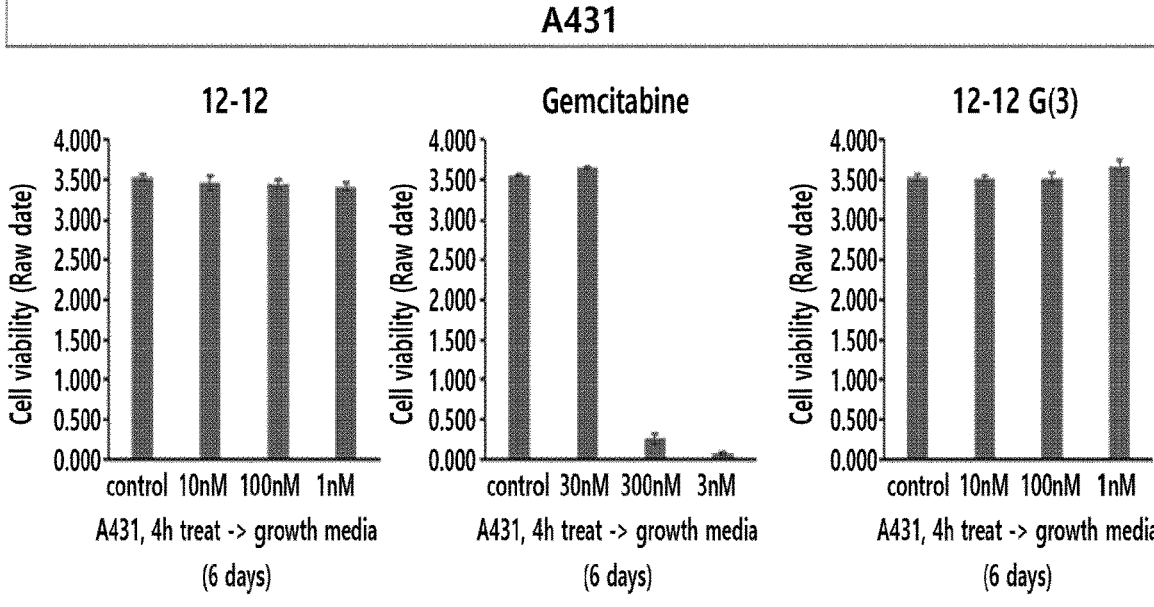
A-431
Aptamer: GPC3 12-12 10, 100, 1000nM
12-12-G(3)_Granlen 10, 100, 1000nM
Gemcitabine 30, 300, 3000nM
Serum free: 1h aptamer treat -> growth media change 6 days incubation
Heat 95℃, 5 min Cool: RT, 15min

[Fig. 13]
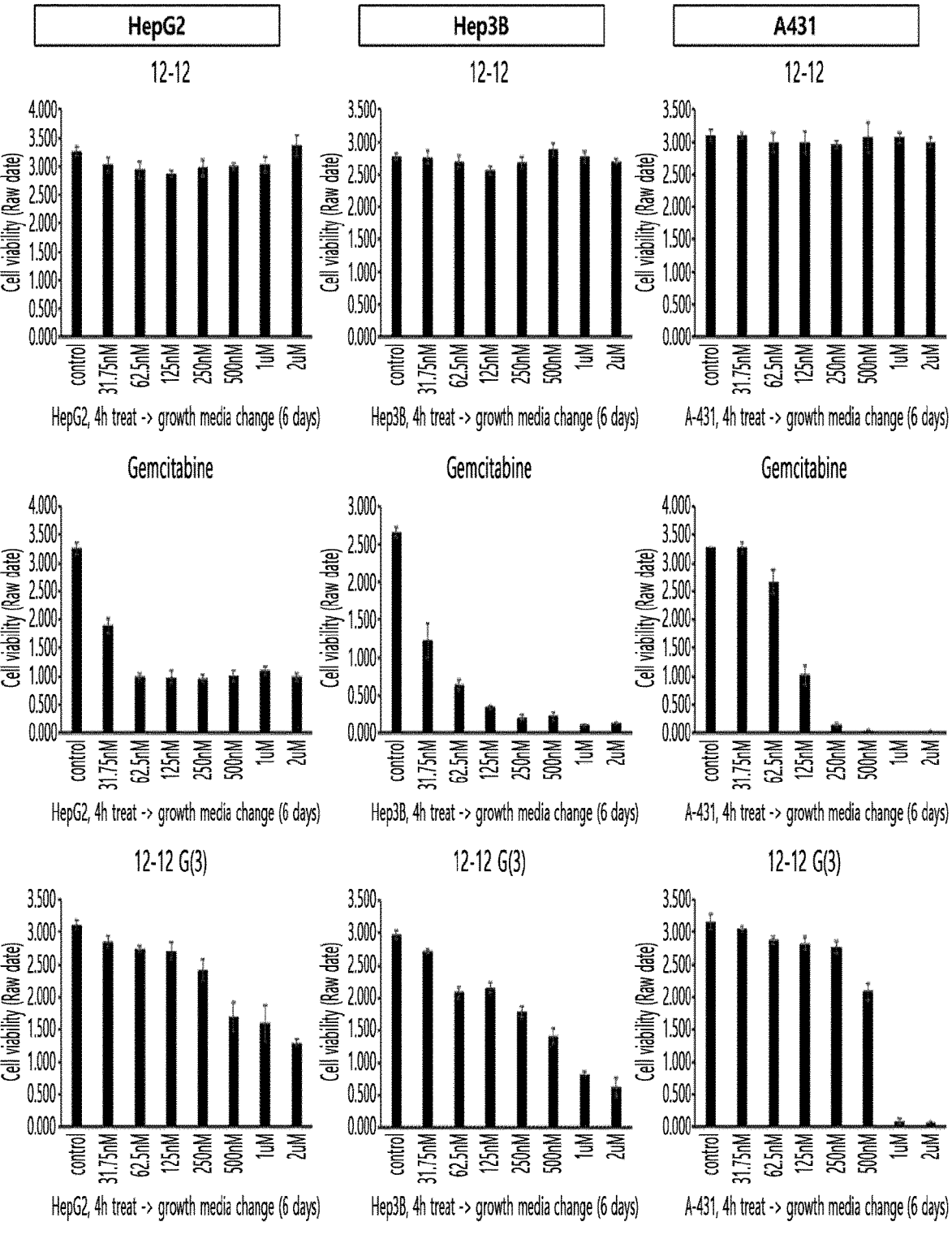
Aptamer: GPC3 12-12 31.75nm-2uM
12-12-G(3)_Granlen 31.75nm-2uM
Gemcitabine 31.75nm-2uM
Serum free: 1h aptamer treat -> growth media change 6 days incubation
Heat 95°C, 5 min Cool: RT, 15min

[Figure 14]

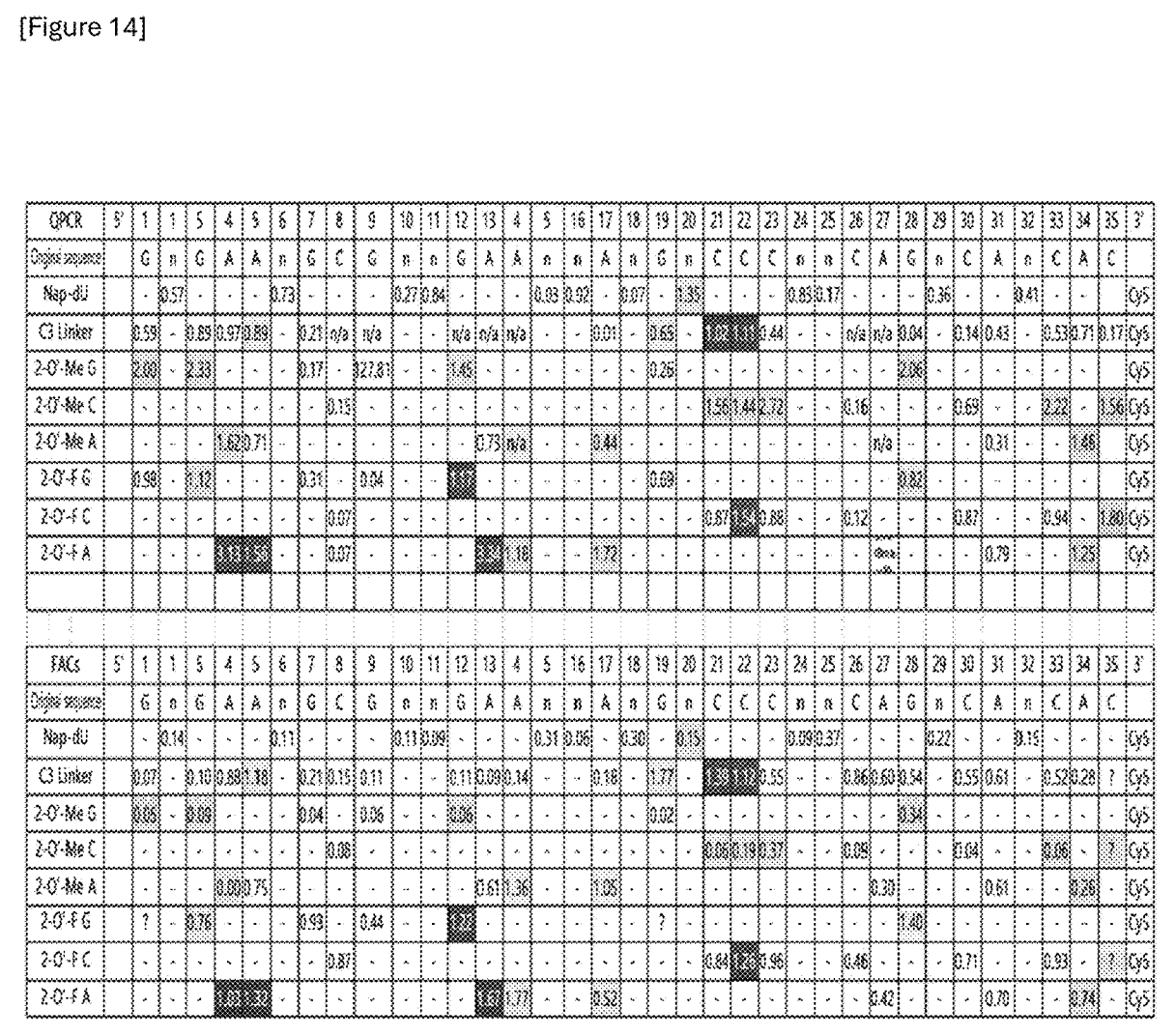

| QPCR | 5' | 1 | 1 | 5 | 4 | 5 | 6 | 7 | 8 | 9 | 10 | 11 | 12 | 13 | 4 | 5 | 16 | 17 | 18 | 19 | 20 | 21 | 22 | 23 | 24 | 25 | 26 | 27 | 28 | 29 | 30 | 31 | 32 | 33 | 34 | 35 | 3' |
|---|---|---|---|---|---|---|---|---|---|---|---|---|---|---|---|---|---|---|---|---|---|---|---|---|---|---|---|---|---|---|---|---|---|---|---|---|---|
| Original sequence | | G | n | G | A | A | n | G | C | G | n | n | G | A | A | n | n | A | n | G | n | C | C | C | n | n | C | A | G | n | C | A | n | C | A | C | |
| Nap-dU | | - | 0.57 | - | - | - | 0.73 | - | - | - | 0.27 | 0.84 | - | - | - | 0.03 | 0.92 | - | 0.07 | 1.35 | - | - | - | - | 0.83 | 0.17 | - | - | - | - | 0.36 | - | - | 0.41 | - | - | Cy5 |
| C3 Linker | 0.59 | - | 0.89 | 0.97 | 0.89 | - | 0.21 | n/a | n/a | - | - | n/a | n/a | n/a | - | - | 0.01 | - | 0.65 | | | 0.44 | - | - | n/a | n/a | 0.04 | - | 0.14 | 0.43 | - | - | 0.53 | 0.71 | 0.17 | Cy5 |
| 2-O'-Me G | | - | 0.33 | - | - | - | 0.17 | - | 0.27 | 0.81 | - | - | 1.65 | - | - | - | - | - | 0.25 | - | - | - | - | - | - | - | - | - | - | - | - | - | - | - | - | Cy5 |
| 2-O'-Me C | - | - | - | - | - | - | 0.15 | - | - | - | - | - | - | - | - | - | - | - | - | - | 1.56 | 1.44 | 2.72 | - | - | 0.16 | - | - | - | 0.69 | - | - | - | - | Cy5 |
| 2-O'-Me A | - | - | - | 1.62 | 0.71 | - | - | - | - | - | - | 0.73 | n/a | - | - | 0.44 | - | - | - | - | - | - | - | n/a | - | - | - | 0.31 | - | - | - | - | Cy5 |
| 2-O'-F G | 0.58 | - | - | - | - | 0.31 | - | 0.04 | - | - | - | - | - | - | - | - | 0.69 | - | - | - | - | - | - | - | - | - | - | - | - | - | - | - | Cy5 |
| 2-O'-F C | - | - | - | - | - | - | 0.07 | - | - | - | - | - | - | - | - | - | - | - | - | - | 0.67 | - | 0.88 | - | - | 0.12 | - | - | - | 0.87 | - | - | 0.94 | - | Cy5 |
| 2-O'-F A | - | - | - | - | - | - | 0.07 | - | - | - | - | - | - | - | - | 0.72 | - | - | - | - | - | - | - | - | - | - | - | - | 0.79 | - | - | - | Cy5 |

| FACs | 5' | 1 | 1 | 5 | 4 | 5 | 6 | 7 | 8 | 9 | 10 | 11 | 12 | 13 | 4 | 5 | 16 | 17 | 18 | 19 | 20 | 21 | 22 | 23 | 24 | 25 | 26 | 27 | 28 | 29 | 30 | 31 | 32 | 33 | 34 | 35 | 3' |
|---|---|---|---|---|---|---|---|---|---|---|---|---|---|---|---|---|---|---|---|---|---|---|---|---|---|---|---|---|---|---|---|---|---|---|---|---|---|
| Original sequence | | G | n | G | A | A | n | G | C | G | n | n | G | A | A | n | n | A | n | G | n | C | C | C | n | n | C | A | G | n | C | A | n | C | A | C | |
| Nap-dU | | - | 0.14 | - | - | - | 0.11 | - | - | - | 0.11 | 0.09 | - | - | - | 0.31 | 0.56 | - | 0.30 | 0.15 | - | - | - | - | 0.09 | 0.37 | - | - | - | - | 0.22 | - | - | 0.15 | - | - | Cy5 |
| C3 Linker | 0.07 | - | 0.10 | 0.88 | 1.38 | - | 0.21 | 0.15 | 0.11 | - | - | 0.11 | 0.09 | 0.14 | - | - | 0.18 | - | 1.77 | | | 0.55 | - | - | 0.86 | 0.60 | 0.54 | - | 0.55 | 0.61 | - | 0.52 | 0.28 | ? | Cy5 |
| 2-O'-Me G | | - | 0.08 | - | - | 0.04 | - | 0.06 | - | - | 0.36 | - | - | - | - | - | - | 0.02 | - | - | - | - | - | - | - | 0.34 | - | - | - | - | - | - | - | - | Cy5 |
| 2-O'-Me C | - | - | - | - | - | - | 0.08 | - | - | - | - | - | - | - | - | - | - | - | - | - | 0.06 | 0.10 | 0.37 | - | - | 0.09 | - | - | - | 0.04 | - | - | 0.06 | ? | Cy5 |
| 2-O'-Me A | - | - | - | 0.00 | 0.75 | - | - | - | - | - | - | 0.61 | 0.36 | - | - | 0.06 | - | - | - | - | - | - | - | - | - | 0.31 | - | - | - | 0.61 | - | - | 0.06 | - | Cy5 |
| 2-O'-F G | ? | - | 0.76 | - | - | 0.93 | - | 0.44 | - | - | - | | - | - | - | ? | - | - | - | - | - | - | - | - | - | 1.40 | - | - | - | - | - | - | Cy5 |
| 2-O'-F C | - | - | - | - | - | - | 0.87 | - | - | - | - | - | - | - | - | - | - | - | - | - | 0.44 | | 0.96 | - | - | 0.46 | - | - | - | 0.71 | - | - | 0.93 | - | ? | Cy5 |
| 2-O'-F A | - | - | - | - | - | - | - | - | - | - | - | 0.71 | - | - | 0.52 | - | - | - | - | - | - | - | - | 0.42 | - | - | - | 0.70 | - | - | 0.74 | - | Cy5 |

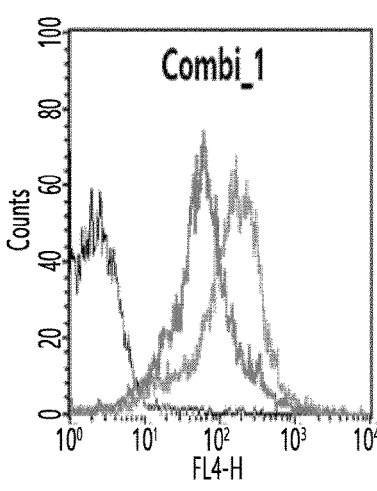

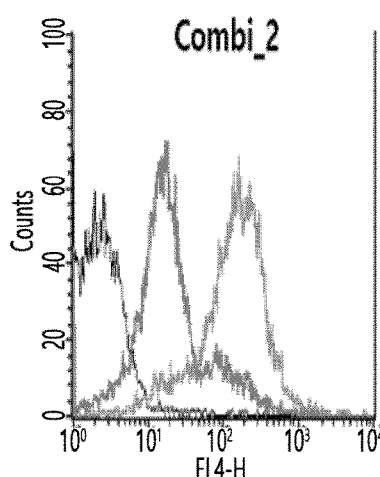

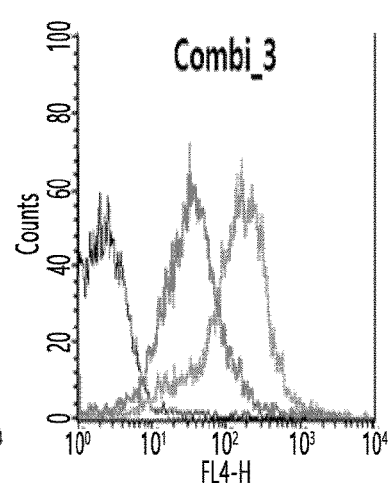

File: COMBI-1.004    Aoquisition Date: 07-May-19
Gated Events: 10000    Total Events: 10000

| Marker | Left,Right | Events | % Gated | % Total | Mean |
|--------|-----------|--------|---------|---------|------|
| All | 1,9910 | 10000 | 100.00 | 100.00 | 81.64 |
| M1 | 1,163 | 9070 | 90.70 | 90.70 | 56.54 |

File: COMBI-2.005    Aoquisition Date: 07-May-19
Gated Events: 10000    Total Events: 10000

| Marker | Left,Right | Events | % Gated | % Total | Mean |
|--------|-----------|--------|---------|---------|------|
| All | 1,9910 | 10000 | 100.00 | 100.00 | 35.12 |
| M1 | 1,163 | 9584 | 95.84 | 95.84 | 25.42 |

File: COMBI-3.006    Aoquisition Date: 07-May-19
Gated Events: 10000    Total Events: 10000

| Marker | Left,Right | Events | % Gated | % Total | Mean |
|--------|-----------|--------|---------|---------|------|
| All | 1,9910 | 10000 | 100.00 | 100.00 | 47.36 |
| M1 | 1,163 | 9702 | 97.02 | 97.02 | 39.32 |

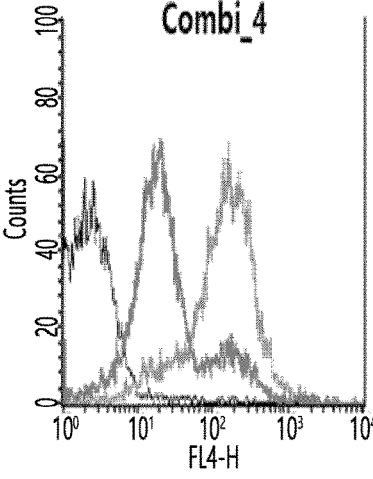

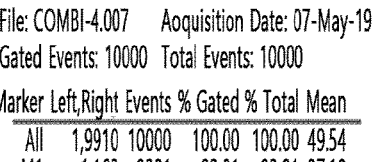

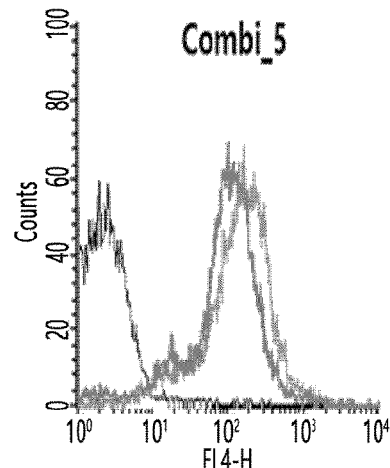

File: COMBI-4.007    Aoquisition Date: 07-May-19
Gated Events: 10000    Total Events: 10000

| Marker | Left,Right | Events | % Gated | % Total | Mean |
|--------|-----------|--------|---------|---------|------|
| All | 1,9910 | 10000 | 100.00 | 100.00 | 49.54 |
| M1 | 1,163 | 9221 | 92.21 | 92.21 | 27.19 |

File: COMBI-3.006    Aoquisition Date: 07-May-19
Gated Events: 10000    Total Events: 10000

| Marker | Left,Right | Events | % Gated | % Total | Mean |
|--------|-----------|--------|---------|---------|------|
| All | 1,9910 | 10000 | 100.00 | 100.00 | 127.36 |
| M1 | 1,163 | 7533 | 75.33 | 75.33 | 82.64 |

[Fig. 17A]
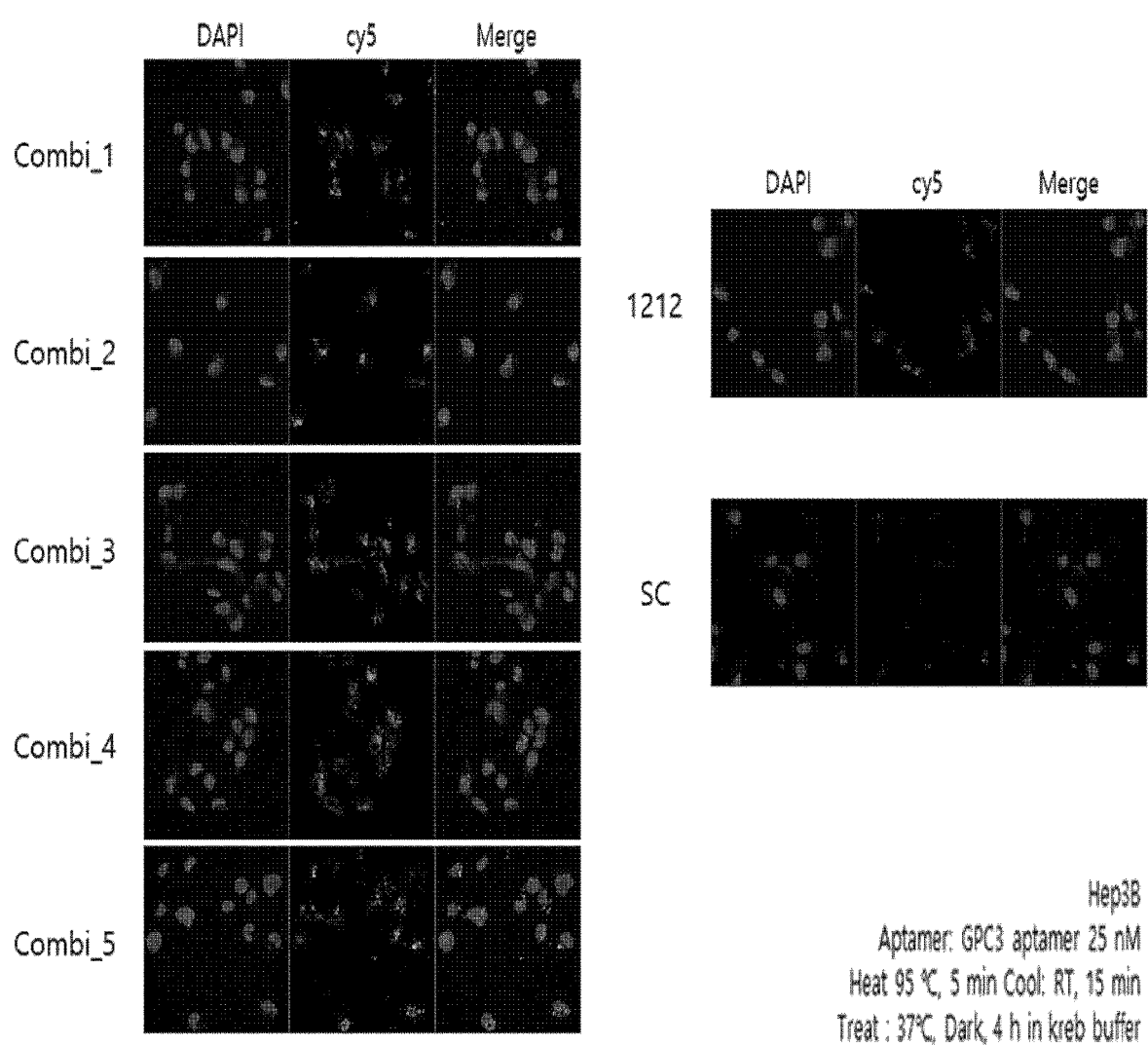

| | 12-12_35mer | Combi 1 | Combi 2 | Combi 3 | Combi 4 | Combi 5 |
|---|---|---|---|---|---|---|
| Kd | 2.77 nM | 3.55 nM | 1.73 nM | n/a | 2.63 nM | 5.72 nM |
| Kd confidence | ±0.68 | ±0.62 | ±0.74 | n/a | ±1.23 | ±2.56 |

| | 12-12_35mer | Combi 4 | Combi 5 | Combi 4 (Gem 3) | Combi 5 (Gem 3) |
|---|---|---|---|---|---|
| Kd | 3.37 nM | 3.76 nM | 5.01 nM | 3.77 nM | 3.53 nM |
| Kd confidence | ±0.5 | ±1.13 | ±2.56 | ±1.66 | ±1.84 |

| | 12-12_35mer | Combi 4 | Combi 5 | Combi 4 (Gem 3) | Combi 5 (Gem 3) | Combi 4 (Gem 5) | Combi 5 (Gem 5) |
|---|---|---|---|---|---|---|---|
| Kd | 1.64 nM | 0.31 nM | 1.31 nM | 0.33 nM | 0.24 nM | n/a | n/a |
| Kd confidence | ±0.35 | ±0.18 | ±0.53 | ±0.17 | ±0.19 | n/a | n/a |

[Fig. 19]
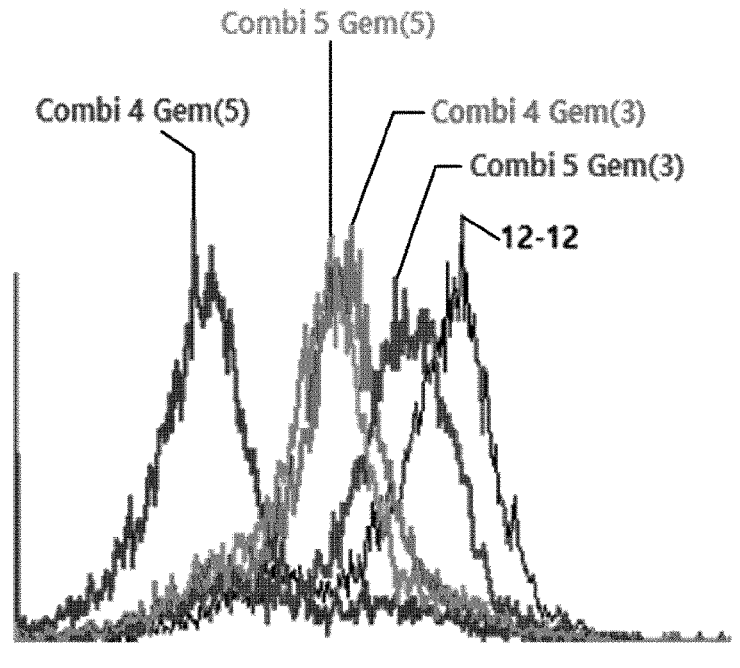
[Fig. 20]
| | DAPI | cy5 | Merge | | | DAPI | cy5 | Merge |
|---|---|---|---|---|---|---|---|---|
| Combi_1 | | | | | control | | | |
| Combi_2 | | | | | 1212 | | | |
| Combi_3 | | | | | SC | | | |
A-431
Aptamer: GPC3 aptamer 25 nM
Heat 95 ℃, 5 min Cool: RT, 15 min
Treat : 37℃, Dark, 4 h in kreb buffer

[Fig. 21]
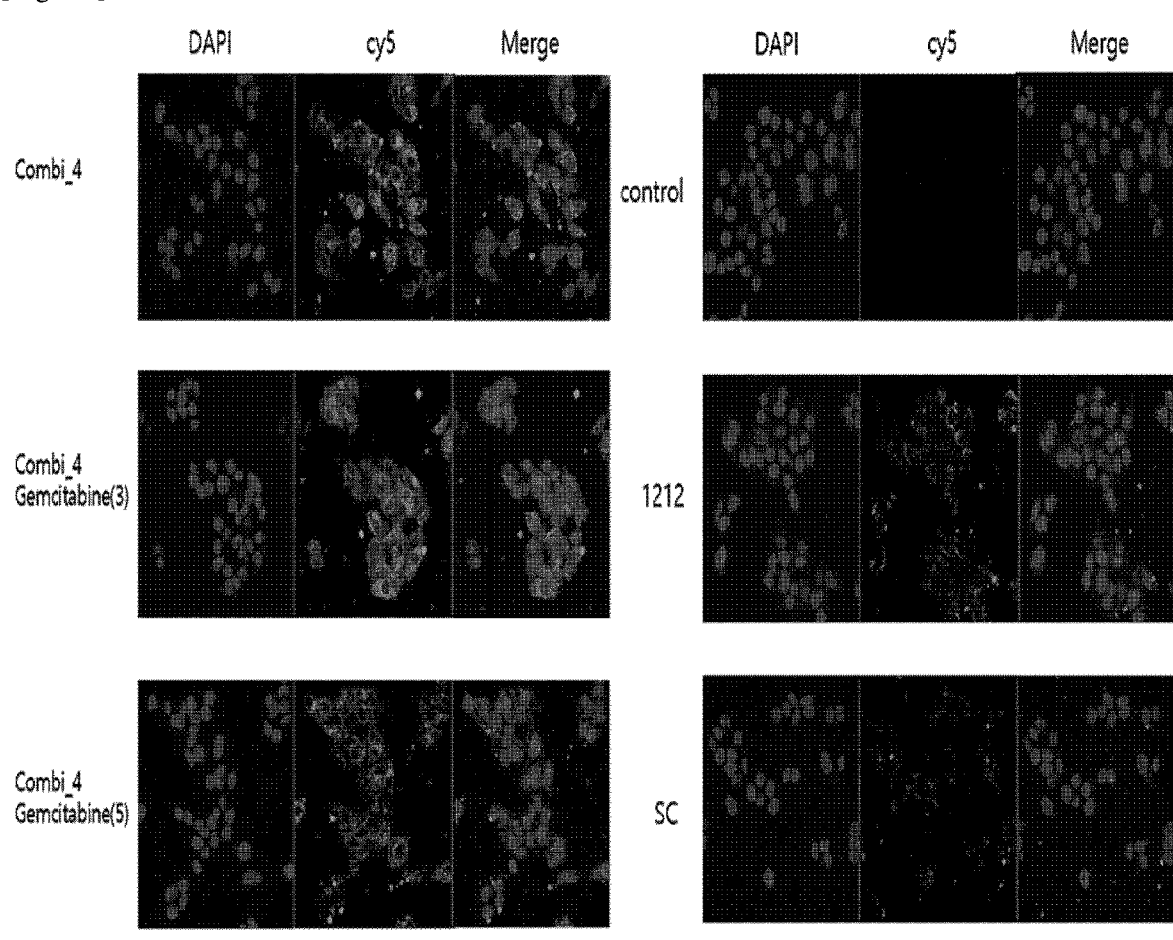
HepG2
Aptamer: GPC3 aptamer 25 nM
Heat 95 ℃, 5 min Cool: RT, 15 min
Treat : 37℃, Dark, 4 h in kreb buffer

[Fig. 22]
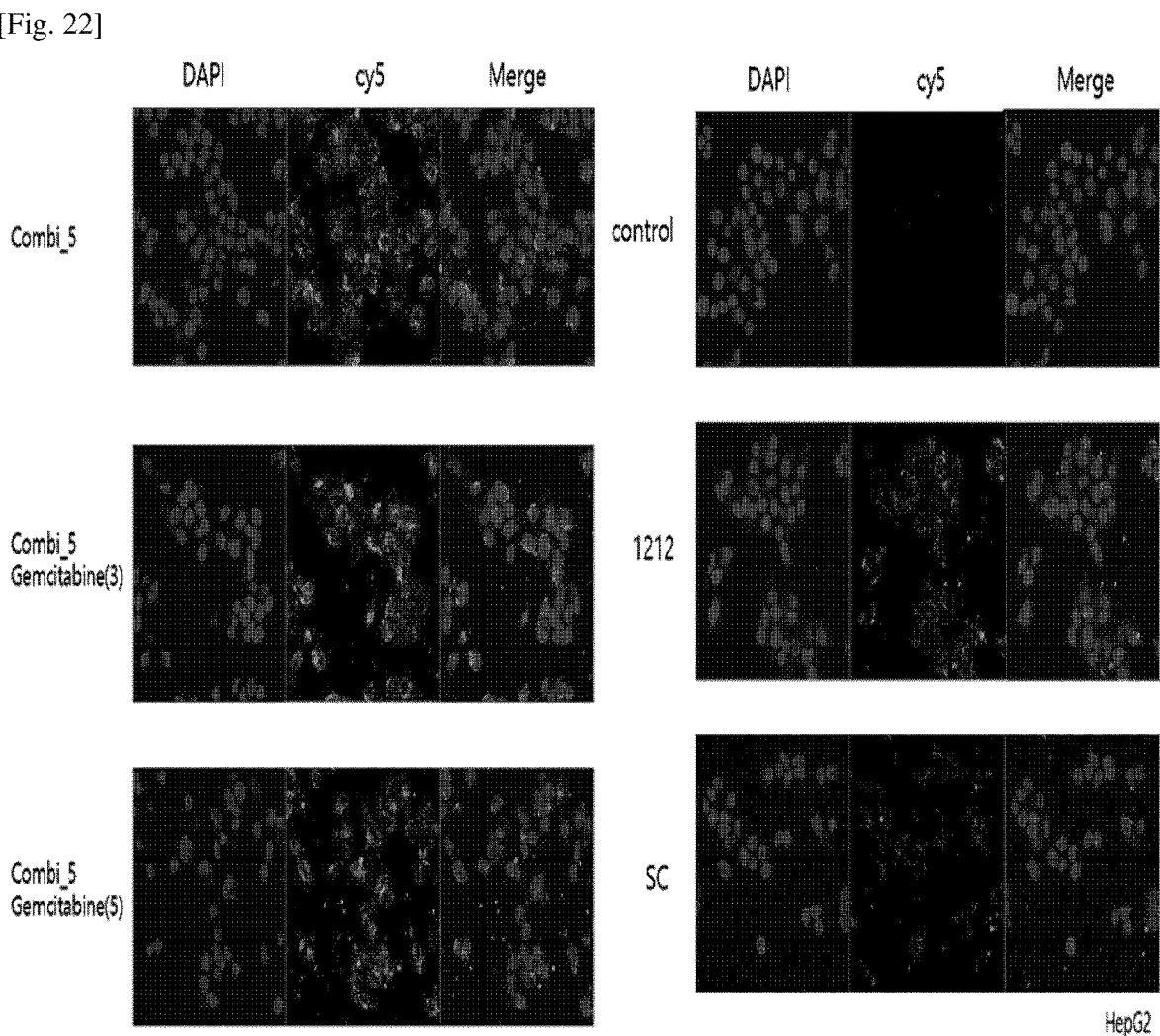

[Fig. 23]
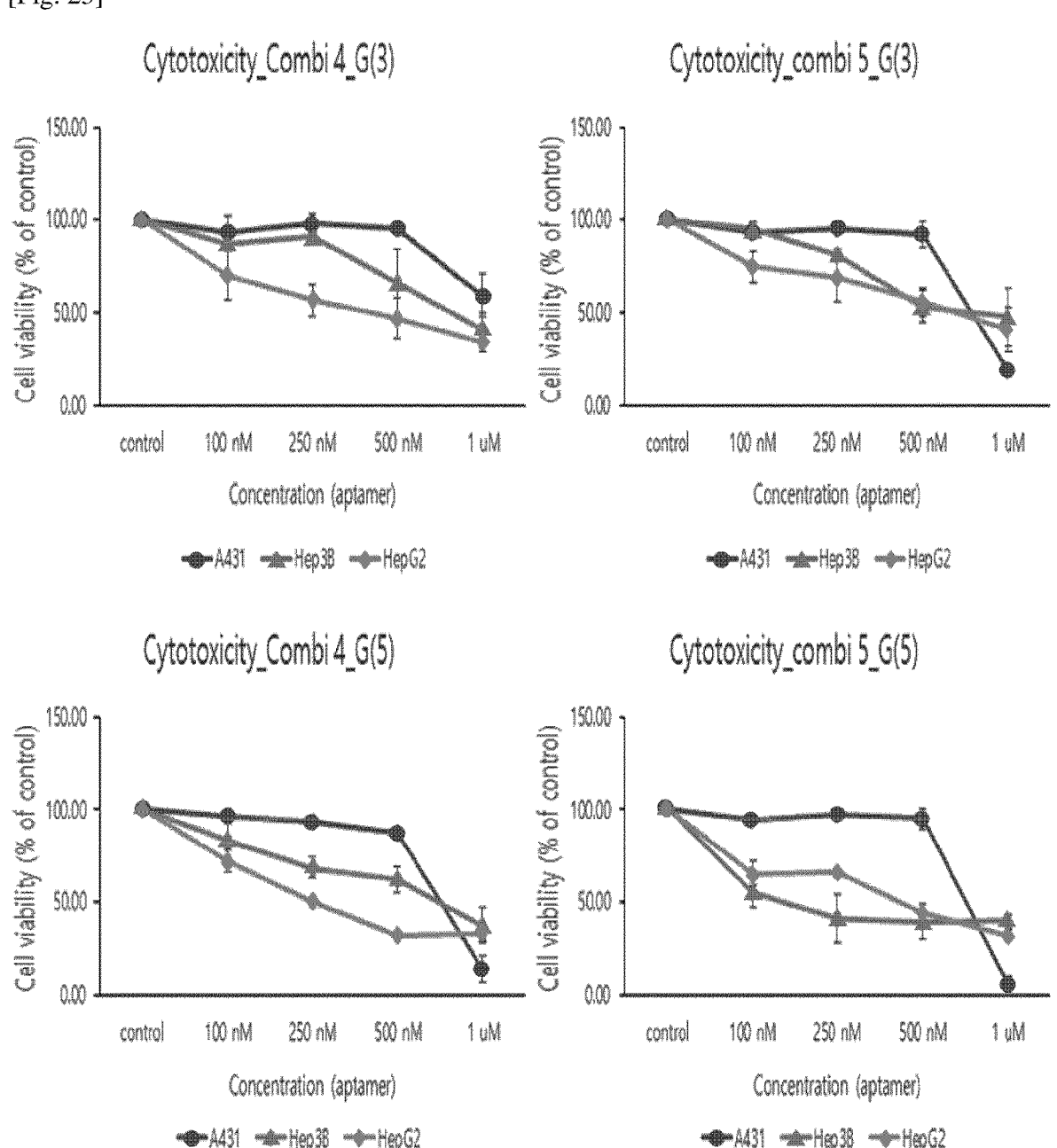

[Fig. 24]

Hep3B, GPC3_Combi 11 G(3)

[Fig. 25A]

Hep3B

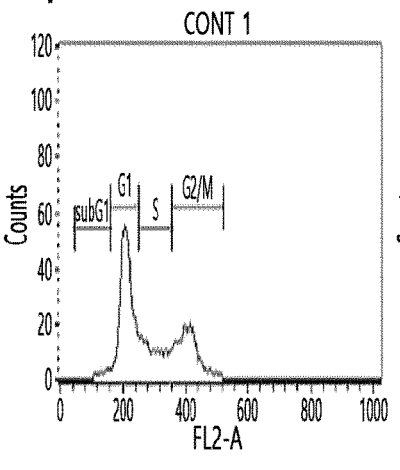

CONT 1

Histogram Statistics

File: CONT 1     Aoquisition Date: 13-Jun-19
Gated Events: 4908     Total Events: 6711

| Marker | Left, Right | Events | % Gated | % Total | Mean |
|---|---|---|---|---|---|
| All | 0, 1023 | 4908 | 100.00 | 73.13 | 283.13 |
| subG1 | 44, 161 | 96 | 1.96 | 1.43 | 138.79 |
| G1 | 161, 250 | 2365 | 48.19 | 35.24 | 210.50 |
| S | 250, 358 | 1122 | 22.86 | 16.72 | 299.17 |
| G2/M | 358, 522 | 1350 | 27.51 | 20.12 | 407.35 |

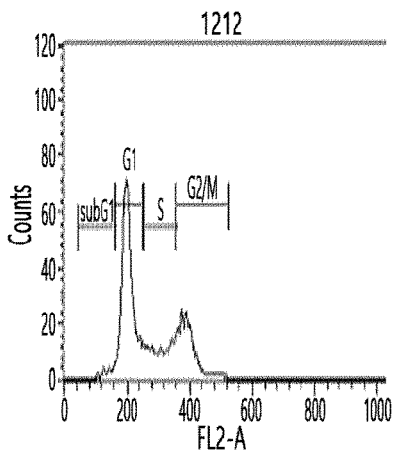

1212

Histogram Statistics

File: 1212     Aoquisition Date: 13-Jun-19
Gated Events: 4923     Total Events: 6538

| Marker | Left, Right | Events | % Gated | % Total | Mean |
|---|---|---|---|---|---|
| All | 0, 1023 | 4923 | 100.00 | 75.30 | 267.89 |
| subG1 | 44, 161 | 87 | 1.77 | 1.33 | 138.76 |
| G1 | 161, 250 | 2630 | 53.42 | 40.23 | 202.40 |
| S | 250, 358 | 1100 | 22.34 | 16.82 | 305.95 |
| G2/M | 358, 522 | 1137 | 23.10 | 17.39 | 392.77 |

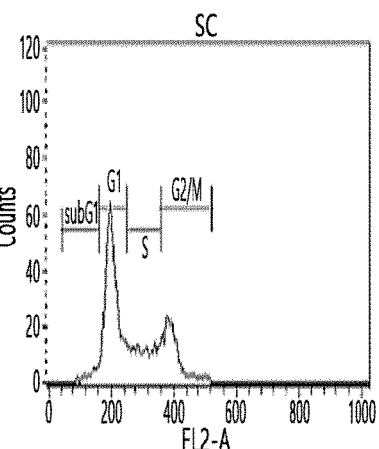

SC

Histogram Statistics

File: SC     Aoquisition Date: 13-Jun-19
Gated Events: 4881     Total Events: 7382

| Marker | Left, Right | Events | % Gated | % Total | Mean |
|---|---|---|---|---|---|
| All | 0, 1023 | 4881 | 100.00 | 65.12 | 268.74 |
| subG1 | 44, 161 | 142 | 2.91 | 1.92 | 140.23 |
| G1 | 161, 250 | 2473 | 50.67 | 33.50 | 202.93 |
| S | 250, 358 | 1190 | 24.37 | 16.12 | 304.22 |
| G2/M | 358, 522 | 1102 | 22.58 | 14.93 | 394.81 |

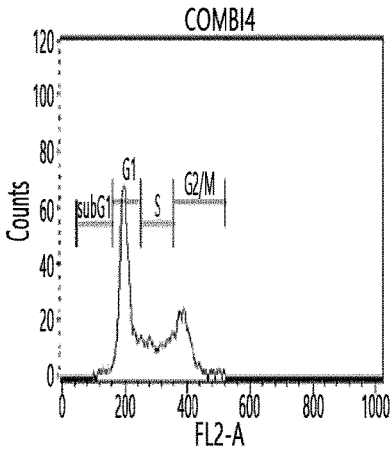

COMBI4

Histogram Statistics

File: COMBI4     Aoquisition Date: 13-Jun-19
Gated Events: 4930     Total Events: 6529

| Marker | Left, Right | Events | % Gated | % Total | Mean |
|---|---|---|---|---|---|
| All | 0, 1023 | 4930 | 100.00 | 75.51 | 271.62 |
| subG1 | 44, 161 | 72 | 1.46 | 1.10 | 138.54 |
| G1 | 161, 250 | 2508 | 50.87 | 38.41 | 202.99 |
| S | 250, 358 | 1233 | 25.01 | 18.88 | 305.41 |
| G2/M | 358, 522 | 1147 | 23.27 | 17.57 | 393.75 |

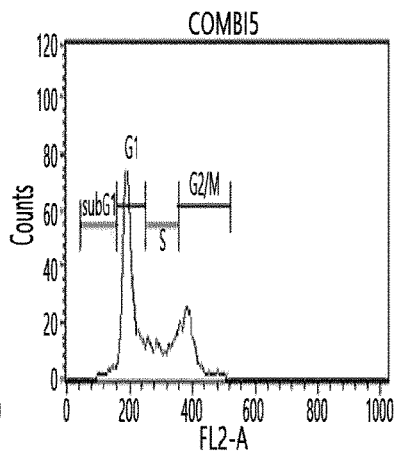

COMBI5

Histogram Statistics

File: COMBI5     Aoquisition Date: 13-Jun-19
Gated Events: 4917     Total Events: 6557

| Marker | Left, Right | Events | % Gated | % Total | Mean |
|---|---|---|---|---|---|
| All | 0, 1023 | 4917 | 100.00 | 74.99 | 269.68 |
| subG1 | 44, 161 | 92 | 1.87 | 1.40 | 138.70 |
| G1 | 161, 250 | 2535 | 51.56 | 38.66 | 201.86 |
| S | 250, 358 | 1152 | 23.43 | 17.57 | 306.15 |
| G2/M | 358, 522 | 1166 | 23.71 | 17.78 | 392.07 |

[Fig. 25B]

Hep3B

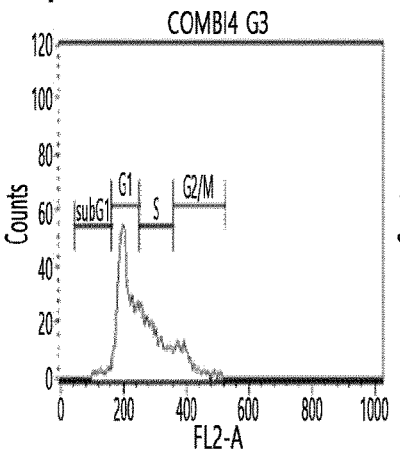

COMBI4 G3

Histogram Statistics

File: COMBI4 G3    Acquisition Date: 13-Jun-19
Gated Events: 4942    Total Events: 6429

| Marker | Left, Right | Events | % Gated | % Total | Mean |
|---|---|---|---|---|---|
| All | 0, 1023 | 4942 | 100.00 | 76.87 | 257.74 |
| subG1 | 44, 161 | 97 | 1.96 | 1.51 | 135.76 |
| G1 | 161, 250 | 2617 | 52.95 | 40.71 | 206.60 |
| S | 250, 358 | 1632 | 33.02 | 25.38 | 294.47 |
| G2/M | 358, 522 | 623 | 12.61 | 9.69 | 394.88 |

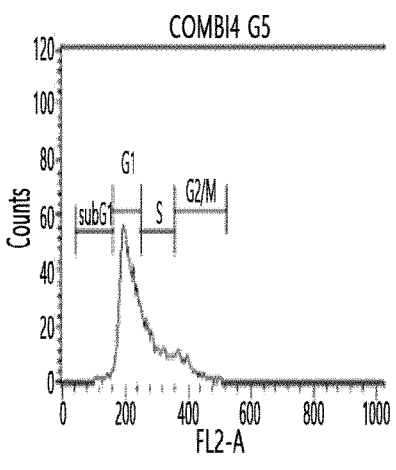

COMBI4 G5

Histogram Statistics

File: COMBI4 G5    Acquisition Date: 13-Jun-19
Gated Events: 4927    Total Events: 6246

| Marker | Left, Right | Events | % Gated | % Total | Mean |
|---|---|---|---|---|---|
| All | 0, 1023 | 4927 | 100.00 | 78.88 | 252.41 |
| subG1 | 44, 161 | 64 | 1.30 | 1.02 | 138.17 |
| G1 | 161, 250 | 2946 | 59.79 | 47.17 | 209.85 |
| S | 250, 358 | 521 | 10.57 | 8.34 | 295.69 |
| G2/M | 358, 522 | 1440 | 29.23 | 23.05 | 293.00 |

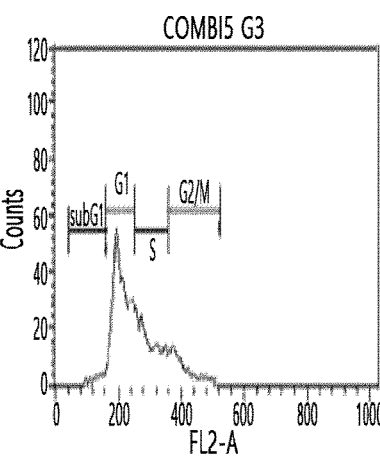

COMBI5 G3

Histogram Statistics

File: COMBI5 G3    Acquisition Date: 13-Jun-19
Gated Events: 4911    Total Events: 6759

| Marker | Left, Right | Events | % Gated | % Total | Mean |
|---|---|---|---|---|---|
| All | 0, 1023 | 4911 | 100.00 | 72.66 | 261.57 |
| subG1 | 44, 161 | 101 | 2.06 | 1.49 | 137.93 |
| G1 | 161, 250 | 2555 | 52.03 | 37.80 | 209.84 |
| S | 250, 358 | 1632 | 33.23 | 24.15 | 294.81 |
| G2/M | 358, 522 | 661 | 13.46 | 9.78 | 399.23 |

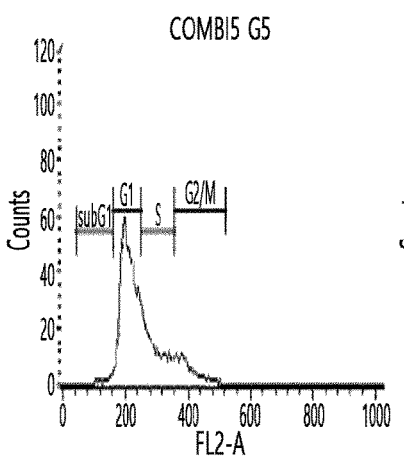

COMBI5 G5

Histogram Statistics

File: COMBI5 G5    Acquisition Date: 13-Jun-19
Gated Events: 4946    Total Events: 6171

| Marker | Left, Right | Events | % Gated | % Total | Mean |
|---|---|---|---|---|---|
| All | 0, 1023 | 4946 | 100.00 | 80.15 | 252.00 |
| subG1 | 44, 161 | 64 | 1.29 | 1.04 | 139.67 |
| G1 | 161, 250 | 3020 | 61.05 | 48.94 | 210.74 |
| S | 250, 358 | 1372 | 27.74 | 22.23 | 292.36 |
| G2/M | 358, 522 | 527 | 10.66 | 8.54 | 397.53 |

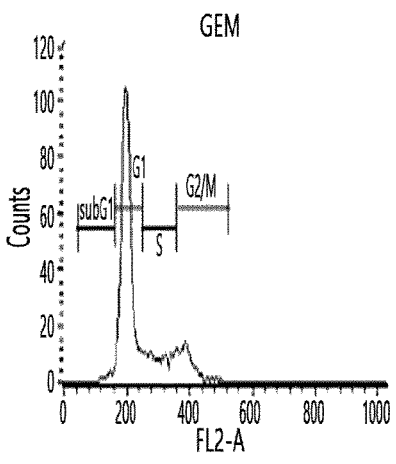

GEM

Histogram Statistics

File: GEM    Acquisition Date: 13-Jun-19
Gated Events: 4934    Total Events: 6197

| Marker | Left, Right | Events | % Gated | % Total | Mean |
|---|---|---|---|---|---|
| All | 0, 1023 | 4934 | 100.00 | 79.62 | 242.64 |
| subG1 | 44, 161 | 67 | 1.36 | 1.06 | 139.22 |
| G1 | 161, 250 | 3419 | 69.29 | 55.17 | 202.52 |
| S | 250, 358 | 833 | 16.88 | 13.44 | 302.33 |
| G2/M | 358, 522 | 636 | 12.93 | 10.30 | 392.47 |

[Fig. 26A]

HepG2

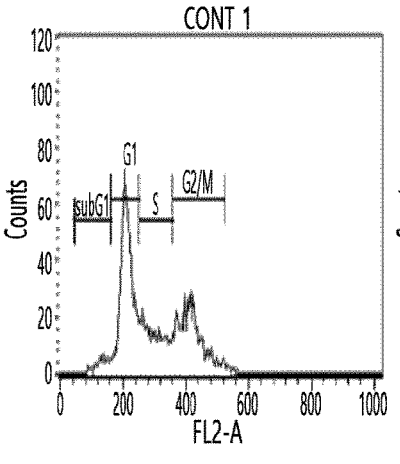

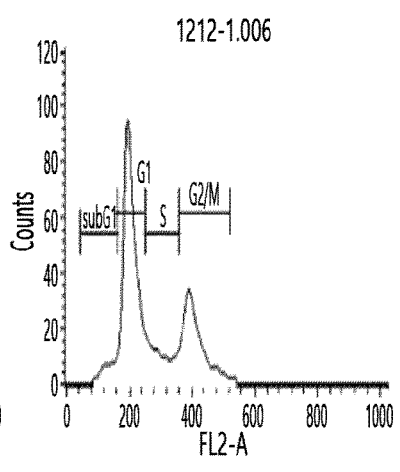

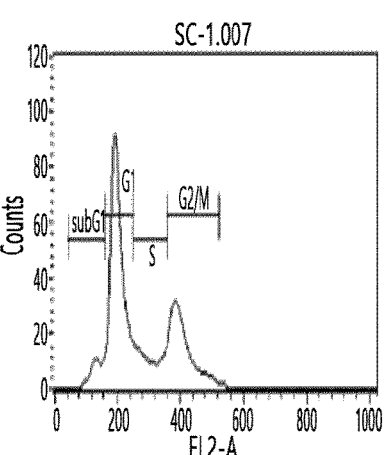

Histogram Statistics

File: CONT 1    Aoquisition Date: 17-Jun-19
Gated Events: 5265    Total Events: 6711

| Marker | Left, Right | Events | % Gated | % Total | Mean |
|---|---|---|---|---|---|
| All | 0, 1023 | 5265 | 100.00 | 78.45 | 289.36 |
| subG1 | 44, 161 | 132 | 2.51 | 1.97 | 135.47 |
| G1 | 161, 250 | 2389 | 45.38 | 35.60 | 210.50 |
| S | 250, 358 | 1191 | 22.62 | 17.75 | 299.64 |
| G2/M | 358, 522 | 1563 | 29.69 | 23.29 | 412.53 |

Histogram Statistics

File: 1212-1.006    Aoquisition Date: 17-Jun-19
Gated Events: 7606    Total Events: 10000

| Marker | Left, Right | Events | % Gated | % Total | Mean |
|---|---|---|---|---|---|
| All | 0, 1023 | 7606 | 100.00 | 76.06 | 270.87 |
| subG1 | 44, 161 | 359 | 4.85 | 3.69 | 132.37 |
| G1 | 161, 250 | 4022 | 52.88 | 40.22 | 203.53 |
| S | 250, 358 | 1150 | 15.12 | 11.50 | 298.15 |
| G2/M | 358, 522 | 2083 | 27.39 | 20.83 | 408.35 |

Histogram Statistics

File: SC-1.007    Aoquisition Date: 17-Jun-19
Gated Events: 7511    Total Events: 10000

| Marker | Left, Right | Events | % Gated | % Total | Mean |
|---|---|---|---|---|---|
| All | 0, 1023 | 7511 | 100.00 | 75.11 | 268.66 |
| subG1 | 44, 161 | 466 | 6.20 | 4.66 | 134.49 |
| G1 | 161, 250 | 3820 | 50.86 | 38.20 | 200.92 |
| S | 250, 358 | 1210 | 16.11 | 12.10 | 300.53 |
| G2/M | 358, 522 | 2039 | 27.15 | 20.39 | 405.35 |

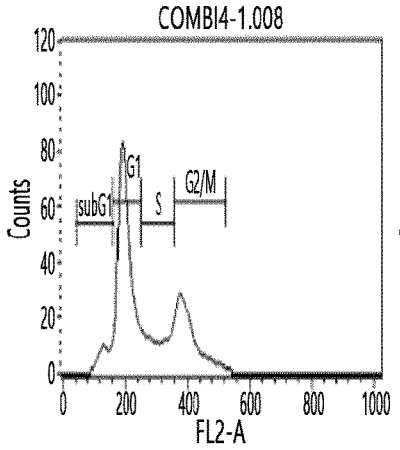

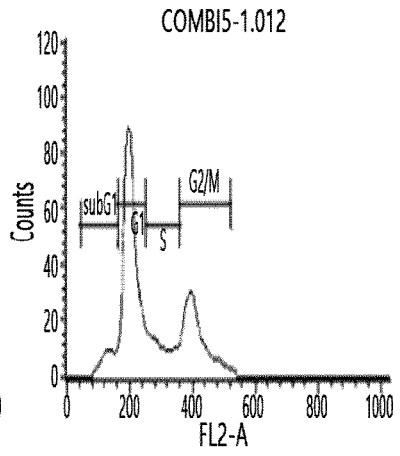

Histogram Statistics

File: COMBI4-1.008    Aoquisition Date: 17-Jun-19
Gated Events: 7369    Total Events: 10000

| Marker | Left, Right | Events | % Gated | % Total | Mean |
|---|---|---|---|---|---|
| All | 0, 1023 | 7369 | 100.00 | 73.69 | 266.47 |
| subG1 | 44, 161 | 458 | 6.22 | 4.58 | 134.23 |
| G1 | 161, 250 | 3740 | 50.75 | 37.40 | 199.97 |
| S | 250, 358 | 1350 | 18.32 | 13.50 | 304.17 |
| G2/M | 358, 522 | 1846 | 25.05 | 18.46 | 404.39 |

Histogram Statistics

File: COMBI5-1.012    Aoquisition Date: 17-Jun-19
Gated Events: 7437    Total Events: 10000

| Marker | Left, Right | Events | % Gated | % Total | Mean |
|---|---|---|---|---|---|
| All | 0, 1023 | 7437 | 100.00 | 74.37 | 272.13 |
| subG1 | 44, 161 | 465 | 6.25 | 4.65 | 132.82 |
| G1 | 161, 250 | 3756 | 50.50 | 37.56 | 204.71 |
| S | 250, 358 | 1222 | 16.43 | 12.22 | 299.32 |
| G2/M | 358, 522 | 1995 | 26.83 | 19.96 | 411.67 |

[Fig. 26B]

HepG2

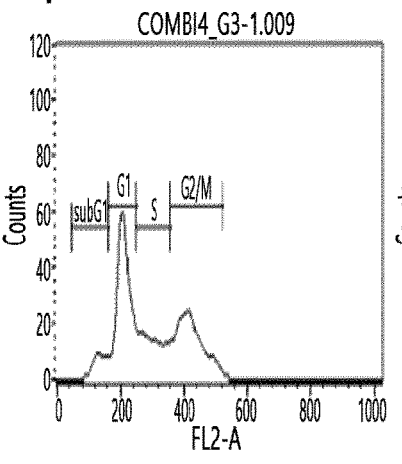

Histogram Statistics

File: COMBI4_G3-1.009  Acquisition Date: 17-Jun-19
Gated Events: 7043   Total Events: 10000

| Marker | Left, Right | Events | % Gated | % Total | Mean |
|---|---|---|---|---|---|
| All | 0, 1023 | 7043 | 100.00 | 70.43 | 293.77 |
| subG1 | 44, 161 | 459 | 4.59 | 4.59 | 133.00 |
| G1 | 161, 250 | 2754 | 27.54 | 27.54 | 209.45 |
| S | 250, 358 | 1575 | 15.75 | 15.75 | 300.95 |
| G2/M | 358, 522 | 2284 | 22.84 | 22.84 | 421.06 |

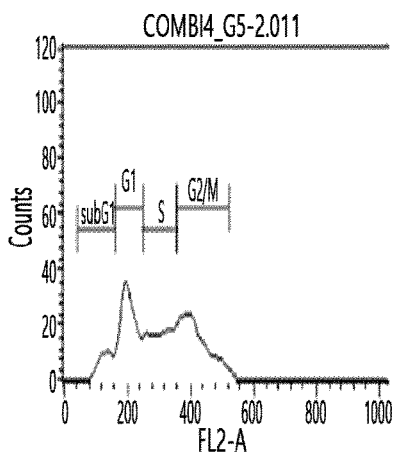

Histogram Statistics

File: COMBI4_G5-2.011  Acquisition Date: 17-Jun-19
Gated Events: 6565   Total Events: 10000

| Marker | Left, Right | Events | % Gated | % Total | Mean |
|---|---|---|---|---|---|
| All | 0, 1023 | 6565 | 100.00 | 65.65 | 301.57 |
| subG1 | 44, 161 | 522 | 7.95 | 5.22 | 131.73 |
| G1 | 161, 250 | 1954 | 29.76 | 19.54 | 204.72 |
| S | 250, 358 | 2270 | 34.58 | 22.70 | 416.93 |
| G2/M | 358, 522 | 1831 | 27.89 | 18.31 | 605.45 |

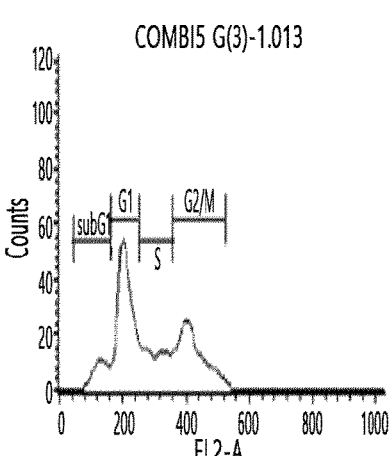

Histogram Statistics

File: COMBI5 G(3)-1.013  Acquisition Date: 17-Jun-19
Gated Events: 6577   Total Events: 10000

| Marker | Left, Right | Events | % Gated | % Total | Mean |
|---|---|---|---|---|---|
| All | 0, 1023 | 6577 | 100.00 | 65.77 | 286.71 |
| subG1 | 44, 161 | 527 | 8.01 | 5.27 | 131.57 |
| G1 | 161, 250 | 2618 | 39.81 | 26.18 | 209.07 |
| S | 250, 358 | 1401 | 21.30 | 14.01 | 301.54 |
| G2/M | 358, 522 | 2053 | 31.21 | 20.53 | 419.63 |

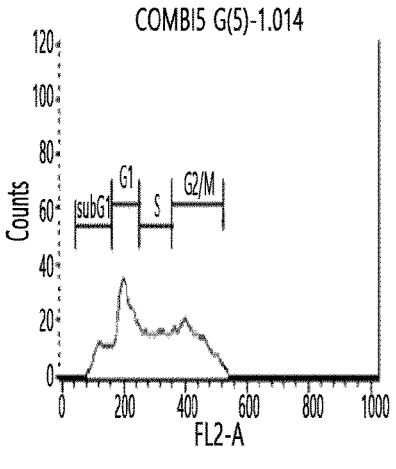

Histogram Statistics

File: COMBI5 G(5)-1.014  Acquisition Date: 17-Jun-19
Gated Events: 6304   Total Events: 10000

| Marker | Left, Right | Events | % Gated | % Total | Mean |
|---|---|---|---|---|---|
| All | 0, 1023 | 6304 | 100.00 | 63.04 | 299.54 |
| subG1 | 44, 161 | 580 | 9.20 | 5.80 | 132.38 |
| G1 | 161, 250 | 1962 | 31.12 | 19.62 | 209.43 |
| S | 250, 358 | 1681 | 26.67 | 16.81 | 303.52 |
| G2/M | 358, 522 | 2105 | 33.39 | 21.05 | 423.09 |

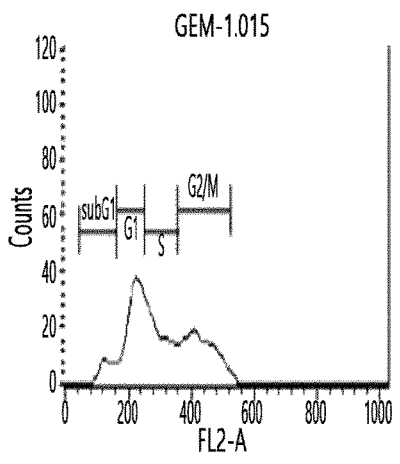

Histogram Statistics

File: GEM-1.015  Acquisition Date: 17-Jun-19
Gated Events: 6598   Total Events: 10000

| Marker | Left, Right | Events | % Gated | % Total | Mean |
|---|---|---|---|---|---|
| All | 0, 1023 | 6598 | 100.00 | 65.98 | 307.32 |
| subG1 | 44, 161 | 379 | 5.74 | 3.79 | 133.40 |
| G1 | 161, 250 | 2053 | 31.12 | 20.53 | 218.47 |
| S | 250, 358 | 2031 | 30.78 | 20.31 | 295.90 |
| G2/M | 358, 522 | 2151 | 32.60 | 21.51 | 428.56 |

[Fig. 27A]

A431(Control cell line)

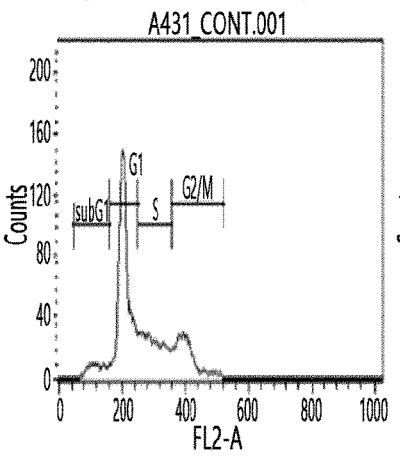

Histogram Statistics

File: A431_CONT.001   Aoquisition Date: 28-Jun-19
Gated Events: 9496   Total Events: 10000

| Marker | Left, Right | Events | % Gated | % Total | Mean |
|---|---|---|---|---|---|
| All | 0, 1023 | 9496 | 100.00 | 94.96 | 259.72 |
| subG1 | 44, 161 | 517 | 5.44 | 5.17 | 119.88 |
| G1 | 161, 250 | 4914 | 51.75 | 49.14 | 206.99 |
| S | 250, 358 | 2427 | 25.56 | 24.27 | 296.79 |
| G2/M | 358, 522 | 1691 | 17.81 | 16.91 | 400.14 |

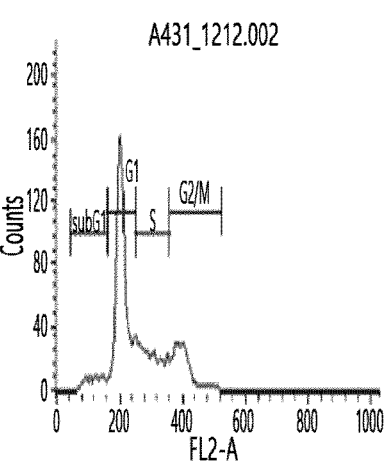

Histogram Statistics

File: A431_1212.002   Aoquisition Date: 28-Jun-19
Gated Events: 9537   Total Events: 10000

| Marker | Left, Right | Events | % Gated | % Total | Mean |
|---|---|---|---|---|---|
| All | 0, 1023 | 9537 | 100.00 | 95.37 | 257.69 |
| subG1 | 44, 161 | 512 | 5.37 | 5.12 | 119.14 |
| G1 | 161, 250 | 5086 | 53.33 | 50.86 | 206.20 |
| S | 250, 358 | 2287 | 23.98 | 22.87 | 298.27 |
| G2/M | 358, 522 | 1707 | 17.90 | 17.07 | 398.92 |

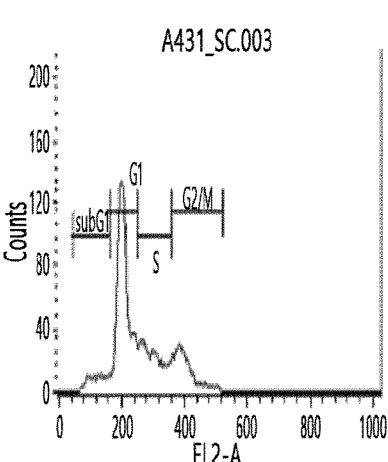

Histogram Statistics

File: A431_SC.003   Aoquisition Date: 28-Jun-19
Gated Events: 9497   Total Events: 10000

| Marker | Left, Right | Events | % Gated | % Total | Mean |
|---|---|---|---|---|---|
| All | 0, 1023 | 9497 | 100.00 | 94.97 | 255.95 |
| subG1 | 44, 161 | 616 | 6.49 | 6.16 | 121.17 |
| G1 | 161, 250 | 4932 | 51.93 | 49.32 | 205.49 |
| S | 250, 358 | 2350 | 24.71 | 23.50 | 297.42 |
| G2/M | 358, 522 | 1651 | 17.38 | 16.51 | 398.51 |

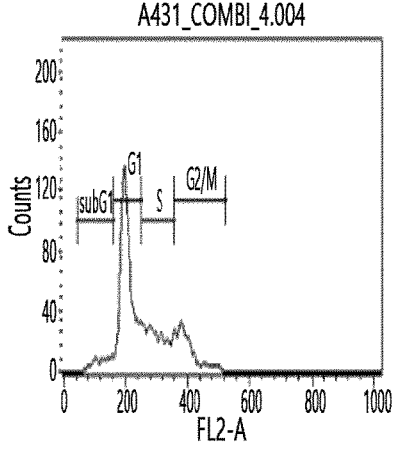

Histogram Statistics

File: A431_COMBI_4.004   Aoquisition Date: 28-Jun-19
Gated Events: 9583   Total Events: 10000

| Marker | Left, Right | Events | % Gated | % Total | Mean |
|---|---|---|---|---|---|
| All | 0, 1023 | 9583 | 100.00 | 95.83 | 255.47 |
| subG1 | 44, 161 | 491 | 5.12 | 4.91 | 124.18 |
| G1 | 161, 250 | 5083 | 53.04 | 50.63 | 203.66 |
| S | 250, 358 | 2512 | 26.21 | 25.12 | 299.64 |
| G2/M | 358, 522 | 1554 | 16.22 | 15.54 | 395.70 |

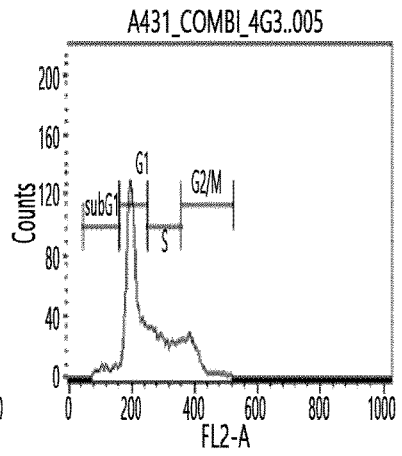

Histogram Statistics

File: A431_COMBI_4G3.005   Aoquisition Date: 28-Jun-19
Gated Events: 9510   Total Events: 10000

| Marker | Left, Right | Events | % Gated | % Total | Mean |
|---|---|---|---|---|---|
| All | 0, 1023 | 9510 | 100.00 | 95.10 | 256.94 |
| subG1 | 44, 161 | 453 | 4.76 | 4.53 | 121.53 |
| G1 | 161, 250 | 4928 | 51.82 | 49.28 | 204.36 |
| S | 250, 358 | 2586 | 28.24 | 25.86 | 299.83 |
| G2/M | 358, 522 | 1506 | 15.86 | 15.08 | 934.13 |

[Fig. 27B]

A431(Control cell line)

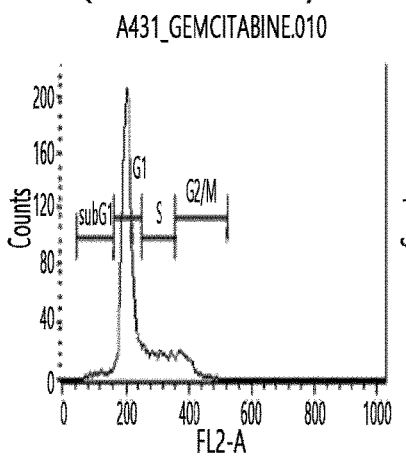

A431_GEMCITABINE.010

Histogram Statistics

File: A431_GEMCITABINE.010　Aoquisition Date: 28-Jun-19
Gated Events: 9590　　　Total Events: 10000

| Marker | Left, Right | Events | % Gated | % Total | Mean |
|---|---|---|---|---|---|
| All | 0, 1023 | 9590 | 100.00 | 95.90 | 240.05 |
| subG1 | 44, 161 | 205 | 2.14 | 2.05 | 126.71 |
| G1 | 161, 250 | 6780 | 70.70 | 67.80 | 207.91 |
| S | 250, 358 | 1738 | 18.12 | 17.38 | 300.73 |
| G2/M | 358, 522 | 910 | 9.49 | 9.10 | 391.30 |

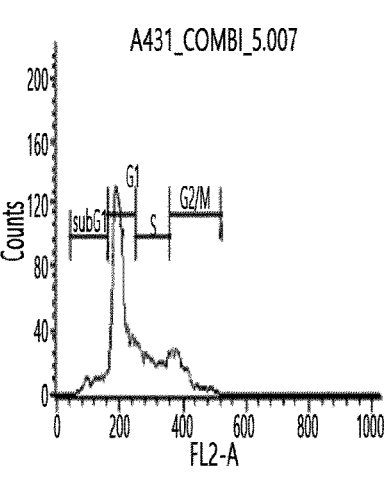

A431_COMBI_5.007

Histogram Statistics

File: A431_COMBI_5.007　Aoquisition Date: 28-Jun-19
Gated Events: 9520　　　Total Events: 10000

| Marker | Left, Right | Events | % Gated | % Total | Mean |
|---|---|---|---|---|---|
| All | 0, 1023 | 9520 | 100.00 | 95.20 | 248.79 |
| subG1 | 44, 161 | 544 | 5.71 | 5.44 | 124.27 |
| G1 | 161, 250 | 5357 | 56.27 | 53.57 | 202.05 |
| S | 250, 358 | 2278 | 22.78 | 22.78 | 298.77 |
| G2/M | 358, 522 | 1397 | 14.67 | 13.97 | 395.06 |

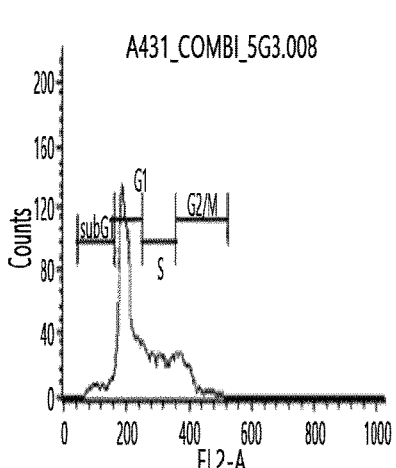

A431_COMBI_5G3.008

Histogram Statistics

File: A431_COMBI_5G3.008　Aoquisition Date: 28-Jun-19
Gated Events: 9541　　　Total Events: 10000

| Marker | Left, Right | Events | % Gated | % Total | Mean |
|---|---|---|---|---|---|
| All | 0, 1023 | 9540 | 100.00 | 95.41 | 250.30 |
| subG1 | 44, 161 | 457 | 4.79 | 4.57 | 122.65 |
| G1 | 161, 250 | 5265 | 55.18 | 52.65 | 202.23 |
| S | 250, 358 | 2577 | 27.01 | 25.77 | 300.06 |
| G2/M | 358, 522 | 1305 | 13.05 | 13.05 | 392.13 |

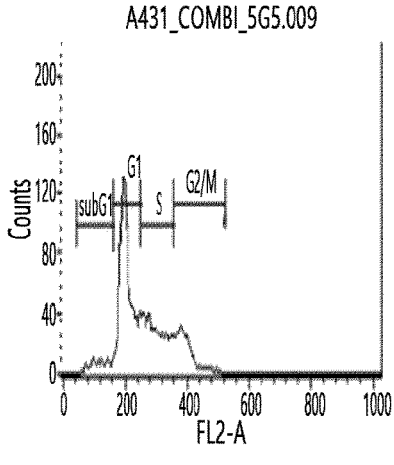

A431_COMBI_5G5.009

Histogram Statistics

File: A431_COMBI_5G5.009　Aoquisition Date: 28-Jun-19
Gated Events: 9600　　　Total Events: 10000

| Marker | Left, Right | Events | % Gated | % Total | Mean |
|---|---|---|---|---|---|
| All | 0, 1023 | 9600 | 100.00 | 96.00 | 251.53 |
| subG1 | 44, 161 | 436 | 4.54 | 4.36 | 119.63 |
| G1 | 161, 250 | 4659 | 48.53 | 46.59 | 206.90 |
| S | 250, 358 | 3011 | 31.36 | 30.11 | 298.58 |
| G2/M | 358, 522 | 1560 | 16.25 | 15.60 | 394.07 |

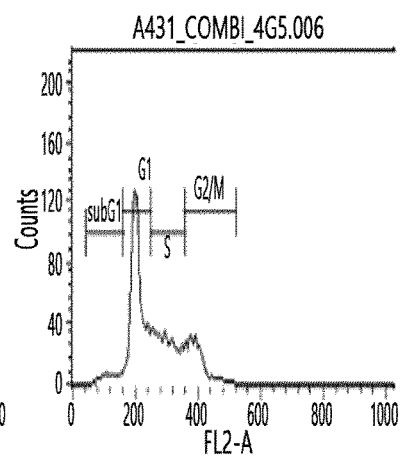

A431_COMBI_4G5.006

Histogram Statistics

File: A431_COMBI_4G5.006　Aoquisition Date: 28-Jun-19
Gated Events: 9559　　　Total Events: 10000

| Marker | Left, Right | Events | % Gated | % Total | Mean |
|---|---|---|---|---|---|
| All | 0, 1023 | 9559 | 100.00 | 95.59 | 262.66 |
| subG1 | 44, 161 | 398 | 4.16 | 3.98 | 121.24 |
| G1 | 161, 250 | 4693 | 49.10 | 46.93 | 206.45 |
| S | 250, 358 | 1644 | 17.20 | 16.44 | 393.88 |
| G2/M | 358, 522 | 2876 | 30.09 | 28.76 | 299.58 |

[Fig. 28]
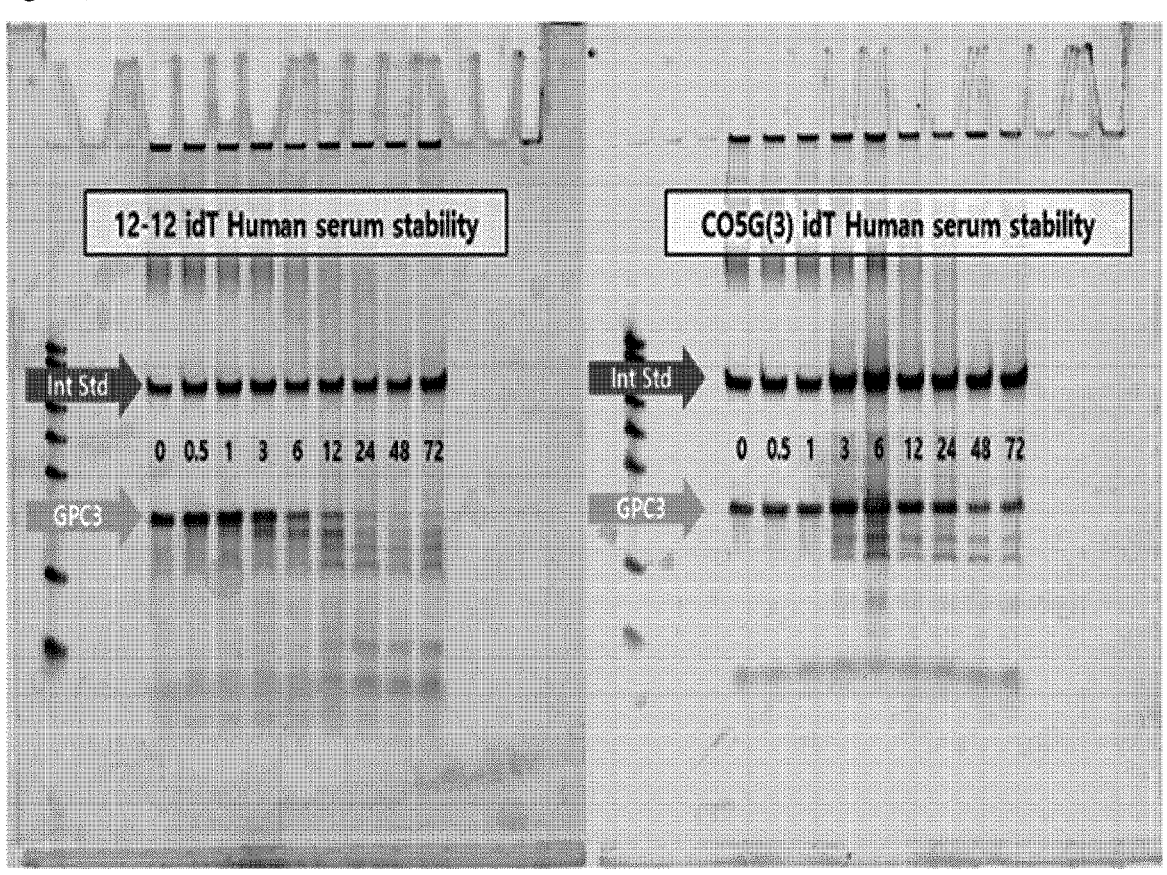
Human serum
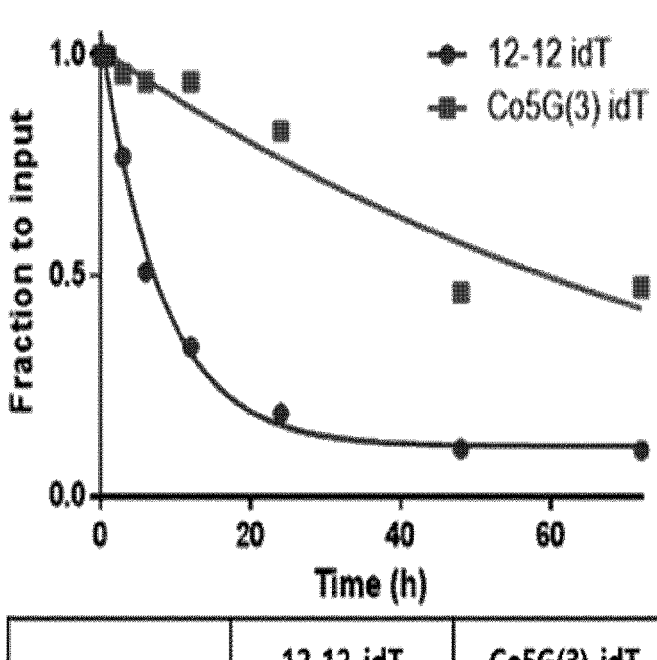
|  | 12-12 idT | Co5G(3) idT |
|---|---|---|
| Half Life(h) | 5.627 | 63.74 |

SEQUENCE LISTING

<160> NUMBER OF SEQ ID NOS: 25

<210> SEQ ID NO 1
<211> LENGTH: 40
<212> TYPE: DNA
<213> ORGANISM: Artificial Sequence
<220> FEATURE:
<223> OTHER INFORMATION: 12-10
<220> FEATURE:
<221> NAME/KEY: misc_feature
<222> LOCATION: (7)..(7)
<223> OTHER INFORMATION: n is BzdU.
<220> FEATURE:

<210> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (20)..(20)
<223> OTHER INFORMATION: n is BzdU.
<220> FEATURE:
<221> NAME/KEY: misc_feature
<222> LOCATION: (21)..(21)
<223> OTHER INFORMATION: n is BzdU.
<220> FEATURE:
<221> NAME/KEY: misc_feature
<222> LOCATION: (23)..(23)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (30)..(30)
<223> OTHER INFORMATION: n is BzdU.
<220> FEATURE:
<221> NAME/KEY: misc_feature
<222> LOCATION: (34)..(34)
<223> OTHER INFORMATION: n is BzdU.
<220> FEATURE:
<221> NAME/KEY: misc_feature
<222> LOCATION: (37)..(37)
<223> OTHER INFORMATION: n is BzdU.

<400> SEQUENCE: 1
gggaagngaa ngcgnngaan nangncccnn cagncancac                                         40

<210> SEQ ID NO 2
<211> LENGTH: 42
<212> TYPE: DNA
<213> ORGANISM: Artificial Sequence
<220> FEATURE:
<223> OTHER INFORMATION: 12-10 G(2)3'
<220> FEATURE:
<221> NAME/KEY: misc_feature
<222> LOCATION: (7)..(7)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (20)..(20)
<223> OTHER INFORMATION: n is BzdU.
<220> FEATURE:
<221> NAME/KEY: misc_feature
<222> LOCATION: (21)..(21)
<223> OTHER INFORMATION: n is BzdU.

```
<220> FEATURE:
<221> NAME/KEY: misc_feature
<222> LOCATION: (23)..(23)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (30)..(30)
<223> OTHER INFORMATION: n is BzdU.
<220> FEATURE:
<221> NAME/KEY: misc_feature
<222> LOCATION: (34)..(34)
<223> OTHER INFORMATION: n is BzdU.
<220> FEATURE:
<221> NAME/KEY: misc_feature
<222> LOCATION: (37)..(37)
<223> OTHER INFORMATION: n is BzdU.
<220> FEATURE:
<221> NAME/KEY: misc_feature
<222> LOCATION: (40)..(40)
<223> OTHER INFORMATION: S is Gemcitabine.
<220> FEATURE:
<221> NAME/KEY: misc_feature
<222> LOCATION: (41)..(41)
<223> OTHER INFORMATION: S is Gemcitabine.

<400> SEQUENCE: 2
gggaagngaa ngcgnngaan nangncccnn cagncancas sa                          42

<210> SEQ ID NO 3
<211> LENGTH: 40
<212> TYPE: DNA
<213> ORGANISM: Artificial Sequence
<220> FEATURE:
<223> OTHER INFORMATION: 12-10 G(2)L
<220> FEATURE:
<221> NAME/KEY: misc_feature
<222> LOCATION: (7)..(7)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (20)..(20)
<223> OTHER INFORMATION: n is BzdU.
<220> FEATURE:
<221> NAME/KEY: misc_feature
<222> LOCATION: (21)..(21)
<223> OTHER INFORMATION: n is BzdU.
<220> FEATURE:
<221> NAME/KEY: misc_feature
<222> LOCATION: (23)..(23)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (26)..(26)
```

```
<223> OTHER INFORMATION: S is Gemcitabine.
<220> FEATURE:
<221> NAME/KEY: misc_feature
<222> LOCATION: (27)..(27)
<223> OTHER INFORMATION: S is Gemcitabine.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (30)..(30)
<223> OTHER INFORMATION: n is BzdU.
<220> FEATURE:
<221> NAME/KEY: misc_feature
<222> LOCATION: (34)..(34)
<223> OTHER INFORMATION: n is BzdU.
<220> FEATURE:
<221> NAME/KEY: misc_feature
<222> LOCATION: (37)..(37)
<223> OTHER INFORMATION: n is BzdU.

<400> SEQUENCE: 3
gggaagngaa ngcgnngaan nangnsscnn cagncancac                           40

<210> SEQ ID NO 4
<211> LENGTH: 40
<212> TYPE: DNA
<213> ORGANISM: Artificial Sequence
<220> FEATURE:
<223> OTHER INFORMATION: 12-10 G(2)5'
<220> FEATURE:
<221> NAME/KEY: misc_feature
<222> LOCATION: (1)..(1)
<223> OTHER INFORMATION: S is Gemcitabine.
<220> FEATURE:
<221> NAME/KEY: misc_feature
<222> LOCATION: (2)..(2)
<223> OTHER INFORMATION: S is Gemcitabine.
<220> FEATURE:
<221> NAME/KEY: misc_feature
<222> LOCATION: (7)..(7)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (20)..(20)
<223> OTHER INFORMATION: n is BzdU.
<220> FEATURE:
<221> NAME/KEY: misc_feature
<222> LOCATION: (21)..(21)
<223> OTHER INFORMATION: n is BzdU.
<220> FEATURE:
<221> NAME/KEY: misc_feature
<222> LOCATION: (23)..(23)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
```

```
<222> LOCATION: (30)..(30)
<223> OTHER INFORMATION: n is BzdU.
<220> FEATURE:
<221> NAME/KEY: misc_feature
<222> LOCATION: (34)..(34)
<223> OTHER INFORMATION: n is BzdU.
<220> FEATURE:
<221> NAME/KEY: misc_feature
<222> LOCATION: (37)..(37)
<223> OTHER INFORMATION: n is BzdU.

<400> SEQUENCE: 4
ssgaagngaa ngcgnngaan nangncccnn cagncancac                          40

<210> SEQ ID NO 5
<211> LENGTH: 40
<212> TYPE: DNA
<213> ORGANISM: Artificial Sequence
<220> FEATURE:
<223> OTHER INFORMATION: 12-10 G(2)P
<220> FEATURE:
<221> NAME/KEY: misc_feature
<222> LOCATION: (7)..(7)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (20)..(20)
<223> OTHER INFORMATION: n is BzdU.
<220> FEATURE:
<221> NAME/KEY: misc_feature
<222> LOCATION: (21)..(21)
<223> OTHER INFORMATION: n is BzdU.
<220> FEATURE:
<221> NAME/KEY: misc_feature
<222> LOCATION: (23)..(23)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (30)..(30)
<223> OTHER INFORMATION: n is BzdU.
<220> FEATURE:
<221> NAME/KEY: misc_feature
<222> LOCATION: (34)..(34)
<223> OTHER INFORMATION: n is BzdU.
<220> FEATURE:
<221> NAME/KEY: misc_feature
<222> LOCATION: (35)..(35)
<223> OTHER INFORMATION: S is Gemcitabine.
<220> FEATURE:
<221> NAME/KEY: misc_feature
<222> LOCATION: (37)..(37)
<223> OTHER INFORMATION: n is BzdU.
<220> FEATURE:
<221> NAME/KEY: misc_feature
<222> LOCATION: (38)..(38)
<223> OTHER INFORMATION: S is Gemcitabine.
```

```
<400> SEQUENCE: 5
gggaagngaa ngcgnngaan nangncccnn cagnsansac                                40

<210> SEQ ID NO 6
<211> LENGTH: 35
<212> TYPE: DNA
<213> ORGANISM: Artificial Sequence
<220> FEATURE:
<223> OTHER INFORMATION: 12-12
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (20)..(20)
<223> OTHER INFORMATION: n is BzdU.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.

<400> SEQUENCE: 6
gngaangcgn ngaannangn cccnncagnc ancac                                35

<210> SEQ ID NO 7
<211> LENGTH: 35
<212> TYPE: DNA
<213> ORGANISM: Artificial Sequence
<220> FEATURE:
<223> OTHER INFORMATION: 12-12 G(3)
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (6)..(6)
<223> OTHER INFORMATION: n is BzdU.
```

-continued

```
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (20)..(20)
<223> OTHER INFORMATION: n is BzdU.
<220> FEATURE:
<221> NAME/KEY: misc_feature
<222> LOCATION: (21)..(21)
<223> OTHER INFORMATION: S is Gemcitabine.
<220> FEATURE:
<221> NAME/KEY: misc_feature
<222> LOCATION: (22)..(22)
<223> OTHER INFORMATION: S is Gemcitabine.
<220> FEATURE:
<221> NAME/KEY: misc_feature
<222> LOCATION: (23)..(23)
<223> OTHER INFORMATION: S is Gemcitabine.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.

<400> SEQUENCE: 7
gngaangcgn ngaannangn sssnncagnc ancac                                    35

<210> SEQ ID NO 8
<211> LENGTH: 35
<212> TYPE: DNA
<213> ORGANISM: Artificial Sequence
<220> FEATURE:
<223> OTHER INFORMATION: 12-12 G(5)
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (8)..(8)
<223> OTHER INFORMATION: S is Gemcitabine.
<220> FEATURE:
<221> NAME/KEY: misc_feature
<222> LOCATION: (10)..(10)
```

```
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (20)..(20)
<223> OTHER INFORMATION: n is BzdU.
<220> FEATURE:
<221> NAME/KEY: misc_feature
<222> LOCATION: (21)..(21)
<223> OTHER INFORMATION: S is Gemcitabine.
<220> FEATURE:
<221> NAME/KEY: misc_feature
<222> LOCATION: (22)..(22)
<223> OTHER INFORMATION: S is Gemcitabine.
<220> FEATURE:
<221> NAME/KEY: misc_feature
<222> LOCATION: (23)..(23)
<223> OTHER INFORMATION: S is Gemcitabine.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.
<220> FEATURE:
<221> NAME/KEY: misc_feature
<222> LOCATION: (35)..(35)
<223> OTHER INFORMATION: S is Gemcitabine.

<400> SEQUENCE: 8
gngaangsgn ngaannangn sssnncagnc ancas                                    35

<210> SEQ ID NO 9
<211> LENGTH: 35
<212> TYPE: DNA
<213> ORGANISM: Artificial Sequence
<220> FEATURE:
<223> OTHER INFORMATION: 12-12 G(7)
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (8)..(8)
<223> OTHER INFORMATION: S is Gemcitabine.
<220> FEATURE:
<221> NAME/KEY: misc_feature
```

```
<222> LOCATION: (9)..(9)
<223> OTHER INFORMATION: S is Gemcitabine.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (19)..(19)
<223> OTHER INFORMATION: S is Gemcitabine.
<220> FEATURE:
<221> NAME/KEY: misc_feature
<222> LOCATION: (20)..(20)
<223> OTHER INFORMATION: n is BzdU.
<220> FEATURE:
<221> NAME/KEY: misc_feature
<222> LOCATION: (21)..(21)
<223> OTHER INFORMATION: S is Gemcitabine.
<220> FEATURE:
<221> NAME/KEY: misc_feature
<222> LOCATION: (22)..(22)
<223> OTHER INFORMATION: S is Gemcitabine.
<220> FEATURE:
<221> NAME/KEY: misc_feature
<222> LOCATION: (23)..(23)
<223> OTHER INFORMATION: S is Gemcitabine.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.
<220> FEATURE:
<221> NAME/KEY: misc_feature
<222> LOCATION: (35)..(35)
<223> OTHER INFORMATION: S is Gemcitabine.

<400> SEQUENCE: 9
gngaangssn ngaannansn sssnncagnc ancas                                35

<210> SEQ ID NO 10
<211> LENGTH: 35
<212> TYPE: DNA
<213> ORGANISM: Artificial Sequence
<220> FEATURE:
<223> OTHER INFORMATION: Combi 1
<220> FEATURE:
<221> NAME/KEY: misc_feature
<222> LOCATION: (2)..(2)
<223> OTHER INFORMATION: n is BzdU.
<220> FEATURE:
```

```
<221> NAME/KEY: misc_feature
<222> LOCATION: (4)..(4)
<223> OTHER INFORMATION: A is 2-Fluorine-DNA.
<220> FEATURE:
<221> NAME/KEY: misc_feature
<222> LOCATION: (5)..(5)
<223> OTHER INFORMATION: A is 2-Fluorine-DNA.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (12)..(12)
<223> OTHER INFORMATION: G is 2-Fluorine-DNA.
<220> FEATURE:
<221> NAME/KEY: misc_feature
<222> LOCATION: (13)..(13)
<223> OTHER INFORMATION: A is 2-Fluorine-DNA.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (20)..(20)
<223> OTHER INFORMATION: n is BzdU.
<220> FEATURE:
<221> NAME/KEY: misc_feature
<222> LOCATION: (21)..(21)
<223> OTHER INFORMATION: G is 2-Fluorine-DNA.
<220> FEATURE:
<221> NAME/KEY: misc_feature
<222> LOCATION: (22)..(22)
<223> OTHER INFORMATION: G is 2-Fluorine-DNA.
<220> FEATURE:
<221> NAME/KEY: misc_feature
<222> LOCATION: (23)..(23)
<223> OTHER INFORMATION: G is 2-Fluorine-DNA.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.

<400> SEQUENCE: 10
gngaangcgn ngaannangn cccnncagnc ancac                               35

<210> SEQ ID NO 11
<211> LENGTH: 35
```

```
<212> TYPE: DNA
<213> ORGANISM: Artificial Sequence
<220> FEATURE:
<223> OTHER INFORMATION: Combi 2
<220> FEATURE:
<221> NAME/KEY: misc_feature
<222> LOCATION: (1)..(1)
<223> OTHER INFORMATION: G is 2-O-Methoxy-DNA.
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (3)..(3)
<223> OTHER INFORMATION: G is 2-O-Methoxy-DNA.
<220> FEATURE:
<221> NAME/KEY: misc_feature
<222> LOCATION: (4)..(4)
<223> OTHER INFORMATION: A is 2-Fluorine-DNA.
<220> FEATURE:
<221> NAME/KEY: misc_feature
<222> LOCATION: (5)..(5)
<223> OTHER INFORMATION: A is 2-Fluorine-DNA.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (12)..(12)
<223> OTHER INFORMATION: G is 2-Fluorine-DNA.
<220> FEATURE:
<221> NAME/KEY: misc_feature
<222> LOCATION: (13)..(13)
<223> OTHER INFORMATION: A is 2-Fluorine-DNA.
<220> FEATURE:
<221> NAME/KEY: misc_feature
<222> LOCATION: (14)..(14)
<223> OTHER INFORMATION: A is 2-Fluorine-DNA.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (17)..(17)
<223> OTHER INFORMATION: A is 2-Fluorine-DNA.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (20)..(20)
<223> OTHER INFORMATION: Y is Nap-dU.
<220> FEATURE:
<221> NAME/KEY: misc_feature
<222> LOCATION: (21)..(21)
<223> OTHER INFORMATION: C is 2-Fluorine-DNA.
<220> FEATURE:
<221> NAME/KEY: misc_feature
<222> LOCATION: (22)..(22)
<223> OTHER INFORMATION: C is 2-Fluorine-DNA.
<220> FEATURE:
<221> NAME/KEY: misc_feature
<222> LOCATION: (23)..(23)
```

```
<223> OTHER INFORMATION: C is 2-Fluorine-DNA.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (28)..(28)
<223> OTHER INFORMATION: G is 2-O-Methoxy-DNA.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.
<220> FEATURE:
<221> NAME/KEY: misc_feature
<222> LOCATION: (33)..(33)
<223> OTHER INFORMATION: C is 2-O-Methoxy-DNA.
<220> FEATURE:
<221> NAME/KEY: misc_feature
<222> LOCATION: (34)..(34)
<223> OTHER INFORMATION: A is 2-O-Methoxy-DNA.
<220> FEATURE:
<221> NAME/KEY: misc_feature
<222> LOCATION: (35)..(35)
<223> OTHER INFORMATION: C is 2-Fluorine-DNA.

<400> SEQUENCE: 11
gngaangcgn ngaannangy cccnncagnc ancac                                   35

<210> SEQ ID NO 12
<211> LENGTH: 35
<212> TYPE: DNA
<213> ORGANISM: Artificial Sequence
<220> FEATURE:
<223> OTHER INFORMATION: Combi 3
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (4)..(4)
<223> OTHER INFORMATION: A is 2-Fluorine-DNA.
<220> FEATURE:
<221> NAME/KEY: misc_feature
<222> LOCATION: (5)..(5)
<223> OTHER INFORMATION: A is 2-Fluorine-DNA.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (12)..(12)
<223> OTHER INFORMATION: G is 2-Fluorine-DNA.
<220> FEATURE:
<221> NAME/KEY: misc_feature
<222> LOCATION: (13)..(13)
<223> OTHER INFORMATION: A is 2-Fluorine-DNA.
<220> FEATURE:
<221> NAME/KEY: misc_feature
```

```
<222> LOCATION: (14)..(14)
<223> OTHER INFORMATION: A is 2-O-Methoxy-DNA.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (17)..(17)
<223> OTHER INFORMATION: A is 2-O-Methoxy-DNA.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (19)..(19)
<223> OTHER INFORMATION: W is C3 linker-DNA.
<220> FEATURE:
<221> NAME/KEY: misc_feature
<222> LOCATION: (20)..(20)
<223> OTHER INFORMATION: n is BzdU.
<220> FEATURE:
<221> NAME/KEY: misc_feature
<222> LOCATION: (21)..(21)
<223> OTHER INFORMATION: C is 2-Fluorine-DNA.
<220> FEATURE:
<221> NAME/KEY: misc_feature
<222> LOCATION: (22)..(22)
<223> OTHER INFORMATION: C is 2-Fluorine-DNA.
<220> FEATURE:
<221> NAME/KEY: misc_feature
<222> LOCATION: (23)..(23)
<223> OTHER INFORMATION: C is 2-Fluorine-DNA.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (28)..(28)
<223> OTHER INFORMATION: G is 2-Fluorine-DNA.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.

<400> SEQUENCE: 12
gngaangcgn ngaannanwn cccnncagnc ancac                                35

<210> SEQ ID NO 13
<211> LENGTH: 35
<212> TYPE: DNA
<213> ORGANISM: Artificial Sequence
<220> FEATURE:
<223> OTHER INFORMATION: Combi 4
<220> FEATURE:
<221> NAME/KEY: misc_feature
<222> LOCATION: (1)..(1)
<223> OTHER INFORMATION: G is 2-O-Methoxy-DNA.
<220> FEATURE:
<221> NAME/KEY: misc_feature
<222> LOCATION: (2)..(2)
<223> OTHER INFORMATION: n is BzdU.
<220> FEATURE:
```

```
<221> NAME/KEY: misc_feature
<222> LOCATION: (3)..(3)
<223> OTHER INFORMATION: G is 2-O-Methoxy-DNA.
<220> FEATURE:
<221> NAME/KEY: misc_feature
<222> LOCATION: (4)..(4)
<223> OTHER INFORMATION: A is 2-Fluorine-DNA.
<220> FEATURE:
<221> NAME/KEY: misc_feature
<222> LOCATION: (5)..(5)
<223> OTHER INFORMATION: A is 2-Fluorine-DNA.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (12)..(12)
<223> OTHER INFORMATION: G is 2-Fluorine-DNA.
<220> FEATURE:
<221> NAME/KEY: misc_feature
<222> LOCATION: (13)..(13)
<223> OTHER INFORMATION: A is 2-Fluorine-DNA.
<220> FEATURE:
<221> NAME/KEY: misc_feature
<222> LOCATION: (14)..(14)
<223> OTHER INFORMATION: A is 2-Fluorine-DNA.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (17)..(17)
<223> OTHER INFORMATION: A is 2-Fluorine-DNA.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (20)..(20)
<223> OTHER INFORMATION: Y is Nap-dU.
<220> FEATURE:
<221> NAME/KEY: misc_feature
<222> LOCATION: (21)..(21)
<223> OTHER INFORMATION: C is 2-Fluorine-DNA.
<220> FEATURE:
<221> NAME/KEY: misc_feature
<222> LOCATION: (22)..(22)
<223> OTHER INFORMATION: C is 2-Fluorine-DNA.
<220> FEATURE:
<221> NAME/KEY: misc_feature
<222> LOCATION: (23)..(23)
<223> OTHER INFORMATION: C is 2-Fluorine-DNA.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (28)..(28)
<223> OTHER INFORMATION: G is 2-O-Methoxy-DNA.
```

```
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.
<220> FEATURE:
<221> NAME/KEY: misc_feature
<222> LOCATION: (33)..(33)
<223> OTHER INFORMATION: C is 2-Fluorine-DNA.
<220> FEATURE:
<221> NAME/KEY: misc_feature
<222> LOCATION: (34)..(34)
<223> OTHER INFORMATION: A is 2-O-Methoxy-DNA.
<220> FEATURE:
<221> NAME/KEY: misc_feature
<222> LOCATION: (35)..(35)
<223> OTHER INFORMATION: C is 2-Fluorine-DNA.

<400> SEQUENCE: 13
gngaangcgn ngaannangy cccnncagnc ancac                                          35

<210> SEQ ID NO 14
<211> LENGTH: 35
<212> TYPE: DNA
<213> ORGANISM: Artificial Sequence
<220> FEATURE:
<223> OTHER INFORMATION: Combi 5
<220> FEATURE:
<221> NAME/KEY: misc_feature
<222> LOCATION: (1)..(1)
<223> OTHER INFORMATION: G is 2-O-Methoxy-DNA.
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (3)..(3)
<223> OTHER INFORMATION: G is 2-O-Methoxy-DNA.
<220> FEATURE:
<221> NAME/KEY: misc_feature
<222> LOCATION: (4)..(4)
<223> OTHER INFORMATION: A is 2-Fluorine-DNA.
<220> FEATURE:
<221> NAME/KEY: misc_feature
<222> LOCATION: (5)..(5)
<223> OTHER INFORMATION: A is 2-Fluorine-DNA.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (12)..(12)
<223> OTHER INFORMATION: G is 2-Fluorine-DNA.
<220> FEATURE:
<221> NAME/KEY: misc_feature
<222> LOCATION: (13)..(13)
<223> OTHER INFORMATION: A is 2-Fluorine-DNA.
<220> FEATURE:
<221> NAME/KEY: misc_feature
<222> LOCATION: (14)..(14)
<223> OTHER INFORMATION: A is 2-O-Methoxy-DNA.
<220> FEATURE:
<221> NAME/KEY: misc_feature
<222> LOCATION: (15)..(15)
```

-continued

```
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (17)..(17)
<223> OTHER INFORMATION: A is 2-O-Methoxy-DNA.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (19)..(19)
<223> OTHER INFORMATION: W is C3 linker-DNA.
<220> FEATURE:
<221> NAME/KEY: misc_feature
<222> LOCATION: (20)..(20)
<223> OTHER INFORMATION: Y is Nap-dU.
<220> FEATURE:
<221> NAME/KEY: misc_feature
<222> LOCATION: (21)..(21)
<223> OTHER INFORMATION: C is 2-Fluorine-DNA.
<220> FEATURE:
<221> NAME/KEY: misc_feature
<222> LOCATION: (22)..(22)
<223> OTHER INFORMATION: C is 2-Fluorine-DNA.
<220> FEATURE:
<221> NAME/KEY: misc_feature
<222> LOCATION: (23)..(23)
<223> OTHER INFORMATION: C is 2-Fluorine-DNA.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (28)..(28)
<223> OTHER INFORMATION: G is 2-O-Methoxy-DNA.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.
<220> FEATURE:
<221> NAME/KEY: misc_feature
<222> LOCATION: (33)..(33)
<223> OTHER INFORMATION: C is 2-Fluorine-DNA.
<220> FEATURE:
<221> NAME/KEY: misc_feature
<222> LOCATION: (34)..(34)
<223> OTHER INFORMATION: A is 2-O-Methoxy-DNA.
<220> FEATURE:
<221> NAME/KEY: misc_feature
<222> LOCATION: (35)..(35)
<223> OTHER INFORMATION: C is 2-Fluorine-DNA.

<400> SEQUENCE: 14
gngaangcgn ngaannanwy cccnncagnc ancac                                35

<210> SEQ ID NO 15
<211> LENGTH: 35
<212> TYPE: DNA
<213> ORGANISM: Artificial Sequence
<220> FEATURE:
<223> OTHER INFORMATION: Combi 6
<220> FEATURE:
<221> NAME/KEY: misc_feature
```

-continued

```
<222> LOCATION: (1)..(1)
<223> OTHER INFORMATION: G is 2-O-Methoxy-DNA.
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (3)..(3)
<223> OTHER INFORMATION: G is 2-O-Methoxy-DNA.
<220> FEATURE:
<221> NAME/KEY: misc_feature
<222> LOCATION: (4)..(4)
<223> OTHER INFORMATION: A is 2-Fluorine-DNA.
<220> FEATURE:
<221> NAME/KEY: misc_feature
<222> LOCATION: (5)..(5)
<223> OTHER INFORMATION: A is 2-Fluorine-DNA.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (12)..(12)
<223> OTHER INFORMATION: G is 2-Fluorine-DNA.
<220> FEATURE:
<221> NAME/KEY: misc_feature
<222> LOCATION: (13)..(13)
<223> OTHER INFORMATION: A is 2-Fluorine-DNA.
<220> FEATURE:
<221> NAME/KEY: misc_feature
<222> LOCATION: (14)..(14)
<223> OTHER INFORMATION: A is 2-O-Methoxy-DNA.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (17)..(17)
<223> OTHER INFORMATION: A is 2-O-Methoxy-DNA.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (20)..(20)
<223> OTHER INFORMATION: Y is Nap-dU.
<220> FEATURE:
<221> NAME/KEY: misc_feature
<222> LOCATION: (21)..(21)
<223> OTHER INFORMATION: C is 2-Fluorine-DNA.
<220> FEATURE:
<221> NAME/KEY: misc_feature
<222> LOCATION: (22)..(22)
<223> OTHER INFORMATION: C is 2-Fluorine-DNA.
<220> FEATURE:
<221> NAME/KEY: misc_feature
<222> LOCATION: (23)..(23)
<223> OTHER INFORMATION: C is 2-Fluorine-DNA.
<220> FEATURE:
<221> NAME/KEY: misc_feature
<222> LOCATION: (24)..(24)
<223> OTHER INFORMATION: n is BzdU.
<220> FEATURE:
```

```
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (28)..(28)
<223> OTHER INFORMATION: G is 2-O-Methoxy-DNA.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.
<220> FEATURE:
<221> NAME/KEY: misc_feature
<222> LOCATION: (33)..(33)
<223> OTHER INFORMATION: C is 2-Fluorine-DNA.
<220> FEATURE:
<221> NAME/KEY: misc_feature
<222> LOCATION: (34)..(34)
<223> OTHER INFORMATION: A is 2-O-Methoxy-DNA.
<220> FEATURE:
<221> NAME/KEY: misc_feature
<222> LOCATION: (35)..(35)
<223> OTHER INFORMATION: C is 2-Fluorine-DNA.

<400> SEQUENCE: 15
gngaangcgn ngaannangy cccnncagnc ancac                                          35

<210> SEQ ID NO 16
<211> LENGTH: 35
<212> TYPE: DNA
<213> ORGANISM: Artificial Sequence
<220> FEATURE:
<223> OTHER INFORMATION: Combi 7
<220> FEATURE:
<221> NAME/KEY: misc_feature
<222> LOCATION: (1)..(1)
<223> OTHER INFORMATION: G is 2-O-Methoxy-DNA.
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (3)..(3)
<223> OTHER INFORMATION: G is 2-O-Methoxy-DNA.
<220> FEATURE:
<221> NAME/KEY: misc_feature
<222> LOCATION: (4)..(4)
<223> OTHER INFORMATION: A is 2-Fluorine-DNA.
<220> FEATURE:
<221> NAME/KEY: misc_feature
<222> LOCATION: (5)..(5)
<223> OTHER INFORMATION: A is 2-Fluorine-DNA.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (12)..(12)
<223> OTHER INFORMATION: G is 2-Fluorine-DNA.
<220> FEATURE:
<221> NAME/KEY: misc_feature
<222> LOCATION: (13)..(13)
<223> OTHER INFORMATION: A is 2-Fluorine-DNA.
```

```
<220> FEATURE:
<221> NAME/KEY: misc_feature
<222> LOCATION: (14)..(14)
<223> OTHER INFORMATION: A is 2-O-Methoxy-DNA.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (17)..(17)
<223> OTHER INFORMATION: A is 2-O-Methoxy-DNA.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (20)..(20)
<223> OTHER INFORMATION: n is BzdU.
<220> FEATURE:
<221> NAME/KEY: misc_feature
<222> LOCATION: (21)..(21)
<223> OTHER INFORMATION: C is 2-Fluorine-DNA.
<220> FEATURE:
<221> NAME/KEY: misc_feature
<222> LOCATION: (22)..(22)
<223> OTHER INFORMATION: C is 2-Fluorine-DNA.
<220> FEATURE:
<221> NAME/KEY: misc_feature
<222> LOCATION: (23)..(23)
<223> OTHER INFORMATION: C is 2-Fluorine-DNA.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (28)..(28)
<223> OTHER INFORMATION: G is 2-O-Methoxy-DNA.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.
<220> FEATURE:
<221> NAME/KEY: misc_feature
<222> LOCATION: (33)..(33)
<223> OTHER INFORMATION: C is 2-Fluorine-DNA.
<220> FEATURE:
<221> NAME/KEY: misc_feature
<222> LOCATION: (34)..(34)
<223> OTHER INFORMATION: A is 2-O-Methoxy-DNA.
<220> FEATURE:
<221> NAME/KEY: misc_feature
<222> LOCATION: (35)..(35)
<223> OTHER INFORMATION: C is 2-Fluorine-DNA.

<400> SEQUENCE: 16
gngaangcgn ngaannangn cccnncagnc ancac                                35

<210> SEQ ID NO 17
<211> LENGTH: 35
<212> TYPE: DNA
<213> ORGANISM: Artificial Sequence
<220> FEATURE:
```

```
<223> OTHER INFORMATION: Combi 8
<220> FEATURE:
<221> NAME/KEY: misc_feature
<222> LOCATION: (1)..(1)
<223> OTHER INFORMATION: G is 2-O-Methoxy-DNA.
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (3)..(3)
<223> OTHER INFORMATION: G is 2-O-Methoxy-DNA.
<220> FEATURE:
<221> NAME/KEY: misc_feature
<222> LOCATION: (4)..(4)
<223> OTHER INFORMATION: A is 2-Fluorine-DNA.
<220> FEATURE:
<221> NAME/KEY: misc_feature
<222> LOCATION: (5)..(5)
<223> OTHER INFORMATION: A is 2-Fluorine-DNA.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (12)..(12)
<223> OTHER INFORMATION: G is 2-Fluorine-DNA.
<220> FEATURE:
<221> NAME/KEY: misc_feature
<222> LOCATION: (13)..(13)
<223> OTHER INFORMATION: A is 2-Fluorine-DNA.
<220> FEATURE:
<221> NAME/KEY: misc_feature
<222> LOCATION: (14)..(14)
<223> OTHER INFORMATION: A is 2-O-Methoxy-DNA.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (17)..(17)
<223> OTHER INFORMATION: A is 2-O-Methoxy-DNA.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (19)..(19)
<223> OTHER INFORMATION: W is C3 linker-DNA.
<220> FEATURE:
<221> NAME/KEY: misc_feature
<222> LOCATION: (20)..(20)
<223> OTHER INFORMATION: n is BzdU.
<220> FEATURE:
<221> NAME/KEY: misc_feature
<222> LOCATION: (21)..(21)
<223> OTHER INFORMATION: C is 2-Fluorine-DNA.
<220> FEATURE:
<221> NAME/KEY: misc_feature
<222> LOCATION: (22)..(22)
<223> OTHER INFORMATION: C is 2-Fluorine-DNA.
<220> FEATURE:
<221> NAME/KEY: misc_feature
```

```
<222> LOCATION: (23)..(23)
<223> OTHER INFORMATION: C is 2-Fluorine-DNA.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (28)..(28)
<223> OTHER INFORMATION: G is 2-O-Methoxy-DNA.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.
<220> FEATURE:
<221> NAME/KEY: misc_feature
<222> LOCATION: (33)..(33)
<223> OTHER INFORMATION: C is 2-Fluorine-DNA.
<220> FEATURE:
<221> NAME/KEY: misc_feature
<222> LOCATION: (34)..(34)
<223> OTHER INFORMATION: A is 2-O-Methoxy-DNA.
<220> FEATURE:
<221> NAME/KEY: misc_feature
<222> LOCATION: (35)..(35)
<223> OTHER INFORMATION: C is 2-Fluorine-DNA.

<400> SEQUENCE: 17
gngaangcgn ngaannanwn cccnncagnc ancac                                    35

<210> SEQ ID NO 18
<211> LENGTH: 35
<212> TYPE: DNA
<213> ORGANISM: Artificial Sequence
<220> FEATURE:
<223> OTHER INFORMATION: Combi 9
<220> FEATURE:
<221> NAME/KEY: misc_feature
<222> LOCATION: (1)..(1)
<223> OTHER INFORMATION: G is 2-O-Methoxy-DNA.
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (3)..(3)
<223> OTHER INFORMATION: G is 2-O-Methoxy-DNA.
<220> FEATURE:
<221> NAME/KEY: misc_feature
<222> LOCATION: (4)..(4)
<223> OTHER INFORMATION: A is 2-Fluorine-DNA.
<220> FEATURE:
<221> NAME/KEY: misc_feature
<222> LOCATION: (5)..(5)
<223> OTHER INFORMATION: A is 2-Fluorine-DNA.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
```

```
<221> NAME/KEY: misc_feature
<222> LOCATION: (12)..(12)
<223> OTHER INFORMATION: G is 2-Fluorine-DNA.
<220> FEATURE:
<221> NAME/KEY: misc_feature
<222> LOCATION: (13)..(13)
<223> OTHER INFORMATION: A is 2-Fluorine-DNA.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (20)..(20)
<223> OTHER INFORMATION: n is BzdU.
<220> FEATURE:
<221> NAME/KEY: misc_feature
<222> LOCATION: (21)..(21)
<223> OTHER INFORMATION: C is 2-Fluorine-DNA.
<220> FEATURE:
<221> NAME/KEY: misc_feature
<222> LOCATION: (22)..(22)
<223> OTHER INFORMATION: C is 2-Fluorine-DNA.
<220> FEATURE:
<221> NAME/KEY: misc_feature
<222> LOCATION: (23)..(23)
<223> OTHER INFORMATION: C is 2-Fluorine-DNA.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (28)..(28)
<223> OTHER INFORMATION: G is 2-O-Methoxy-DNA.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.
<220> FEATURE:
<221> NAME/KEY: misc_feature
<222> LOCATION: (33)..(33)
<223> OTHER INFORMATION: C is 2-Fluorine-DNA.
<220> FEATURE:
<221> NAME/KEY: misc_feature
<222> LOCATION: (34)..(34)
<223> OTHER INFORMATION: A is 2-O-Methoxy-DNA.
<220> FEATURE:
<221> NAME/KEY: misc_feature
<222> LOCATION: (35)..(35)
<223> OTHER INFORMATION: G is 2-Fluorine-DNA.

<400> SEQUENCE: 18
gngaangcgn ngaannangn cccnncagnc ancac                                    35

<210> SEQ ID NO 19
<211> LENGTH: 35
<212> TYPE: DNA
<213> ORGANISM: Artificial Sequence
<220> FEATURE:
<223> OTHER INFORMATION: Combi 10
```

```
<220> FEATURE:
<221> NAME/KEY: misc_feature
<222> LOCATION: (1)..(1)
<223> OTHER INFORMATION: G is 2-O-Methoxy-DNA.
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (3)..(3)
<223> OTHER INFORMATION: G is 2-O-Methoxy-DNA.
<220> FEATURE:
<221> NAME/KEY: misc_feature
<222> LOCATION: (4)..(4)
<223> OTHER INFORMATION: A is 2-Fluorine-DNA.
<220> FEATURE:
<221> NAME/KEY: misc_feature
<222> LOCATION: (5)..(5)
<223> OTHER INFORMATION: A is 2-Fluorine-DNA.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (12)..(12)
<223> OTHER INFORMATION: G is 2-Fluorine-DNA.
<220> FEATURE:
<221> NAME/KEY: misc_feature
<222> LOCATION: (13)..(13)
<223> OTHER INFORMATION: A is 2-Fluorine-DNA.
<220> FEATURE:
<221> NAME/KEY: misc_feature
<222> LOCATION: (14)..(14)
<223> OTHER INFORMATION: A is 2-Fluorine-DNA.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (17)..(17)
<223> OTHER INFORMATION: A is 2-Fluorine-DNA.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (20)..(20)
<223> OTHER INFORMATION: n is BzdU.
<220> FEATURE:
<221> NAME/KEY: misc_feature
<222> LOCATION: (21)..(21)
<223> OTHER INFORMATION: C is 2-Fluorine-DNA.
<220> FEATURE:
<221> NAME/KEY: misc_feature
<222> LOCATION: (22)..(22)
<223> OTHER INFORMATION: C is 2-Fluorine-DNA.
<220> FEATURE:
<221> NAME/KEY: misc_feature
<222> LOCATION: (23)..(23)
<223> OTHER INFORMATION: C is 2-Fluorine-DNA.
<220> FEATURE:
<221> NAME/KEY: misc_feature
<222> LOCATION: (24)..(24)
```

```
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (28)..(28)
<223> OTHER INFORMATION: G is 2-O-Methoxy-DNA.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.
<220> FEATURE:
<221> NAME/KEY: misc_feature
<222> LOCATION: (33)..(33)
<223> OTHER INFORMATION: C is 2-Fluorine-DNA.
<220> FEATURE:
<221> NAME/KEY: misc_feature
<222> LOCATION: (34)..(34)
<223> OTHER INFORMATION: A is 2-O-Methoxy-DNA.
<220> FEATURE:
<221> NAME/KEY: misc_feature
<222> LOCATION: (35)..(35)
<223> OTHER INFORMATION: C is 2-Fluorine-DNA.

<400> SEQUENCE: 19
gngaangcgn ngaannangn cccnncagnc ancac                                      35

<210> SEQ ID NO 20
<211> LENGTH: 35
<212> TYPE: DNA
<213> ORGANISM: Artificial Sequence
<220> FEATURE:
<223> OTHER INFORMATION: Combi 11 G(3)
<220> FEATURE:
<221> NAME/KEY: misc_feature
<222> LOCATION: (1)..(1)
<223> OTHER INFORMATION: G is 2-Methoxyethyl-DNA.
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (3)..(3)
<223> OTHER INFORMATION: G is 2-Methoxyethyl-DNA.
<220> FEATURE:
<221> NAME/KEY: misc_feature
<222> LOCATION: (4)..(4)
<223> OTHER INFORMATION: A is 2-Fluorine-DNA.
<220> FEATURE:
<221> NAME/KEY: misc_feature
<222> LOCATION: (5)..(5)
<223> OTHER INFORMATION: A is 2-Fluorine-DNA.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (12)..(12)
<223> OTHER INFORMATION: G is 2-Fluorine-DNA.
<220> FEATURE:
<221> NAME/KEY: misc_feature
```

<222> LOCATION: (13)..(13)
<223> OTHER INFORMATION: A is 2-Fluorine-DNA.
<220> FEATURE:
<221> NAME/KEY: misc_feature
<222> LOCATION: (14)..(14)
<223> OTHER INFORMATION: A is 2-Methoxyethyl-DNA.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (17)..(17)
<223> OTHER INFORMATION: A is 2-Methoxyethyl-DNA.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (19)..(19)
<223> OTHER INFORMATION: W is C3 linker-DNA.
<220> FEATURE:
<221> NAME/KEY: misc_feature
<222> LOCATION: (20)..(20)
<223> OTHER INFORMATION: Y is Nap-dU.
<220> FEATURE:
<221> NAME/KEY: misc_feature
<222> LOCATION: (21)..(21)
<223> OTHER INFORMATION: S is Gemcitabine.
<220> FEATURE:
<221> NAME/KEY: misc_feature
<222> LOCATION: (22)..(22)
<223> OTHER INFORMATION: S is Gemcitabine.
<220> FEATURE:
<221> NAME/KEY: misc_feature
<222> LOCATION: (23)..(23)
<223> OTHER INFORMATION: S is Gemcitabine.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (28)..(28)
<223> OTHER INFORMATION: G is 2-Methoxyethyl-DNA.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.
<220> FEATURE:
<221> NAME/KEY: misc_feature
<222> LOCATION: (33)..(33)
<223> OTHER INFORMATION: C is 2-Fluorine-DNA.
<220> FEATURE:
<221> NAME/KEY: misc_feature
<222> LOCATION: (34)..(34)
<223> OTHER INFORMATION: A is 2-Methoxyethyl-DNA.
<220> FEATURE:
<221> NAME/KEY: misc_feature
<222> LOCATION: (35)..(35)
<223> OTHER INFORMATION: C is 2-Fluorine-DNA.

<400> SEQUENCE: 20
gngaangcgn ngaannanwy sssnncagnc ancac                               35

-continued

```
<210> SEQ ID NO 21
<211> LENGTH: 35
<212> TYPE: DNA
<213> ORGANISM: Artificial Sequence
<220> FEATURE:
<223> OTHER INFORMATION: Combi 4 G(3)
<220> FEATURE:
<221> NAME/KEY: misc_feature
<222> LOCATION: (1)..(1)
<223> OTHER INFORMATION: G is 2-O-Methoxy-DNA.
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (3)..(3)
<223> OTHER INFORMATION: G is 2-O-Methoxy-DNA.
<220> FEATURE:
<221> NAME/KEY: misc_feature
<222> LOCATION: (4)..(4)
<223> OTHER INFORMATION: A is 2-Fluorine-DNA.
<220> FEATURE:
<221> NAME/KEY: misc_feature
<222> LOCATION: (5)..(5)
<223> OTHER INFORMATION: A is 2-Fluorine-DNA.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (12)..(12)
<223> OTHER INFORMATION: G is 2-Fluorine-DNA.
<220> FEATURE:
<221> NAME/KEY: misc_feature
<222> LOCATION: (13)..(13)
<223> OTHER INFORMATION: A is 2-Fluorine-DNA.
<220> FEATURE:
<221> NAME/KEY: misc_feature
<222> LOCATION: (14)..(14)
<223> OTHER INFORMATION: A is 2-Fluorine-DNA.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (17)..(17)
<223> OTHER INFORMATION: A is 2-Fluorine-DNA.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (20)..(20)
<223> OTHER INFORMATION: Y is Nap-dU.
<220> FEATURE:
<221> NAME/KEY: misc_feature
<222> LOCATION: (21)..(21)
<223> OTHER INFORMATION: S is Gemcitabine.
<220> FEATURE:
<221> NAME/KEY: misc_feature
<222> LOCATION: (22)..(22)
<223> OTHER INFORMATION: S is Gemcitabine.
```

-continued

```
<220> FEATURE:
<221> NAME/KEY: misc_feature
<222> LOCATION: (23)..(23)
<223> OTHER INFORMATION: S is Gemcitabine.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (28)..(28)
<223> OTHER INFORMATION: G is 2-O-Methoxy-DNA.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.
<220> FEATURE:
<221> NAME/KEY: misc_feature
<222> LOCATION: (33)..(33)
<223> OTHER INFORMATION: C is 2-Fluorine-DNA.
<220> FEATURE:
<221> NAME/KEY: misc_feature
<222> LOCATION: (34)..(34)
<223> OTHER INFORMATION: A is 2-O-Methoxy-DNA.
<220> FEATURE:
<221> NAME/KEY: misc_feature
<222> LOCATION: (35)..(35)
<223> OTHER INFORMATION: C is 2-Fluorine-DNA.

<400> SEQUENCE: 21
gngaangcgn ngaannangy sssnncagnc ancac                              35

<210> SEQ ID NO 22
<211> LENGTH: 35
<212> TYPE: DNA
<213> ORGANISM: Artificial Sequence
<220> FEATURE:
<223> OTHER INFORMATION: Combi 5 G(3)
<220> FEATURE:
<221> NAME/KEY: misc_feature
<222> LOCATION: (1)..(1)
<223> OTHER INFORMATION: G is 2-O-Methoxy-DNA.
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (3)..(3)
<223> OTHER INFORMATION: G is 2-O-Methoxy-DNA.
<220> FEATURE:
<221> NAME/KEY: misc_feature
<222> LOCATION: (4)..(4)
<223> OTHER INFORMATION: A is 2-Fluorine-DNA.
<220> FEATURE:
<221> NAME/KEY: misc_feature
<222> LOCATION: (5)..(5)
<223> OTHER INFORMATION: A is 2-Fluorine-DNA.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
```

```
<223> OTHER INFORMATION: n is BzdU.
<220> FEATURE:
<221> NAME/KEY: misc_feature
<222> LOCATION: (12)..(12)
<223> OTHER INFORMATION: G is 2-Fluorine-DNA.
<220> FEATURE:
<221> NAME/KEY: misc_feature
<222> LOCATION: (13)..(13)
<223> OTHER INFORMATION: A is 2-Fluorine-DNA.
<220> FEATURE:
<221> NAME/KEY: misc_feature
<222> LOCATION: (14)..(14)
<223> OTHER INFORMATION: A is 2-O-Methoxy-DNA.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (17)..(17)
<223> OTHER INFORMATION: A is 2-O-Methoxy-DNA.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (19)..(19)
<223> OTHER INFORMATION: W is C3 linker-DNA.
<220> FEATURE:
<221> NAME/KEY: misc_feature
<222> LOCATION: (20)..(20)
<223> OTHER INFORMATION: Y is Nap-dU.
<220> FEATURE:
<221> NAME/KEY: misc_feature
<222> LOCATION: (21)..(21)
<223> OTHER INFORMATION: S is Gemcitabine.
<220> FEATURE:
<221> NAME/KEY: misc_feature
<222> LOCATION: (22)..(22)
<223> OTHER INFORMATION: S is Gemcitabine.
<220> FEATURE:
<221> NAME/KEY: misc_feature
<222> LOCATION: (23)..(23)
<223> OTHER INFORMATION: S is Gemcitabine.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (28)..(28)
<223> OTHER INFORMATION: G is 2-O-Methoxy-DNA.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.
<220> FEATURE:
<221> NAME/KEY: misc_feature
<222> LOCATION: (33)..(33)
<223> OTHER INFORMATION: C is 2-Fluorine-DNA.
<220> FEATURE:
<221> NAME/KEY: misc_feature
<222> LOCATION: (34)..(34)
<223> OTHER INFORMATION: A is 2-O-Methoxy-DNA.
<220> FEATURE:
<221> NAME/KEY: misc_feature
```

<222> LOCATION: (35)..(35)
<223> OTHER INFORMATION: C is 2-Fluorine-DNA.

<400> SEQUENCE: 22
gngaangcgn ngaannanwy sssnncagnc ancac                                        35

<210> SEQ ID NO 23
<211> LENGTH: 35
<212> TYPE: DNA
<213> ORGANISM: Artificial Sequence
<220> FEATURE:
<223> OTHER INFORMATION: Combi 8 G(3)
<220> FEATURE:
<221> NAME/KEY: misc_feature
<222> LOCATION: (1)..(1)
<223> OTHER INFORMATION: G is 2-O-Methoxy-DNA.
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (3)..(3)
<223> OTHER INFORMATION: G is 2-O-Methoxy-DNA.
<220> FEATURE:
<221> NAME/KEY: misc_feature
<222> LOCATION: (4)..(4)
<223> OTHER INFORMATION: A is 2-Fluorine-DNA.
<220> FEATURE:
<221> NAME/KEY: misc_feature
<222> LOCATION: (5)..(5)
<223> OTHER INFORMATION: A is 2-Fluorine-DNA.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (12)..(12)
<223> OTHER INFORMATION: G is 2-Fluorine-DNA.
<220> FEATURE:
<221> NAME/KEY: misc_feature
<222> LOCATION: (13)..(13)
<223> OTHER INFORMATION: A is 2-Fluorine-DNA.
<220> FEATURE:
<221> NAME/KEY: misc_feature
<222> LOCATION: (14)..(14)
<223> OTHER INFORMATION: A is 2-O-Methoxy-DNA.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (17)..(17)
<223> OTHER INFORMATION: A is 2-O-Methoxy-DNA.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (19)..(19)
<223> OTHER INFORMATION: W is C3 linker-DNA.
<220> FEATURE:

```
<221> NAME/KEY: misc_feature
<222> LOCATION: (20)..(20)
<223> OTHER INFORMATION: n is BzdU.
<220> FEATURE:
<221> NAME/KEY: misc_feature
<222> LOCATION: (21)..(21)
<223> OTHER INFORMATION: S is Gemcitabine.
<220> FEATURE:
<221> NAME/KEY: misc_feature
<222> LOCATION: (22)..(22)
<223> OTHER INFORMATION: S is Gemcitabine.
<220> FEATURE:
<221> NAME/KEY: misc_feature
<222> LOCATION: (23)..(23)
<223> OTHER INFORMATION: S is Gemcitabine.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (28)..(28)
<223> OTHER INFORMATION: G is 2-O-Methoxy-DNA.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.
<220> FEATURE:
<221> NAME/KEY: misc_feature
<222> LOCATION: (33)..(33)
<223> OTHER INFORMATION: C is 2-Fluorine-DNA.
<220> FEATURE:
<221> NAME/KEY: misc_feature
<222> LOCATION: (34)..(34)
<223> OTHER INFORMATION: A is 2-O-Methoxy-DNA.
<220> FEATURE:
<221> NAME/KEY: misc_feature
<222> LOCATION: (35)..(35)
<223> OTHER INFORMATION: C is 2-Fluorine-DNA.

<400> SEQUENCE: 23
gngaangcgn ngaannanwn sssnncagnc ancac                                 35

<210> SEQ ID NO 24
<211> LENGTH: 35
<212> TYPE: DNA
<213> ORGANISM: Artificial Sequence
<220> FEATURE:
<223> OTHER INFORMATION: Combi 4 G(5)
<220> FEATURE:
<221> NAME/KEY: misc_feature
<222> LOCATION: (1)..(1)
<223> OTHER INFORMATION: G is 2-O-Methoxy-DNA.
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (3)..(3)
<223> OTHER INFORMATION: G is 2-O-Methoxy-DNA.
<220> FEATURE:
<221> NAME/KEY: misc_feature
<222> LOCATION: (4)..(4)
<223> OTHER INFORMATION: A is 2-Fluorine-DNA.
<220> FEATURE:
<221> NAME/KEY: misc_feature
<222> LOCATION: (5)..(5)
<223> OTHER INFORMATION: A is 2-Fluorine-DNA.
```

```
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (12)..(12)
<223> OTHER INFORMATION: G is 2-Fluorine-DNA.
<220> FEATURE:
<221> NAME/KEY: misc_feature
<222> LOCATION: (13)..(13)
<223> OTHER INFORMATION: A is 2-Fluorine-DNA.
<220> FEATURE:
<221> NAME/KEY: misc_feature
<222> LOCATION: (14)..(14)
<223> OTHER INFORMATION: A is 2-Fluorine-DNA.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (17)..(17)
<223> OTHER INFORMATION: A is 2-Fluorine-DNA.
<220> FEATURE:
<221> NAME/KEY: misc_feature
<222> LOCATION: (18)..(18)
<223> OTHER INFORMATION: n is BzdU.
<220> FEATURE:
<221> NAME/KEY: misc_feature
<222> LOCATION: (20)..(20)
<223> OTHER INFORMATION: Y is Nap-dU.
<220> FEATURE:
<221> NAME/KEY: misc_feature
<222> LOCATION: (21)..(21)
<223> OTHER INFORMATION: S is Gemcitabine.
<220> FEATURE:
<221> NAME/KEY: misc_feature
<222> LOCATION: (22)..(22)
<223> OTHER INFORMATION: S is Gemcitabine.
<220> FEATURE:
<221> NAME/KEY: misc_feature
<222> LOCATION: (23)..(23)
<223> OTHER INFORMATION: S is Gemcitabine.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (28)..(28)
<223> OTHER INFORMATION: G is 2-O-Methoxy-DNA.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.
<220> FEATURE:
<221> NAME/KEY: misc_feature
<222> LOCATION: (33)..(33)
```

```
<223> OTHER INFORMATION: S is Gemcitabine.
<220> FEATURE:
<221> NAME/KEY: misc_feature
<222> LOCATION: (34)..(34)
<223> OTHER INFORMATION: A is 2-O-Methoxy-DNA.
<220> FEATURE:
<221> NAME/KEY: misc_feature
<222> LOCATION: (35)..(35)
<223> OTHER INFORMATION: S is Gemcitabine.

<400> SEQUENCE: 24
gngaangcgn ngaannangy sssnncagnc ansas                                    35

<210> SEQ ID NO 25
<211> LENGTH: 35
<212> TYPE: DNA
<213> ORGANISM: Artificial Sequence
<220> FEATURE:
<223> OTHER INFORMATION: Combi 5 G(5)
<220> FEATURE:
<221> NAME/KEY: misc_feature
<222> LOCATION: (1)..(1)
<223> OTHER INFORMATION: G is 2-O-Methoxy-DNA.
<220> FEATURE:
<221> NAME/KEY: misc_feature
<222> LOCATION: (2)..(2)
<223> OTHER INFORMATION: n is BzdU.
<220> FEATURE:
<221> NAME/KEY: misc_feature
<222> LOCATION: (3)..(3)
<223> OTHER INFORMATION: G is 2-O-Methoxy-DNA.
<220> FEATURE:
<221> NAME/KEY: misc_feature
<222> LOCATION: (4)..(4)
<223> OTHER INFORMATION: A is 2-Fluorine-DNA.
<220> FEATURE:
<221> NAME/KEY: misc_feature
<222> LOCATION: (5)..(5)
<223> OTHER INFORMATION: A is 2-Fluorine-DNA.
<220> FEATURE:
<221> NAME/KEY: misc_feature
<222> LOCATION: (6)..(6)
<223> OTHER INFORMATION: n is BzdU.
<220> FEATURE:
<221> NAME/KEY: misc_feature
<222> LOCATION: (10)..(10)
<223> OTHER INFORMATION: n is BzdU.
<220> FEATURE:
<221> NAME/KEY: misc_feature
<222> LOCATION: (11)..(11)
<223> OTHER INFORMATION: n is BzdU.
<220> FEATURE:
<221> NAME/KEY: misc_feature
<222> LOCATION: (12)..(12)
<223> OTHER INFORMATION: G is 2-Fluorine-DNA.
<220> FEATURE:
<221> NAME/KEY: misc_feature
<222> LOCATION: (13)..(13)
<223> OTHER INFORMATION: A is 2-Fluorine-DNA.
<220> FEATURE:
<221> NAME/KEY: misc_feature
<222> LOCATION: (14)..(14)
<223> OTHER INFORMATION: A is 2-O-Methoxy-DNA.
<220> FEATURE:
<221> NAME/KEY: misc_feature
<222> LOCATION: (15)..(15)
<223> OTHER INFORMATION: n is BzdU.
<220> FEATURE:
<221> NAME/KEY: misc_feature
<222> LOCATION: (16)..(16)
<223> OTHER INFORMATION: n is BzdU.
<220> FEATURE:
<221> NAME/KEY: misc_feature
<222> LOCATION: (17)..(17)
<223> OTHER INFORMATION: A is 2-O-Methoxy-DNA.
<220> FEATURE:
<221> NAME/KEY: misc_feature
```

-continued

```
<222> LOCATION: (18)..(18)
<223> OTHER INFORMATION: n is BzdU.
<220> FEATURE:
<221> NAME/KEY: misc_feature
<222> LOCATION: (19)..(19)
<223> OTHER INFORMATION: W is C3 linker-DNA.
<220> FEATURE:
<221> NAME/KEY: misc_feature
<222> LOCATION: (20)..(20)
<223> OTHER INFORMATION: Y is Nap-dU.
<220> FEATURE:
<221> NAME/KEY: misc_feature
<222> LOCATION: (21)..(21)
<223> OTHER INFORMATION: S is Gemcitabine.
<220> FEATURE:
<221> NAME/KEY: misc_feature
<222> LOCATION: (22)..(22)
<223> OTHER INFORMATION: S is Gemcitabine.
<220> FEATURE:
<221> NAME/KEY: misc_feature
<222> LOCATION: (23)..(23)
<223> OTHER INFORMATION: S is Gemcitabine.
<220> FEATURE:
<221> NAME/KEY: misc_feature
<222> LOCATION: (24)..(24)
<223> OTHER INFORMATION: n is BzdU.
<220> FEATURE:
<221> NAME/KEY: misc_feature
<222> LOCATION: (25)..(25)
<223> OTHER INFORMATION: n is BzdU.
<220> FEATURE:
<221> NAME/KEY: misc_feature
<222> LOCATION: (28)..(28)
<223> OTHER INFORMATION: G is 2-O-Methoxy-DNA.
<220> FEATURE:
<221> NAME/KEY: misc_feature
<222> LOCATION: (29)..(29)
<223> OTHER INFORMATION: n is BzdU.
<220> FEATURE:
<221> NAME/KEY: misc_feature
<222> LOCATION: (32)..(32)
<223> OTHER INFORMATION: n is BzdU.
<220> FEATURE:
<221> NAME/KEY: misc_feature
<222> LOCATION: (33)..(33)
<223> OTHER INFORMATION: S is Gemcitabine.
<220> FEATURE:
<221> NAME/KEY: misc_feature
<222> LOCATION: (34)..(34)
<223> OTHER INFORMATION: A is 2-O-Methoxy-DNA.
<220> FEATURE:
<221> NAME/KEY: misc_feature
<222> LOCATION: (35)..(35)
<223> OTHER INFORMATION: S is Gemcitabine.

<400> SEQUENCE: 25
gngaangcgn ngaannanwy sssnncagnc ansas                                        35
```

GLYPICAN-3-SPECIFIC MODIFIED APTAMER AND USE THEREOF

SEQUENCE LISTING SUBMISSION VIA EFS-WEB

A computer readable text file, entitled "SequenceListing.txt," created on Jun. 15, 2022 with a file size of 44,882 bytes contains the sequence listing for this application and is hereby incorporated by reference in its entirety.

TECHNICAL FIELD

The present invention relates to a glypican-3 (GPC3)-specific modified aptamer, and prevention or treatment of hepatoma using the same.

BACKGROUND ART

Hepatomas collectively refer to primary malignant tumors which primarily arise in the liver. Among these, the proportion of 'hepatocellular carcinoma' originating from hepatocytes is about 77%, the proportion of cholangiocarcinoma is 16%, and other carcinomas are rare, and thus hepatocellular carcinoma (HCC) accounts for most hepatomas. The main causes of hepatocellular carcinoma are chronic hepatitis B, chronic hepatitis C, cirrhosis, and alcoholic liver disease.

Since hepatoma is mostly treated without surgery or biopsy, it is not easy to obtain tissue samples. Clinical data to be considered, i.e., accompanied by chronic hepatitis or cirrhosis, are more than for other carcinomas, and thus clinical studies are not easy. For this reason, research on hepatoma has been relatively insufficient as compared with other carcinomas.

In addition, hepatoma is very difficult to treat due to its biological characteristics of being accompanied by chronic hepatitis and cirrhosis, which are associated diseases, and rapidly progressing by invading surrounding blood vessels in its early stages.

Treatment of hepatocellular carcinoma includes liver resection or liver trans-plantation, local treatment, transarterial chemoembolization and other transarterial therapies, radiation therapy, systemic therapy, etc. Systemic therapy is intended for patients who cannot be treated with local treatment due to non-liver metastases such as lymph node or lung metastases, and combination chemotherapy is mainly used for such patients. However, the objective response rate of chemotherapy is known to be less than 10%, and there is no evidence that chemotherapy will result in prolongation of survival.

Since then, it has been revealed that hepatocellular carcinoma is a highly vascular tumor, and as a result, targeted therapies mainly targeting vascular endothelial cell growth factor receptor (VEGFR) have been developed, such as Nexavar (chemical name: Sorafenib) and Lenvima (chemical name: Lenvatinib). These therapies have become an alternative treatment for advanced and metastatic hepatocellular carcinoma.

However, since there are few symptoms in the early stages, treatment is begun after the cancer progresses and symptoms appear. Due to this nature of hepatocellular carcinoma, an effective treatment method for the late-stage HCC is needed. There is also a need for a supplementary therapy for the existing therapies or a new mechanism of therapy.

Meanwhile, glypican-3 (GPC3), which is glycosyl-phosphatidylinositol (GPI)-anchored heparan sulfate proteoglycan (HSPG) controlling cell division and growth, belongs to the glypican family. GPC3 consists of a N-terminal subunit and a C-terminal subunit, and is known to be involved in Wnt, IGF, FGF, and TGF-$\beta$2 signaling pathways. GPC3 is an HCC-specific marker, and many anticancer agents targeting GPC3 have been studied.

At present, many pharmaceutical companies are developing monoclonal antibodies (mAb), antibody drug conjugates (ADCs), and chimeric antigen receptor T-cells (CAR-Ts) against GPC3, which are currently in preclinical or clinical stages. However, effective GPC3-targeting anticancer agents for HCC have not yet been developed.

PRIOR ART DOCUMENT

J Korean Med Assoc 2013 November; 56(11): 1001-1011

DISCLOSURE OF INVENTION

Technical Problem

The present inventors have made many efforts to develop a novel therapeutic agent for hepatocellular carcinoma, and as a result, they have developed a therapeutic agent for hepatocellular carcinoma, which exhibits anticancer effects by specifically delivering a drug to desired hepatoma cells, thereby completing the present invention.

Solution to Problem

An object of the present invention is to provide a modified aptamer including a nucleic acid aptamer specifically binding to glypican-3 (GPC3) and an anticancer agent bound to the nucleic acid aptamer.

Another object of the present invention is to provide a pharmaceutical composition for preventing or treating hepatoma, the pharmaceutical composition including the modified aptamer as an active ingredient.

Still another object of the present invention is to provide the nucleic acid aptamer.

Still another object of the present invention is to provide a composition for detecting glypican-3, the composition including the nucleic acid aptamer as an active ingredient.

Still another object of the present invention is to provide a method of detecting glypican-3, the method including, in order to provide information needed for diagnosis or prognosis of hepatoma, detecting a content of glypican-3 in a biological sample derived from a test subject; comparing the result of detecting the content with the result of detecting a content of glypican-3 in a control sample; and associating the subject with diagnosis or prognosis of hepatoma, when a change in the content level in the sample derived from the subject is observed, as compared with the control sample.

Still another object of the present invention is to provide a kit for diagnosing hepatoma, the kit including the composition for detecting glypican-3.

Still another object of the present invention is to provide use of the modified aptamer, the nucleic acid aptamer, the pharmaceutical composition, or the composition for diagnosing, preventing or treating hepatoma.

Advantageous Effects of Invention

A glypican-3-specific modified aptamer of the present invention specifically binds to glypican-3 to be internalized into hepatoma cells, and exhibits anticancer activity by an anticancer agent bound to the aptamer, and therefore has a selective anticancer effect only for GPC3-expressing hepatoma cells without affecting normal hepatocytes.

BRIEF DESCRIPTION OF DRAWINGS

FIG. 1 shows protein binding affinity of GPC3-specific aptamer libraries, wherein NT # represents the number of nucleotides (length), and the lowest two concentrations were excluded from the concentrations of the proteins;

FIG. 2 shows protein binding affinities of 2428-12-10 (40-mer) and 12-12 (35-mer) prepared by truncating a part of the sequence of 2428-12-10, among the GPC3-specific aptamer libraries;

FIG. 3 shows a schematic illustration of gemcitabine-bound 12-10 modified aptamers, wherein chemical substitution was not indicated in the 2D prediction program, and thus indicated by general bases;

FIGS. 4A and 4B shows protein binding affinities of the gemcitabine-bound 12-10 modified aptamers;

FIG. 5 shows anticancer efficacies of the gemcitabine-bound 12-10 modified aptamers;

FIG. 6 shows cell binding of aptamer libraries prepared by truncating 2428-12-10(12-10) at various lengths, among the GPC3-specific aptamer libraries;

FIG. 7 shows cellular internalization of aptamer libraries prepared by truncating 2428-12-10(12-10) at various lengths, among the GPC3-specific aptamer libraries;

FIG. 8 shows a schematic illustration of gemcitabine-bound 12-12 modified aptamers, wherein chemical substitution was not indicated in the 2D prediction program, and thus indicated by general bases;

FIG. 9 shows cell binding of gemcitabine-bound 12-12 modified aptamers, wherein 12-12 represents 12-12 aptamer, and SC represents scrambled 12-12 aptamer;

FIG. 10 shows cellular internalization of a modified aptamer bound with three gemcitabines (12-12 G(3)), wherein 12-12 represents 12-12 aptamer, and SC represents scrambled 12-12 aptamer;

FIG. 11 shows cellular internalization over time of the modified aptamer bound with three gemcitabines (12-12 G(3)), wherein 12-12 represents 12-12 aptamer, and SC represents scrambled 12-12 aptamer;

FIG. 12 shows anticancer efficacy according to concentrations (10 nM to 1 µM) of the modified aptamer bound with three gemcitabines (12-12 G(3)), wherein 12-12 represents 12-12 aptamer, and Gemcitabine represents gemcitabine alone;

FIG. 13 shows anticancer efficacy according to concentrations (31.75 nM to 2 µM) of the modified aptamer bound with three gemcitabines (12-12 G(3)), wherein 12-12 represents 12-12 aptamer, and Gemcitabine represents gemcitabine alone;

FIG. 14 shows protein binding affinity and cell binding according to base substitution positions in the aptamer sequence and targets (Nap-dU, C3 liner, 2-F, 2-O-Me);

FIG. 15 shows selection of chemically optimized aptamer candidates by considering the protein binding affinity and cell binding;

FIG. 16 shows cell binding of chemically optimized aptamer libraries;

FIGS. 17A and 17B show cellular internalization of chemically optimized aptamer libraries (Combi 6 to Combi 10);

FIG. 18 shows protein binding affinity of chemically optimized aptamer libraries bound with gemcitabine;

FIG. 19 shows cell binding of chemically optimized aptamer libraries bound with gemcitabine;

FIG. 20 shows cellular internalization of chemically optimized aptamer libraries (Combi 1 to Combi 3), wherein Control represents untreated, 12-12 represents 12-12 aptamer, and SC represents scrambled 12-12 aptamer;

FIG. 21 shows cellular internalization of chemically optimized aptamer libraries bound with three or five gemcitabines (Combi 4), wherein Control represents untreated, 12-12 represents 12-12 aptamer, and SC represents scrambled 12-12 aptamer;

FIG. 22 shows cellular internalization of chemically optimized aptamer libraries bound with three or five gemcitabines (Combi 5), wherein Control represents untreated, 12-12 represents 12-12 aptamer, and SC represents scrambled 12-12 aptamer;

FIG. 23 shows anticancer efficacy of chemically optimized aptamer libraries bound with three or five gemcitabines (Combi 4 to Combi 5);

Figure 24:
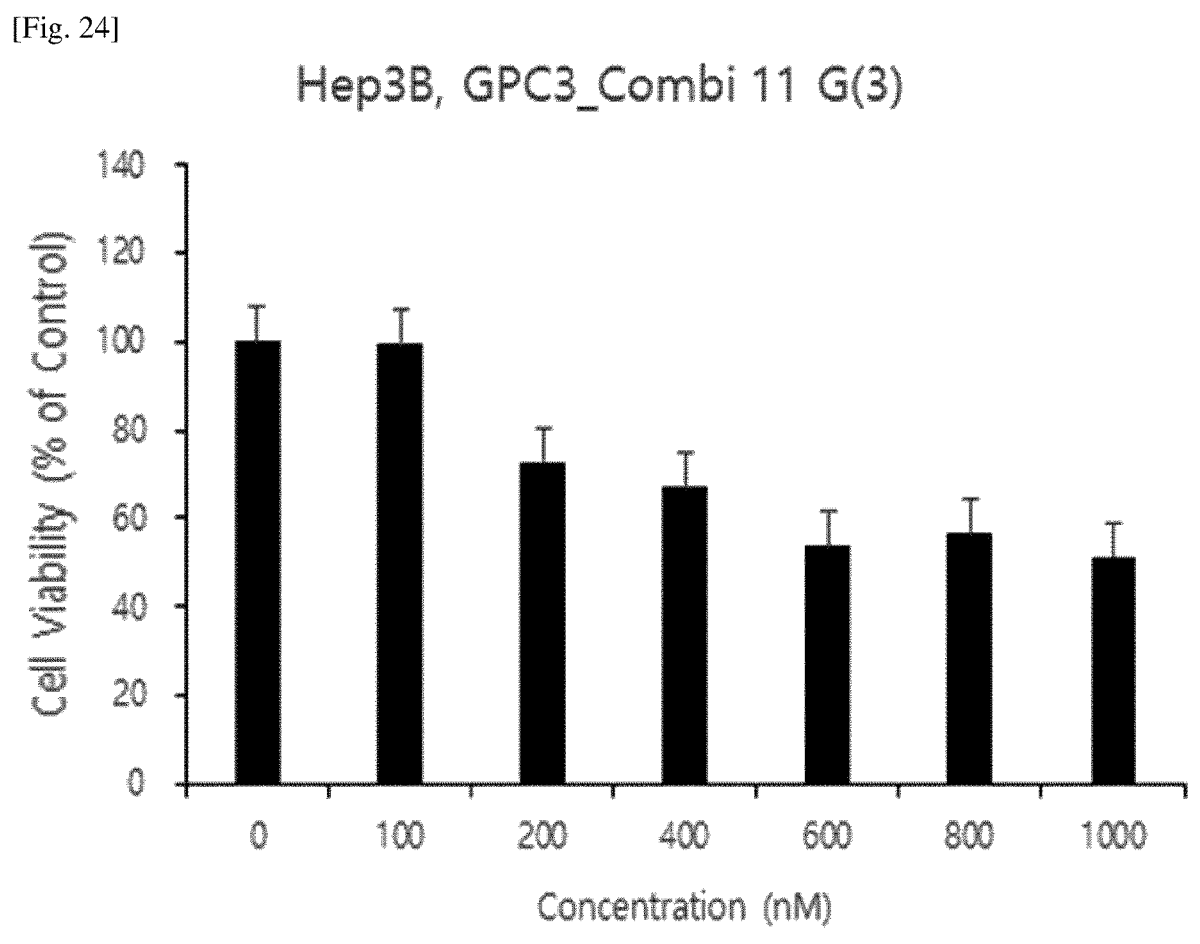

FIG. 24 shows anticancer efficacy of chemically optimized aptamer bound with three gemcitabines (Combi 11 G(3));

FIGS. 25A and 25B show Hep3B cell cycle analysis of chemically optimized aptamer libraries bound with three or five gemcitabines (Combi 4 to Combi 5);

FIGS. 26A and 26B show HepG2 cell cycle analysis of chemically optimized aptamer libraries bound with three or five gemcitabines (Combi 4 to Combi 5);

FIGS. 27A and 27B show A431 cell cycle analysis of chemically optimized aptamer libraries bound with three or five gemcitabines (Combi 4 to Combi 5); and FIG. 28 shows mouse serum stability of chemically optimized aptamer libraries (12-12, combi 5 G(3)).

BEST MODE FOR CARRYING OUT THE INVENTION

The present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

To achieve the above objects, an aspect of the present invention provides a modified aptamer including a nucleic acid aptamer specifically binding to glypican-3 (GPC3) and an anticancer agent bound to the nucleic acid aptamer.

As used herein, the term "glypican-3", which is glycosylphosphatidylinositol (GPI)-anchored heparan sulfate proteoglycan (HSPG) controlling cell division and growth, consists of a N-terminal subunit and a C-terminal subunit, and is known to be involved in Wnt, IGF, FGF, and TGF-β2 signaling pathways.

As used herein, the term "aptamer", or "nucleic acid aptamer", which is a "chemical antibody", refers to a single-stranded nucleic acid molecule having a short length (20 to 80 bases) and having a property of being able to bind to various kinds of target ligands from specific compounds to proteins with high specificity and affinity. The aptamer may be prepared in vitro through systematic evolution of ligands by exponential enrichment (SELEX). The "nucleic acid aptamer" may be included in "aptamer", and may be used interchangeably with "aptamer" or "nucleic acid aptamer"

The aptamer is considered as an oligonucleotide molecule having characteristics similar to an antibody in that it has high affinity and selectivity at nanomolar (nM) to femtomolar (fM) levels for a target protein. Meanwhile, compared to antibodies, aptamers have several advantages as follows: (1) since their chemical synthesis is easy, and they are relatively small and simple molecules, various necessary modifications are easily possible, (2) selectivity and affinity may be maximized through the SELEX process, (3) since they are prepared by chemical synthesis, they have high purity, (4) it is possible to identify the prepared substances through instrument analysis, (5) it is possible to develop aptamers for toxins for which it is difficult to produce antibodies by injecting into animals, (6) since they are stable to heat, long-term storage at room temperature is possible, (7) they hardly cause immune response (immunogenicity) in vivo, and (8) once an aptamer specifically binding to a specific substance is isolated, it may be reproduced with consistency and low cost by an automated oligomer synthesis method, which is economical.

An aptamer selection process generally requires a process of obtaining a single-stranded nucleic acid pool from libraries having $10^{14}$ to $10^{15}$ different sequences, i.e., diversity. To this end, various methods are used, but a method of amplifying only one strand by asymmetric PCR, or a method of attaching biotin to the end of one strand of a double-stranded nucleic acid and selectively selecting only one strand using streptavidin-coated beads is most commonly used.

Thereafter, a selection process of selecting an aptamer having high binding ability by binding the obtained libraries to the target molecule is performed. When the target molecule is a protein, biotinylated protein is usually pulled down using streptavidin beads. After inducing binding of the target protein and the modified nucleic acid libraries, washing is performed using a buffer to remove the modified nucleic acid libraries that do not bind to the target protein.

Likewise, in the case of a plate, after inducing binding of the nucleic acid libraries and the target protein, washing is performed using a buffer to remove nucleic acids that do not bind to the target protein. By these methods, aptamers having affinity for ligands may be obtained. Usually, aptamers with high affinity may be obtained by repeating 5-15 cycles of the selection-amplification process. When the selection process is completed, the amplified nucleic acids are cloned, sequences of individual clones are identified through sequencing, and aptamers are synthesized to measure affinity and binding ability with respect to the target molecule.

As used herein, the term "target molecule" refers to a substance which may be detected by the aptamer of the present invention. Specifically, the target molecule is present in an isolated sample, and may be one or more selected from the group consisting of proteins, peptides, carbohydrates, polysaccharides, glycoproteins, hormones, receptors, antigens, antibodies, viruses, cofactors, drugs, dyes, growth factors, and controlled substances, to which a capturing aptamer may bind, but is not limited thereto. With respect to the objects of the present invention, the target molecule may be glypican-3, a ligand thereof, or a receptor thereof.

With respect to the objects of the present invention, the nucleic acid aptamer specifically binding to glypican-3 may consist of a variant of SEQ ID NO: 1, i.e., a variant of a nucleotide sequence of SEQ ID NO: 1, but is not limited thereto.

In the present invention, SEQ ID NO: 1 does not exclude addition of a meaningless sequence upstream or downstream of the nucleotide sequence of SEQ ID NO: 1, or a naturally occurring mutation therein, or a silent mutation therein. It is obvious that as long as a sequence has an activity identical or corresponding to that of the polynucleotide including the nucleotide sequence of SEQ ID NO: 1, it belongs to SEQ ID NO: 1 of the present invention. For example, SEQ ID NO: 1 of the present invention may be a polynucleotide consisting of the nucleotide sequence of SEQ ID NO: 1 or a nucleotide sequence having 80%, 85%, 90%, 95%, 96%, 97%, 98%, or 99% or more homology or identity thereto. Additionally, it is obvious that any polynucleotide having a nucleotide sequence with deletion, modification, substitution, or addition in part of the sequence may also be included within the scope of SEQ ID NO: 1 of the present disclosure, as long as the nucleotide sequence has the homology or identity described above and exhibits efficacy corresponding to that of the aptamer.

In other words, although described as 'a polynucleotide consisting of a nucleotide sequence of a specific SEQ ID NO' in the present disclosure, it is obvious that any polynucleotide having a nucleotide sequence with deletion, modification, substitution, or addition in part of the sequence may also be used in the present disclosure, as long as the polynucleotide may have an activity identical or corresponding to that of a polynucleotide consisting of the nucleotide sequence of the corresponding SEQ ID NO. For example, it is obvious that any polypeptide may belong to the 'polynucleotide consisting of the nucleotide sequence of SEQ ID NO: 1', as long as it has an activity identical or corresponding to that of the 'polynucleotide consisting of the nucleotide sequence of SEQ ID NO: 1'.

The variant of a specific SEQ ID NO may include a form in which any one or more of the nucleotides constituting the specific SEQ ID NO are chemically or physically modified.

For example, the variant may include modifications due to any one or more substitutions selected from the group consisting of cleavage of one or more nucleotides in the nucleotide sequence of a specific SEQ ID NO; substitution with a naphthyl group at the C5 position of a pyrimidine group of a base structure in one or more nucleotides in the nucleotide sequence of the specific SEQ ID NO; substitution of one or more nucleotides with a linker having no sugar or base; substitution of the —OH group at the C2 position of the sugar structure in one or more nucleotides with one or more of -methoxy, —F (fluorine), or methoxyethyl; substitution with a benzyl group at the C5 position of the pyrimidine group of the base structure in one or more nucleotides.

The variant of SEQ ID NO: 1 may include a form in which any one or more of the nucleotides constituting SEQ ID NO: 1 are chemically or physically modified.

For example, the variant may include modifications due to any one or more substitutions selected from the group consisting of cleavage of one or more nucleotides in the nucleotide sequence of SEQ ID NO: 1; substitution with a naphthyl group at the C5 position of a pyrimidine group of a base structure in one or more nucleotides in the nucleotide sequence of SEQ ID NO: 1; substitution of one or more nucleotides with a linker having no sugar or base; substitution of the —OH group at the C2 position of the sugar structure in one or more nucleotides with one or more of -methoxy, —F (fluorine), or methoxyethyl; substitution with a benzyl group at the C5 position of the pyrimidine group of the base structure in one or more nucleotides.

The naphthyl group may be represented by the following Chemical Formula 1

[Chemical Formula 1]

Nap-dU

The linker may be represented by the following Chemical Formula 2:

[Chemical Formula 2]

The benzyl group may be represented by the following Chemical Formula 3:

[Chemical Formula 3]

Bn-dU

Specifically, the substitution with the naphthyl group at the C5 position of the pyrimidine group of the base structure in one or more nucleotides may be substitution with 5-(N-naphthylmethylcarboxyamide)-2'-deoxyuridine at the C5 position of the pyrimidine group, but is not limited thereto.

Specifically, the "variant of SEQ ID NO: 1" is not limited to the site and number of variation, and may be any one selected from the group consisting of SEQ ID NO: 6, a variant of SEQ ID NO: 6, SEQ ID NOS: 10 to 19, and a variant of thereof, but is not limited thereto. Further, since the glypican-3-specific nucleic acid aptamer may consist of the variant of SEQ ID NO: 1, it may be any one selected from the group consisting of SEQ ID NO: 6, the variant of SEQ ID NO: 6, and SEQ ID NOS: 10 to 19, but is not limited thereto.

Further, in order to enhance serum stability, the glypican-3-specific nucleic acid aptamer or the modified aptamer may be modified at the 5'-end, the 3'-end, or both ends thereof to have enhanced serum stability. The modification may include modification by binding, to the 5'-end, the 3'-end, or both ends thereof, one or more selected from the group consisting of polyethylene glycol (PEG), inverted de-oxy-thymidine(idT), Locked Nucleic Acid (LNA), 2'-methoxy nucleoside, 2'-amino nucleoside, 2'-F-nucleoside, an amine linker, a thiol linker, and cholesterol. Specifically, idT may be bound to the 3'-end of the aptamer, but is not limited thereto.

With respect to the objects of the present invention, the glypican-3-specific nucleic acid aptamer may specifically bind to glypican-3 to induce cellular internalization.

As used herein, the term "modified aptamer" refers to an aptamer including the above-described nucleic acid aptamer and an anticancer agent. With respect to the objects of the present invention, the modified aptamer may be a modified aptamer including a nucleic acid aptamer consisting of the variant of SEQ ID NO: 1; a nucleic acid aptamer consisting of SEQ ID NO: 6; a nucleic acid aptamer consisting of the variant of SEQ ID NO: 6; or a nucleic acid aptamer consisting of any one of SEQ ID NO: 10 to SEQ ID NO: 19 and an anticancer agent, but is not limited thereto. Specifically, the modified aptamer may include any one or more selected from the group consisting of SEQ ID NO: 2 to SEQ ID NO: 5, SEQ ID NO: 7 to SEQ ID NO: 9, and SEQ ID NO: 20 to SEQ ID NO: 25, but is not limited thereto.

As used herein, the term "anticancer agent" may include a prophylactic or therapeutic agent for lung cancer (e.g., non-small cell lung cancer, small cell lung cancer, malignant mesothelioma), mesothelioma, pancreatic cancer (e.g., pancreatic ductal adenocarcinoma, pancreatic endocrine neoplasm), pharynx cancer, laryngeal cancer, esophageal cancer, gastric cancer (e.g., papillary adenocarcinoma, mucinous adenocarcinoma, adenosquamous carcinoma), duodenal cancer, small intestine cancer, large intestine cancer (e.g., colon cancer, rectal cancer, anal cancer, familial colon cancer, hereditary nonpolyposis colorectal cancer, gastrointestinal stromal tumor), breast cancer (e.g., invasive ductal carcinoma, non-invasive ductal carcinoma, inflammatory breast cancer), ovarian cancer (e.g., epithelial ovarian carcinoma, extragonadal germ cell tumor, ovarian germ cell tumor, ovarian low grade malignant tumor), testicular tumor, prostate cancer (e.g., hormone-dependent prostate cancer, hormone-independent prostate cancer), hepatoma (e.g., hepatocellular carcinoma, primary hepatoma, extrahepatic bile duct cancer), thyroid cancer (e.g., medullary thyroid carcinoma), renal cancer (e.g., rental cell carcinoma, transitional cell carcinoma of the renal pelvis and ureter), uterine cancer (e.g., cervical cancer, endometrial carcinoma, sarcoma of uterus), brain tumor (e.g., medulloblastoma, glioma, pineal astrocytoma, pilocytic astrocytoma, diffuse astrocytoma, anaplastic astrocytoma, pituitary adenoma), retinoblastoma, skin cancer (e.g., basal cell carcinoma, malignant melanoma, etc.), sarcoma (e.g., rhabdomyosarcoma, leiomyosarcoma, soft tissue sarcoma), malignant bone tumor, urinary bladder cancer, blood cancer (e.g., multiple myeloma, leukemia, malignant lymphoma, Hodgkin's disease, chronic myeloproliferative disorder), cancers causing peripheral neuropathy as a side effect, such as cancer of unknown primary, etc. Examples of the anticancer agent may include gemcitabine, cytarabine, carboplatin (paraplatin), cisplatin (platinol, platinol-AQ), crizotinib (xalkori), cyclophosphamide (cytoxan, neosar), docetaxel (taxotere), doxorubicin (adriamycin), erlotinib (tarceva), etoposide (vepesid), fluorouracil (5-fluorouracil, 5-FU), imatinib mesylate (Gleevec), irinotecan (camptosar), liposome-encapsulated doxorubicin (doxil), methotrexate (folex, mexate, amethopterin), paclitaxel (taxol, abraxane), sorafinib (nexavar), sunitinib (sutent), topotecan (hycamtin), trabectidin (yondelis), vincristine (Oncovin, vincasar PFS), and vinblastine (velban), etc., but are not limited thereto, and any known anticancer agent may be used without limitation. Specifically, the anticancer agent may include any one or more selected from the group consisting of gemcitabine, cytarabine, carboplatin, cisplatin, crizotinib, cyclophosphamide, docetaxel, doxorubicin, erlotinib, etoposide, fluorouracil, imatinib mesylate, irinotecan, liposome-encapsulated doxorubicin, methotrexate, paclitaxel, sorafinib, sunitinib, topotecan, trabectidin, vincristine, and vinblastine, and more specifically, gemcitabine, but is not limited thereto.

One or more of the anticancer agents may be bound to the nucleic acid aptamer, and specifically, two or more thereof, and more specifically, three or more thereof may be bound to the nucleic acid aptamer, but are not limited thereto.

The anticancer agent may be bound to any one or more of the 5', the 3'-end, or both ends of the nucleic acid aptamer via any one or more chemical bonds of covalent bonds, ionic bonds, metallic bonds, van der Waals bonds, and hydrogen bonds, or may be bound by substitution of one or more bases in the nucleotide sequence of the aptamer, but is not limited thereto.

With respect to the objects of the present invention, the modified aptamer may be bound by substituting one or more bases in the nucleotide sequence of the nucleic acid aptamer with the anticancer agent, for example, by substituting one or more cytosines or guanines in the nucleotide sequence of the nucleic acid aptamer with the anticancer agent.

Specifically, two or more anticancer agents may be consecutively bound at the above-described end of the nucleic acid aptamer or at one base substitution position in the aptamer. When two or more anticancer agents are consecutively bound, the anticancer agents may be bound to each other via any one or more chemical bonds of covalent bonds, ionic bonds, metallic bonds, van der Waals bonds, and hydrogen bonds, but are not limited thereto.

Further, the anticancer agent may be bound by substituting one or more bases, or two or more bases which independently exist in the nucleotide sequence of the nucleic acid aptamer.

When two or more bases which independently exist are substituted, the anticancer agents may be consecutively or inconsecutively substituted, and when the anticancer agents are inconsecutively substituted, no chemical bond between the anticancer agents may occur, but are not limited thereto.

As described, the modified aptamer, in which one or more bases in the nucleotide sequence of the nucleic acid aptamer are substituted with the anticancer agents, may specifically bind to glypican-3 in the same manner as the nucleic acid aptamer, and as compared with the modified aptamer, in which the anticancer agents are bound to the ends of the nucleic acid aptamer, the anticancer agents may stably exist in vivo, and after internalization into glypican-3-expressing hepatoma cells, the aptamer may be de-composed to release the anticancer agent, which exhibits a cancer cell-specific anticancer effect. Accordingly, indiscriminate cell death by the anticancer agent and side effects thereby may be prevented, and selective cancer cell death may be achieved.

In the present invention, the glypican-3-specific nucleic acid aptamer may include any one nucleotide sequence selected from the group consisting of SEQ ID NO: 2 to SEQ ID NO: 25, but is not limited thereto. Specifically, the glypican-3-specific nucleic acid aptamer may include any one nucleotide sequence selected from the group consisting of SEQ ID NO: 6 and SEQ ID NO: 10 to SEQ ID NO: 19, but is not limited thereto.

In the present invention, the modified aptamer may include the nucleic acid aptamer, and may include any one nucleotide sequence selected from the group consisting of SEQ ID NO: 2 to SEQ ID NO: 5, SEQ ID NO: 7 to SEQ ID NO: 9, and SEQ ID NO: 20 to SEQ ID NO: 25, but is not limited thereto.

Another aspect of the present invention provides a method of preparing the modified aptamer of the present invention.

The terms used herein are the same as described above.

The modified aptamer according to the present invention may be prepared by a method known in the art, for example, by a general method of synthesizing oligonucleotides, or a method of reacting a nucleic acid aptamer and an anticancer agent, but is not limited thereto.

Specifically, the method of synthesizing oligonucleotides may be a method of preparing the modified aptamer including the anticancer agent in the aptamer sequence by adding the anticancer agent instead of bases during synthesis of the nucleic acid aptamer, but is not limited thereto.

Specifically, the method of reacting a nucleic acid aptamer and an anticancer agent may include an aptamer preparation step of preparing the nucleic acid aptamer having the aptamer nucleotide sequence specifically binding to glypican-3; and a modified aptamer formation step of forming the modified aptamer by reacting the nucleic acid aptamer with the anticancer agent, wherein the modified aptamer formation step may be, for example, reacting the nucleic acid aptamer with the anticancer agent and an activator dissolved in acetonitrile for several minutes, but is not limited thereto.

Still another aspect of the present invention provides a pharmaceutical composition for preventing or treating hepatoma, the pharmaceutical composition including the modified aptamer of the present invention as an active ingredient.

The terms used herein are the same as described above.

The pharmaceutical composition of the present invention may have "prophylactic" and/or "therapeutic" use for hepatoma. For prophylactic use, the pharmaceutical composition of the present invention is administered to an individual who already has or is suspected of having a disease, disorder, or condition described herein. In other words, the pharmaceutical composition of the present invention may be administered to an individual at risk of developing hepatoma. For therapeutic use, the pharmaceutical composition of the present invention is administered to an individual, such as a patient already suffering from the disorder described herein, in an amount sufficient to treat or at least partially arrest symptoms of the disease, disorder, or condition described herein. The amount effective for this use will depend on the severity and course of the disease, disorder, or condition, prior treatment, the individual's health status and responsiveness to drugs, and the judgment of the physician or veterinarian.

The pharmaceutical composition of the present invention may further include an appropriate carrier, excipient, or diluent commonly used in the preparation of the pharmaceutical composition of the present invention. In this regard, the content of the active ingredient included in the composition may be, but is not particularly limited to, 0.0001% by weight to 10% by weight, preferably 0.001% by weight to 1% by weight, based on the total weight of the composition.

The pharmaceutical composition may have any dosage form selected from the group consisting of tablets, pills, powders, granules, capsules, suspensions, liquids for internal use, emulsions, syrups, sterilized aqueous solutions, non-aqueous solvents, suspensions, emulsions, lyophilized preparations, and suppositories, and may have various oral or parenteral dosage forms. When formulated, it is prepared by using diluents or excipients, such as fillers, extenders, binders, wetting agents, disintegrants, surfactants, etc., which are commonly used. Solid preparations for oral administration include tablets, pills, powders, granules, capsules, etc., and these solid preparations are prepared by mixing one or more compounds with at least one excipient, e.g., starch, calcium carbonate, sucrose or lactose, gelatin, etc. Further, in addition to simple excipients, lubricants, such as magnesium stearate talc, etc., are also used. Liquid preparations for oral administration may include suspensions, liquids for internal use, emulsions, and syrups, and various excipients such as wetting agents, sweeteners, fragrances, and preservatives may be included, in addition to water and liquid paraffin, which are commonly used simple diluents. Preparations for parenteral administration include sterilized aqueous solutions, non-aqueous solvents, suspensions, emulsions, lyophilized preparations, and suppositories. As the non-aqueous solvents and the suspensions, propylene glycol, polyethylene glycol, vegetable oil such as olive oil, and injectable esters such as ethyl oleate may be used. As a base for suppositories, witepsol, macrogol, tween 61, cacao butter, laurin butter, glycerogelatin, etc. may be used.

The composition of the present invention may be administered to an individual in a pharmaceutically effective amount.

The term "pharmaceutically effective amount", as used herein, means an amount which is sufficient to treat diseases at a reasonable benefit/risk ratio applicable to any medical treatment, and an effective dosage level may be determined according to factors including an individual's type and severity, age, sex, the kind of a disease, drug activity, sensitivity to a drug, administration time, administration routes, excretion rate, treatment period, and drugs simultaneously used, and other factors well known in the medical field. The composition of the present invention may be administered as an individual therapeutic agent or in combination with other therapeutic agents, may be administered consecutively or simultaneously with existing therapeutic agents, and may be administered in a single dose or multiple doses. It is important to administer the composition in the minimum amount that enables achievement of the maximum effects without side effects in consideration of all of the above-described factors, and this may be easily determined by those of ordinary skill in the art. The preferred administration dose of the composition of the present invention may vary according to a patient's condition and body weight, the degree of the disease, the type of the drug, administration route and period, and administration may be performed once daily or in a few divided doses. The composition may be administered to any individual without particular limitation, as long as the individual's hepatoma is intended to be prevented or treated. The mode of administration includes any common method in the art without limitation. For example, the composition may be administered by oral, rectal or intravenous, intramuscular, subcutaneous, endometrial, or intracerebroventricular injection.

The pharmaceutical composition of the present invention is administered to an individual who has already developed or is highly likely to develop hepatoma, thereby preventing occurrence of hepatoma or reducing the degree of occurrence.

The glypican-3-specific modified aptamer, which is an active ingredient in the pharmaceutical composition of the present invention, may be included in the pharmaceutical composition at a concentration of 100 nM to 500 nM. At a concentration lower than the above concentration range, the glypican-3 selective anticancer effect on hepatoma cells may not be sufficient. At a concentration higher than the above concentration range, cytotoxicity to epidermal cancer cells may be exhibited.

Still another aspect of the present invention provides a method of preventing or treating hepatoma, the method including administering, to an individual, the composition including the glypican-3-specific aptamer.

The terms used herein are the same as described above.

In the present invention, the term "individual" refers to all animals, except humans, which have already developed or may develop hepatoma. By administering the pharmaceutical composition of the present invention to an individual suspected of having hepatoma, the individual may be efficiently treated.

As used herein, the term "administration" means introducing the pharmaceutical composition of the present invention into an individual suspected of having hepatoma by any suitable method, and the administration may be made through various routes, either an oral or parenteral route, as long as it may reach a target tissue.

The pharmaceutical composition of the present invention may be administered in a pharmaceutically effective amount, and the pharmaceutically effective amount is the same as described above.

The pharmaceutical composition of the present invention may be administered to any individual without particular limitation, as long as the individual's hepatoma is intended to be prevented or treated. For example, non-human animals such as monkeys, dogs, cats, rabbits, guinea pigs, rats, mice, cows, sheep, pigs, goats, etc., birds, fish, etc. may be used, and the pharmaceutical composition may be administered via a parenteral, subcutaneous, intraperitoneal, intrapulmonary, or intranasal route, and for topical treatment, the pharmaceutical composition may be administered by any appropriate method including intralesional administration, if necessary. The preferred dosage of the pharmaceutical composition of the present invention may vary depending on an individual's condition and body weight, the degree of the disease, the type of the drug, administration route and period, but may be appropriately selected by those skilled in the art. For example, it may be administered by oral, rectal or intravenous, intramuscular, subcutaneous, endometrial, or intracerebroventricular injection, but is not limited thereto.

The appropriate total daily usage of the pharmaceutical composition of the present invention may be determined by a physician within the scope of sound medical judgment, and the pharmaceutical composition may be generally administered in an amount of 0.001 mg/kg to 1000 mg/kg, preferably 0.05 mg/kg to 200 mg/kg, more preferably, 0.1 mg/kg to 100 mg/kg once to several times a day.

Still another aspect of the present invention provides a nucleic acid aptamer specifically binding to glypican-3, the nucleic acid aptamer including any one nucleotide sequence selected from the group consisting of SEQ ID NO: 2 to SEQ ID NO: 25.

The terms used herein are the same as described above.

Still another aspect of the present invention provides a composition for detecting glypican-3, the composition including the nucleic acid aptamer of the present invention as an active ingredient.

The composition for detecting glypican-3 of the present invention may include, in addition to the above-described nucleic acid aptamer, a carrier and/or preservative, a stabilizer, etc., which is known in the art, for stable storage and preservation of the nucleic acid aptamer.

Further, a detectable label may be attached to the nucleic acid aptamer. By attaching a detectable label to the aptamer, it is possible to easily observe and measure binding of the aptamer to the target molecule and the degree of the binding. The detectable label may be a moiety which may be detected by a detection method known in the art, and is not particularly limited. The detectable label may be, for example, at least one selected from the group consisting of a chromogenic enzyme (peroxidase, alkaline phosphatase, etc.), a fluorescent substance (FITC, RITC, rhodamine, Texas Red, fluorescein, phycoerythrin, quantum dots), chromophore, cyanine and radioactive isotopes ($^{124}$I, $^{125}$I, $^{111}$In, $^{99}$mTc, $^{32}$P, $^{35}$S, etc.), but is not limited thereto. Specifically, Cy5 may be linked to the 5' end of the aptamer.

The composition for detecting may detect target molecules or target substances including target molecules, in addition to organs, tissues, or cells, and specifically, may detect target substances expressed in association with cancer cells or tumors, and more specifically, may detect target substances including glypican-3 expressed in association with hepatoma, but is not limited thereto.

In other words, the composition for detecting may be for imaging of glypican-3, but is not limited thereto.

Further, the composition for detecting may detect cells by measuring intracellular fluorescence, and in this regard, the cells may be cells expressing glypican-3, and more specifically, cancer cells expressing glypican-3. The cancer cells may be, for example, hepatoma cells, but are not limited thereto.

In other words, the composition for detecting may be for diagnosing hepatoma by imaging of glypican-3, but is not limited thereto.

Still another aspect of the present invention provides a method of detecting glypican-3, the method including, in order to provide information needed for diagnosis or prognosis of hepatoma, detecting a content of glypican-3 in a biological sample derived from a test subject; comparing the result of detecting the content with the result of detecting a content of glypican-3 in a control sample; and associating the subject with diagnosis or prognosis of hepatoma, when a change in the content in the sample derived from the subject is observed, as compared with the control sample.

The terms used herein are the same as described above.

The sample may include cells, blood, body fluid, or tissues isolated from an individual, and may include glypican-3, but is not limited thereto.

The method of providing information needed for glypican-3 detection may be to detect glypican-3 and to provide information needed for the glypican-3 detection by bringing the detection composition including the aptamer of the present invention into contact with a sample, and examining whether a complex of the aptamer and glypican-3 in the sample is formed, but is not limited thereto.

The complex formation of the aptamer and glypican-3 may be identified by a method known in the art, for example, a colorimetric method, an electrochemical method, a fluorometric method, luminometry, a particle counting method, absorbance measurement, a spectrometric method, a Raman spectroscopic method, a surface plasmon resonance method, an interferometric method, visual assessment, a scintillation counting method, or an enzyme-linked aptamer sorbent assay, but is not limited thereto.

Still another aspect of the present invention provides a kit for diagnosing hepatoma, the kit including the composition for detecting glypican-3.

The terms used herein are the same as described above.

Still another object of the present invention is to provide use of a modified aptamer comprising a nucleic acid aptamer specifically binding to glypican-3 (GPC3) and an anticancer agent for diagnosing, preventing or treating hepatoma.

The terms used herein are the same as described above.

Still another object of the present invention is to provide use of a modified aptamer comprising a nucleic acid aptamer specifically binding to glypican-3 (GPC3) and an anticancer agent for detecting glypican-3 (GPC3).

The terms used herein are the same as described above.

Still another object of the present invention is to provide use of a nucleic acid aptamer specifically binding to glypican-3 for diagnosing, preventing or treating hepatoma.

The terms used herein are the same as described above.

Still another object of the present invention is to provide use of a nucleic acid aptamer specifically binding to glypican-3 for detecting glypican-3 (GPC3).

The terms used herein are the same as described above.

Still another object of the present invention is to provide use of a composition comprising the nucleic acid aptamer for diagnosing, preventing or treating hepatoma.

The terms used herein are the same as described above.

Still another object of the present invention is to provide use of a composition comprising the nucleic acid aptamer for detecting glypican-3.

The terms used herein are the same as described above.

MODE FOR THE INVENTION

Hereinafter, the present invention will be described in more detail with reference to Examples. However, it is apparent to those skilled in the art to which the present invention belongs that these Examples are for illustrative purposes only, and the scope of the present invention is not intended to be limited by these Examples.

Example 1. Selection of GPC3-Specific Aptamer 1-1. Analysis of Protein Binding Affinity To select an aptamer which is the most specific to GPC3 from 7 aptamer libraries expected to be specific to GPC3 [2428-12-09, 2428-12-10, 2428-12-11, 2424-30-01, 2424-30-05, 2424-30-06, 2424-30-07, all 40-mer], a binding assay was performed through registered importer (RI) labeling. In detail, to remove RI-labeled and unlabeled oligonucleotide region at the oligonucleotide 3'-end of each candidate aptamer sequence, 0.25 μL of α-32P, 0.25 μL of DNA nucleotidylexotransferase (terminal transferase), 1 μL of 10×NEB buffer (New England Biolabs, USA), 1 μL of CoCl$_2$, 7.5 μL of a template (aptamer sequence) (total 10 μL) were added to a plate, which was then sealed with foil, and then incubated at 37° C. for 30 min (enzyme incubation). After incubation at 70° C. for 10 min (enzyme incubation), each of the incubated samples was diluted with 30 μL of distilled water. The lower part of the Microspin G-50 column was removed and a tube was put thereon. After spinning at 800 rcf for 1 min, the tube was removed. The sample was put in a resin, followed by spinning at room temperature and 800 rcf for 2 min.

The aptamers, from which RI-labeled and unlabeled oligonucleotide ends were removed, were diluted with 100 μL of 1×SB18T$_{0.05}$ to 20,000 cpm. The aptamers were heated at 95° C. for 5 min, and subsequently, cooled at 37° C. for 15 min. 100 nM of protein (GPC3) was subjected to 4.64-fold serial dilution, and each 30 μL of a total of 8 points was added to each well. 200 μL of 1×SB18T$_{0.05}$ was added to the aptamers, of which heating and cooling were completed, and then 30 μL thereof was added to each well for a total volume of 60 μL. 2 μL of the aptamer was dropped as an input control on a nylon filter, followed by incubation at 37° C. for 30 min. During incubation, 30 μL of 1×SB18T$_{0.05}$ was added to a filter plate in advance. After incubation, 5.5 μL of Zorbax resin was added, and allowed to react at 1400 rpm for 1 min. The Zorbax-protein-aptamer was added to the filter plate, suctioned, and then washed with 200 μL of 1×SB18T$_{0.05}$. The nylon filter was exposed, and the filter plate was screened in a phosphorimager for 17 hr overnight. The screen was analyzed, and the binding degree according to each protein concentration was derived (percentage bound value).

As a result, as shown in FIG. 1, it was found that as the protein concentration was higher, more aptamers were bound thereto, and among the candidates, 2428-12-10 had a maximum binding capacity (B$_{max}$) of 0.79 and a dissociation constant (K$_d$) of 1.50 to exhibit the most excellent binding ability.

2428-12-10 aptamer (hereinafter, referred to as 12-10, 40-mer, SEQ ID NO: 1) exhibiting the most excellent binding ability and 12-12 (35-mer) aptamer prepared by truncating a part of the sequence of 2428-12-10 were examined for binding affinity by the following method. In detail, cyanine 5 (Cy5) NHS ester (GE Healthcare, Little Chalfont, UK) was bound to GPC3 to prepare GPC3-Cy5. Cy5 synthesis was performed in the same manner as in the general oligonucleotide synthesis. A minimum amount of water (about 50 μL) was added to the final synthesized powder and re-suspended, and then 100 nM of GPC3-Cy5 was subjected to 4.64-fold serial dilution, and the binding degree according to each protein concentration was obtained.

As a result, as shown in FIG. 2, it was found that as the protein concentration was higher, more aptamers were bound thereto, and K$_d$ values of 12-10 and 12-12 were similar to each other.

1-2. Analysis of Protein Binding Affinity of GPC3-Specific Aptamer and Modified Aptamer A modified aptamer, in which an anticancer agent was bound to 12-10 (40-mer) aptamer, was prepared. The modified aptamer was prepared by using an oligonucleotide synthesis method, and during oligonucleotide synthesis, two bases in the aptamer sequence were substituted with an anticancer agent [gemcitabine, (2',2'-difluoro 2'-deoxycytidine)] to form the modified aptamer. With regard to the gemcitabine-substituted position, the position, which was predicted not to affect the structural formation of the aptamer even when substituted with gemcitabine was selected from nucleotide sequences C and G, and two gemcitabines were substituted at the 3'-end, loop, 5'-end, or pair, respectively, to prepare 12-10 G(2) aptamers (SEQ ID NO: 2, SEQ ID NO: 3, SEQ ID NO: 4, SEQ ID NO: 5) (FIG. 3). The aptamer sequences are shown in Table 1 below.

TABLE 1

| SEQ ID NO: | Name | Sequence |
|---|---|---|
| 1 | 12-10 | GGGAAGnGAAnGCGnnGAAnnAnGnCCC nnCAGnCAnCAC |
| 2 | 12-10 G(2)3' | GGGAAGnGAAnGCGnnGAAnnAnGnCCC nnCAGnCAnCASSA |

TABLE 1-continued

| SEQ ID NO: | Name | Sequence |
|---|---|---|
| 3 | 12-10 G(2)L | GGGAAGnGAAnGCGnnGAAnnAnGnSSC nnCAGnCAnCAC |
| 4 | 12-10 G(2)5' | SSGAAGnGAAnGCGnnGAAnnAnGnCCC nnCAGnCAnCAC |
| 5 | 12-10 G(2)P | GGGAAGnGAAnGCGnnGAAnnAnGnCCC nnCAGnSAnSAC |

In the sequence, the base represented by "n" is a base (BzdU) in which a benzyl group was introduced at the C5 position of a pyrimidine group of deoxyuridine, and is represented by Chemical Formula 3. The base represented by "S" is a base substituted with gemcitabine.

Thereafter, the prepared 12-10 G(2) modified aptamers (SEQ ID NO: 2, SEQ ID NO: 3, SEQ ID NO: 4, and SEQ ID NO: 5) and 12-10 as a control group were analyzed for protein binding affinity according to the method of Example 1-1.

As a result, as shown in FIG. 4, the binding affinity was found to vary depending on the position of gemcitabine. This result suggests that substitution of gemcitabine at the pair or the 5' end affects binding ability to the protein.

1-3. Analysis of Anticancer Efficacy of GPC3-Specific Aptamer and Modified Aptamer To examine whether 100 μM of 12-10 G(2) modified aptamer (SEQ ID NO: 2, SEQ ID NO: 3), an untreated group (12-10) as a control group, and a gemcitabine-treated group which was treated with 200 nM gemcitabine alone which was a two-fold concentration to match the number of gemcitabine exhibit selective anticancer efficacy against hepatocytes, cytotoxicity was analyzed. In detail, Huh-7 cells (ATCC, Rockville, MD, USA) were seeded in a 96-well plate at a density of 1×10$^4$/mL, and cultured using a DMEM (Gibco, Grand Island, NY, USA) medium containing 10% FBS (Gibco, Grand Island, NY, USA) and 1% antibiotics (penicillin/streptomycin) under conditions of 5% CO$_2$ and 37° C. Next day, the aptamer stock (100 μM) was mixed with 5×SB18 buffer to prepare the stock at a concentration of 80 μM, and heated at 95° C. for 5 min, and then cooled at room temperature for 15 min or more. The medium was removed from the cultured cells, and 100 μL of a serum-free medium was added thereto, and cultured under conditions of 37° C. and 5% CO$_2$ for 1 hr. The serum-free medium was removed, and then the cells were washed with 100 μL of 1×PBS. 100 μL of KRPH buffer was added, and cultured under conditions of 37° C. and 5% CO$_2$ for 1 hr. The aptamer was diluted with KRPH buffer to 2-fold of the desired concentration, and added to a 96-well plate at 1× concentration, and cultured under conditions of 37° C. and 5% CO$_2$ for 4 hr. After treatment with the aptamer, the KRPH buffer was removed, and then 100 μL of culture medium was added and cultured under conditions of 37° C. and 5% CO$_2$ for 3 days. 6 days later, 10 μL of a kit solution of CCK-8 (Cell Counting Kit-8) was added to each well, and then cultured under conditions of 37° C. and 5% CO$_2$ for 3 hr. Cell death levels were examined at 450 nM using a microplate reader.

As a result, as shown in FIG. 5, the complexes bound to the 3' end and the loop showed mostly similar cell-killing effects to each other, and exhibited significant anticancer efficacy by gemcitabine.

Example 2. Selection of Length-Optimized GPC3-Specific Aptamer 2-1. Cell Binding Analysis The 12-10 aptamer and 5 aptamer libraries prepared by truncating the 12-10 aptamer at various lengths [12-10 (40-mer), 12-12 (35-mer), 12-11 (29-mer), 12-13 (24-mer), 12-14 (23-mer), 12-15 (18-mer)] were subjected to cell binding analysis. Each aptamer sequence was labeled with Cy5 at the 5' end thereof according to the method of Example 1-1. Huh 7 cells (ATCC, Rockville, MD, USA) were seeded at a density of $2 \times 10^6$/mL in a 100 mm² culture plate, and cultured using a DMEM medium (Gibco, Grand Island, NY, USA) containing 10% FBS (Gibco, Grand Island, NY, USA) and 1% antibiotics (penicillin/streptomycin) under conditions of 5% $CO_2$ and 37° C. 5 µM of the aptamer stock was mixed with 5×SB18 buffer to prepare the aptamer at a concentration of 4 µM, and heated at 95° C. for 5 min, and then cooled at room temperature for 15 min or more. 4 µM of the aptamer was diluted with KRPH buffer (20 mM HEPES, 5 mM $KH_2PO_4$, 1 mM $MgSO_4$, 1 mM $CaCl_2$, 136 mM NaCl, 4.7 mM KCl, pH 7.4) at a concentration of 25 nM. The culture medium was removed from the cultured cells, and 4 mL of phosphate-buffered saline (PBS) was added thereto, followed by washing, and then 4 mL of PBS was removed. 4 mL of cold PBS or warm PBS was added, and cells were scraped using a scraper, and collected in tubes, followed by pipetting. The cells were divided and added to fluorescence-activated cell sorting (FAC) tubes according to the number of samples, followed by centrifugation at 4° C. and 2000 rpm for 4 min. After removing the supernatant, each 500 µL of 25 nM aptamer and control (31-08 (40-mer) aptamer) were added to 15 mL of KRPH buffer, followed by pipetting. The tube was covered with foil to block the light, followed by incubation at 4° C. for 30 min. After incubation, centrifugation was performed at 4° C. and 2000 rpm for 4 min, and the supernatant was removed. 2 mL of cold 1×PBS was added, washed, centrifuged at 4° C. and 2000 rpm for 4 min, and the supernatant was removed. This process was repeated three times. At the third time, the supernatant was removed, and then the resultant was placed in 1 mL to 2 mL of FACs buffer (1% BSA, 1×PBS), and transferred to a FACs tube, and placed on ice. Cy5 was measured at 650 nM to 670 nM.

As a result, as shown in FIG. 6, 12-12 (35-mer) exhibited the most excellent cell binding ability.

2-2. Cellular Internalization Analysis 5 aptamer libraries prepared by truncating the 12-10 aptamer at various lengths [12-12 (35-mer), 12-11 (29-mer), 12-13 (24-mer), 12-14 (23-mer), and 12-15 (18-mer)] were subjected to cellular internalization analysis. In detail, a 6-well plate was prepared, and a round cover glass was placed in the 6-well plate. Huh-7 cells were cultured in the 6-well plate according to the method of Example 1-3. 5 µM of the aptamer stock was mixed with 5×SB18 buffer to prepare the aptamer at a concentration of 4 µM, and heated at 95° C. for 5 min, and then cooled at room temperature for 15 min or more. The next day, the medium was removed from the cultured cells, and a serum-free medium was added thereto, and cultured under conditions of 37° C. and 5% $CO_2$ for 1 hr. The serum-free medium was removed, and then the cells were washed with 2 mL of 1×PBS. KRPH buffer was added, and cultured under conditions of 37° C. and 5% $CO_2$ for 1 hr. 4 µM aptamer was diluted to 25 nM, and then cultured under conditions of 37° C. and 5% $CO_2$ for 1 hr or 4 hr. Washing was repeated three times with 2 mL of 1×PBS. Washing was performed in a shaker at room temperature for 10 min while blocking the light. Thereafter, the cells were fixed by treatment with 4% paraformaldehyde at 4° C. for 10 min. Washing was repeated three times with 2 mL of 1×PBS. A permeabilization solution (0.2% Triton X-100 in 1×PBS) was added, followed by incubation at room temperature for 15 min. Washing was repeated three times with 2 mL of 1×PBS. A blocking solution (3% BSA, 1×PBS) was added, followed by incubation under conditions of 37° C. and 5% $CO_2$ for 20 min. Washing was performed once with 2 mL of 1×PBS. Treatment with a blocking solution containing 150 nM lysotracker was performed, followed by incubation under conditions of 37° C. and 5% $CO_2$ for 1 hr. Washing was repeated three times with 2 mL of 1×PBS, and staining with 4',6-diamidino-2-phenylindole (DAPI) was performed. The cover glass was carefully removed and polished.

As a result, as shown in FIG. 7, 12-12 (35-mer) exhibited the most excellent cellular internalization.

2-3. Cell Binding and Cellular Internalization Analysis of GPC3-Specific Aptamer and Modified Aptamer 12-12 (35-mer) aptamer, which was confirmed to have excellent GPC3-binding ability, cell binding, and cellular internalization, was bound with an anticancer agent according to the method of Example 1-2 to prepare 12-12 G(3), 12-12 G(5), and 12-12 G(7) aptamers (SEQ ID NO: 7, SEQ ID NO: 8, SEQ ID NO: 9), each bound with 3, 5, or 7 gemcitabines by substitution (FIG. 8). Each library was synthesized by attaching idT to the 3' end thereof.

Thereafter, 12-12 G(3), 12-12 G(5), and 12-12 G(7) aptamers and an untreated group as a control group (12-12, in which idT was attached to the 3'-end thereof, SEQ ID NO: 6), 12-12-Cy5, and scrambled 12-12 (Scrambled 35-mer) were subjected to cell binding analysis according to the method of Example 2-1. The aptamer sequences are shown in Table 2 below.

TABLE 2

| SEQ ID NO: | Name | Sequence | 3' |
|---|---|---|---|
| 6 | 12-12 | GnGAAnGCGnnGAAnnAnGnCCC CnnCAGnAnCAC | idT |
| 7 | 12-12 G(3) | GnGAAnGCGnnGAAnnAnGnSSS CnnCAGnAnCAC | idT |
| 8 | 12-12 G(5) | GnGAAnGSGnnGAAnnAnGnSSS AnnCAGnCnCAS | idT |
| 9 | 12-12 G(7) | GnGAAnGSSnnGAAnnAnSnSSS nnCAGnCAnCAS | idT |

In the sequence, the base represented by "n" is a base (BzdU) in which a benzyl group was introduced at the C5 position of a pyrimidine group of deoxyuridine, and is represented by Chemical Formula 3. The base represented by "S" is a base substituted with gemcitabine.

As a result, as shown in FIG. 9, the modified aptamer bound with three gemcitabines showed the most excellent cell binding.

Further, the modified aptamer 12-12 G(3) bound with three gemcitabines, 12-12 aptamer as a control group, and scrambled 12-12 (SC) were subjected to cellular internalization analysis according to the method of Example 2-2.

As a result, as shown in FIG. 10, the modified aptamer 12-12 G(3) bound with three gemcitabines showed the most excellent cellular internalization. As shown in FIG. 11, in the results which were confirmed 1 hr, 2 hr, and 4 hr after the start of internalization, the modified aptamer 12-12 G(3) bound with three gemcitabines also showed the most excellent cellular internalization.

The results of the present Example confirmed that cell binding ability decreases, as the number of gemcitabine increases.

2-4. Analysis of Anticancer Efficacy of GPC3-Specific Aptamer and Modified Aptamer To examine whether the modified aptamer 12-12 G(3) which was confirmed to have excellent protein binding affinity, cell binding, and cellular internalization, an untreated group as a control group, 12-12 alone, and gemcitabine alone exhibit GPC3-selective anticancer efficacy against hepatoma and squamous cell carcinoma cells, cytotoxicity was analyzed. In detail, HepG2, Hep3B, and A431 cells (ATCC, Rockville, MD, USA) were each seeded in a 96-well plate at a density of $1 \times 10^4$/mL and cultured using a DMEM (Gibco, Grand Island, NY, USA) medium containing 10% FBS (Gibco, Grand Island, NY, USA) and 1% antibiotics (penicillin/streptomycin) under conditions of 5% $CO_2$ and 37° C. The next day, the aptamer stock (100 µM) was mixed with 5×SB18 buffer to prepare the stock at a concentration of 80 µM, and heated at 95° C. for 5 min, and then cooled at room temperature for 15 min or more. The medium was removed from the cultured cells, and 100 µL of a serum-free medium was added thereto, and cultured under conditions of 37° C. and 5% $CO_2$ for 1 hr. The serum-free medium was removed, and then the cells were washed with 100 µL of 1×PBS. 100 µL of KRPH buffer was added, and cultured under conditions of 37° C. and 5% $CO_2$ for 1 hr. The aptamer was diluted with KRPH buffer to 2-fold of the desired concentration, and added to a 96-well plate at 1× concentration, and cultured under conditions of 37° C. and 5% $CO_2$ for 4 hr. After treatment with the aptamer, the KRPH buffer was removed, and then 100 µL of culture medium was added and cultured under conditions of 37° C. and 5% $CO_2$ for 6 days. 6 days later, 10 µL of a CCK-8 kit solution was added to each well, and then cultured under conditions of 37° C. and 5% $CO_2$ for 3 hr. Cell death levels were examined at 450 nM using a microplate reader.

As a result, as shown in FIG. 12, 10 nM to 1 µM of the modified aptamer 12-12 G(3) bound with three gemcitabines showed the excellent HepG2-killing effects, as compared with 10 nM to 1 µM of 12-12, or 30 nM to 3 µM of gemcitabine, and showed no cell-killing effects on squamous cell carcinoma cell A431.

Further, as shown in FIG. 13, 31.75 nM to 2 µM of the modified aptamer 12-12 G(3) bound with three gemcitabines showed the excellent HepG2-killing effects, as compared with the same concentrations of 12-12 or gemcitabine, and showed no cell-killing effects on squamous cell carcinoma cell A431.

Example 3. Selection of Chemically Optimized GPC3-Specific Aptamer 3-1. Preparation of Base-Substituted Aptamer Library To chemically optimize 12-12 (35-mer) aptamer which was confirmed to have excellent GPC3-binding affinity, cell binding, and cellular internalization, substitution was introduced into the aptamer sequence. In detail, 12 libraries in which Nap-dU was introduced into the aptamer sequence, 11 libraries in which C3 was introduced, 7 libraries in which 2-F was introduced into only the base G in the sequence, 7 libraries in which 2-F was introduced into only the base C in the sequence, 8 libraries in which 2-F was introduced into only the base A in the sequence, 7 libraries in which 2-O-Me was introduced into only the base G in the sequence, 7 libraries in which 2-O-Me was introduced into only the base C in the sequence, and 8 libraries in which 2-O-Me was introduced into only the base A in the sequence were prepared. Each library was synthesized by attaching Cy5 at the 5' end thereof and idT at the 3'-end thereof.

3-2. Analysis of Protein Binding Affinity of Base-Substituted Aptamer Library

To analyze the protein binding affinity of the aptamer libraries of Example 3-1, libraries into which Nap-dU, 2-F, or 2-O-Me was introduced were subjected to Quantitative Polymerase Chain Reaction (qPCR) binding assay, and libraries into which C3 linker was introduced were subjected to Microscale Thermophoresis (MST) assay. In detail, the protein binding assay using qPCR was performed using a qPCR master mix [based on a final concentration: 1×KOD buffer, 0.2 mM dNTP, 0.2 µM 5', 3' primer, 5 mM $MgCl_2$, 1×SYBR green, 0.025 U/µL KOD polymerase, D.W. (KAPA SYBR FAST qPCR Master Mix, Sigma, Madrid, Spain)]. 5 µL of each aptamer (20 nM) and 95 µL of 1×SB18T$_{0.05}$ were mixed to prepare aptamers at a concentration of 10 fmol ($10^{10}$ copies), and the aptamers were left at 95° C. for 5 min, at 70° C. for 5 min, at 48° C. for 5 min, and then left at 37° C. to perform heating and cooling. 100 nM of GPC3 was subjected to 4.64-fold serial dilution, and each 30 µL of a total of 8 points was added to each well. 200 µL of 1×SB18T$_{0.05}$ was added to the heated and cooled aptamers, and then 30 µL thereof was added to each well such that a total volume of the GPC3 and the aptamer per well was 60 µL. Incubation was performed at 37° C. for 30 min to allow binding between the GPC3 and the aptamer. After incubation, 5.5 µL of 10 mg/mL of TALON bead (Clontech) was added to each well, and reacted at 1400 rpm for 5 min. The reacted TALON bead-GPC3-aptamer mixture was added to a filter plate, and suctioned, and then washed with 200 µL of 1×SB18T$_{0.05}$. Then, SB18T$_{0.05}$ buffer was removed. To remove the remaining buffer in the filter plate, a deep-well plate was placed under the filter plate, followed by centrifugation at 1000 rpm for 1 min. 20 µL of 8 mM HCl was added to a new deep-well plate, and the centrifuged filter plate was placed. 80 µL of 20 mM NaCl was added to the filter plate, and allowed to react at 1000 rpm for 5 min, and then centrifugation was performed at 1000 rpm for 2 min to elute the aptamers. The concentration of the eluted aptamers was adjusted to $10^{10}$ copies, and 10-fold dilution from $10^{10}$ copies to 10 copies was performed using 3.2 mM NaCl, and each 10 µL of the aptamer at each concentration ($10^{10}$ copies, $10^9$ copies, and $10^8$ copies) was added to the second row of the well of the qPCR plate. Each 10 µL of $10^{10}$ copies, $10^9$ copies, and $10^8$ copies of pure aptamer (standard) not bound with each protein were added to the first row of the wells of the qPCR plate. Thereafter, 10 µL of the qPCR mixture was added to all wells such that the total volume in the well was 20 µL, followed by qPCR. The qPCR conditions were as follows: 1 cycle of 96° C. for 45 sec, 55° C. for 10 sec, and 70° C. for 1 hr, and then 40 cycles of 96° C. for 15 sec and 70° C. for 1 min. Then, B$_{max}$ and K$_d$ values were calculated according to the method of Example 1-1.

To perform MST, 24 µL of 5 µM aptamer and 6 µL of 5×SB18 buffer were mixed to prepare 30 µL of 4 µM aptamer, and then heated at 95° C. for 5 min, and then cooled at room temperature for 10 min. The 5' end of the aptamer was labeled with Cy5, and the labeled aptamer and GPC3 were diluted with 1×SB18T$_{0.05}$ buffer to a concentration of 4 nM and 200 nM, respectively. 10 µL of 200 nM GPC3 was dispensed to a new PCR tube at a volume of 20 µL, and 1/2 serial dilution was performed using 1×SB18T$_{0.05}$ buffer. 10

µL of 4 nM aptamer was added to each of the diluted GPC3 to a final volume of 20 µL. 20 µL of GPC3-aptamer mixture was loaded to an MST capillary, and appropriate fluorescence values were determined using a start capillary scan. Then, MST was measured, and $K_d$ and $K_d$ confidence values were derived.

As a result, as shown in FIG. 14, the protein binding affinity of 12-12 (35-mer) aptamer library was identified.

3-3. Selection of Chemically Optimized Aptamer Library

Figure 15:
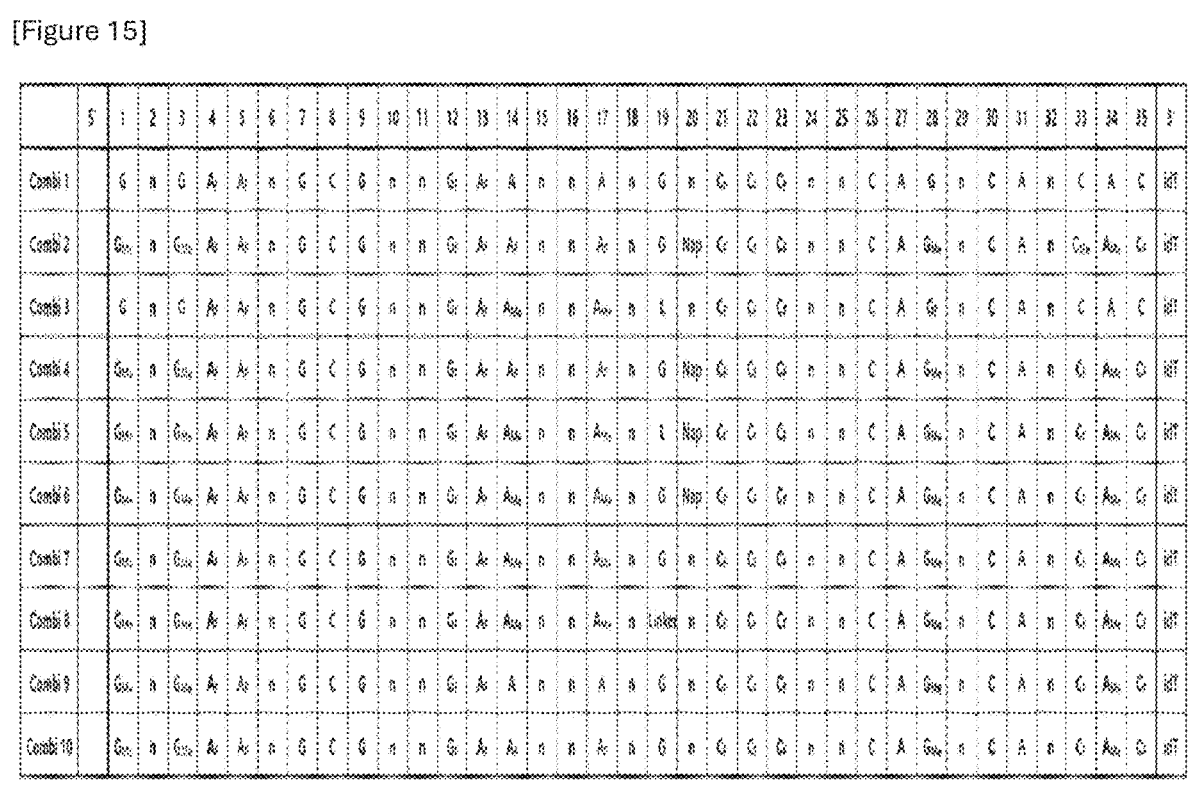

By taking the results of Example 3-2 with the results of analyzing HepG2 cell binding of the aptamer libraries of Example 3-1 according to the method of Example 2-1, and by considering protein binding affinity and cell binding, the base substitution positions in the aptamer sequence and the targets (Nap-dU, C3 linker, 2-F, 2-O-Me) were derived, and 10 aptamer libraries (combi 1 to combi 10, SEQ ID NOS: 10 to 19) expected to exhibit excellent protein binding affinity and cell binding were selected (FIG. 15).

Among the selected aptamers, combi 1 to combi 5 were subjected to cell binding analysis according to the method of Example 2-1 and cellular internalization analysis according to the method of Example 2-2.

As a result, as shown in FIG. 16, HepG2 cell binding of combi 5 was found to be the most similar to that of 12-12, and as shown in FIG. 17A, combi 5 showed the highest Hep3B cellular internalization. Combi 4 also showed the excellent cellular internalization. Further, as shown in FIG. 17B, cellular internalization was also observed in combi 6 to combi 10. Further, combi 6 to combi 10 showed selective cellular internalization in hepatoma specific cells expressing high levels of GPC3 (HepG2, Hep3B), and showed no cellular internalization in A431 cells expressing low levels of GPC3. Among these, combi 8 and combi 9 showed the highest cellular internalization.

Example 4. Selection of Chemically Optimized GPC3-Specific Modified Aptamer 4-1. Analysis of Protein Binding Affinity, Cell Binding, Cellular Internalization, and Anticancer Efficacy According to the method of Example 1-2, an anticancer agent was bound to combi 4, combi 5, and combi 8, which are aptamer libraries confirmed to have excellent protein binding affinity and cellular internalization, to prepare modified aptamers. In detail, three or five gemcitabines were bound to combi 4, combi 5, and combi 8 to prepare modified aptamers. Further, three gemcitabines were bound to an aptamer library (SEQ ID NO: 20) in which some bases in the aptamer sequence were substituted with methoxyethyl (MOE) to prepare a modified aptamer. The aptamer sequences are shown in Table 3 below.

TABLE 3

| SEQ ID NO | Name | Sequence | 3' |
|---|---|---|---|
| 10 | Combi 1 | GnGA$_F$A$_F$nGCGnnG$_F$A$_F$AnnAnGnC$_F$C$_F$C$_F$nnCAGnCAnCAC | idT |
| 11 | Combi 2 | G$_{Me}$nG$_{Me}$A$_F$A$_F$nGCGnnG$_F$AA$_F$nnAmnGYCCC$_F$nnCAG$_{Me}$nCAnC$_{Me}$A$_{Me}$C$_F$ | idT |
| 12 | Combi 3 | GnGA$_F$A$_F$nGCGnnG$_F$A$_F$A$_{Me}$nnA$_{Me}$nWnCCC$_F$nnCAG$_F$nCAnCAC | idT |
| 13 | Combi 4 | G$_{Me}$nG$_{Me}$A$_F$A$_F$nGCGnnG$_F$A$_F$A$_F$nnA$_F$nGYC$_F$C$_F$C$_F$nnCAG$_{Me}$nCAnCAMC$_F$ | idT |

22

TABLE 3-continued

| SEQ ID NO | Name | Sequence | 3' |
|---|---|---|---|
| 14 | Combi 5 | G$_{Me}$nG$_{Me}$A$_F$A$_F$nGCGnnG$_F$A$_F$A$_{Me}$nnA$_{Me}$nWYC$_F$C$_F$C$_F$nnCAG$_{Me}$nCAnC$_F$A$_{Me}$C$_F$ | idT |
| 15 | Combi 6 | G$_{Me}$nG$_{Me}$A$_F$A$_F$nGCGnnG$_F$A$_F$A$_{Me}$nnA$_{Me}$nGYC$_F$C$_F$C$_F$nnCAG$_{Me}$nCAnC$_F$A$_{Me}$C$_F$ | idT |
| 16 | Combi 7 | G$_{Me}$nG$_{Me}$A$_F$AmnGCGnnG$_F$A$_F$A$_{Me}$nnA$_{Me}$nGnCC$_F$C$_F$nnCAG$_{Me}$nCAnCA$_{Me}$C$_F$ | idT |
| 17 | Combi 8 | G$_{Me}$nG$_{Me}$A$_F$A$_F$nGCGnnG$_F$A$_F$A$_{Me}$nnA$_{Me}$nWnC$_F$C$_F$C$_F$nnCAG$_{Me}$nCAnC$_F$A$_{Me}$C$_F$ | idT |
| 18 | Combi 9 | G$_{Me}$nG$_{Me}$A$_F$A$_F$nGCGnnG,A$_F$AnnAnGnC$_F$C$_F$C$_F$nnCAG$_{Me}$nCAnCrAyCr | idT |
| 19 | Combi 10 | G$_{Me}$nG$_{Me}$A$_F$A$_F$nGCGnnG$_F$A$_F$A$_F$nnA$_F$nGnC$_F$C$_F$C$_F$nnCAG$_{Me}$nCAnC$_F$AMCE | idT |
| 20 | Combi 11 G(3) | G$_{moe}$nG$_{moe}$A$_F$A$_F$nGCGnnG$_F$A$_F$A$_{moe}$nnA$_{moe}$nWYSSSnnCAG$_{moe}$nCAnC$_F$A$_{moe}$C$_F$ | idT |
| 21 | Combi 4 G(3) | G$_{Me}$nG$_{Me}$A$_F$A$_F$nGCGnnG$_F$A$_F$A$_F$nnA$_F$nGYSSSnnCAGMnCAnC$_F$AMC$_F$ | idT |
| 22 | Combi 5 G(3) | G$_{Me}$nG$_{Me}$A$_F$A$_F$nGCGnnG$_F$A$_F$A$_{Me}$nnA$_{Me}$nWYSSSnnCAG$_{Me}$nCAnC$_F$A$_{Me}$C$_F$ | idT |
| 23 | Combi 8 G(3) | G$_{Me}$nG$_{Me}$A$_F$A$_F$nGCGnnG$_F$A$_F$A$_{Me}$nnA$_{Me}$nWnSSSnnCAG$_{Me}$nCAnC$_F$A$_{Me}$C$_F$ | idT |
| 24 | Combi 4 G(5) | G$_{Me}$nG$_{Me}$A$_F$A$_F$nGCGnnG$_F$A$_F$A$_F$nnA$_F$nGYSSSnnCAG$_{Me}$nCAnSA$_{Me}$S | idT |
| 25 | Combi 5 G(5) | G$_{Me}$nG$_{Me}$A$_F$A$_F$nGCGnnG$_F$A$_F$A$_{Me}$nnA$_{Me}$nWYSSSnnCAG$_{Me}$nCAnSA$_{Me}$S | idT |

In the sequence, the base represented by "$_{Me}$" is a base (2-O-Me, 2-O-Methoxy-DNA) in which a -Me (methoxy) group was introduced at the C2 position. The base represented by "$_F$" is a base (2-F, 2-Fluorine-DNA) in which a —F (fluorine) group was introduced at the C2 position. The base represented by "$_{moe}$" is a base (2-moe, 2-Methoxyethyl-DNA) in which a -moe (methoxyethyl) group was introduced at the C2 position. The base represented by "Y" is a base (Nap-dU) in which 5-(N-naphthylmethylcarboxy-amide)-2'-deoxyuridine was introduced at the C5 position of a pyrimidine group, and is represented by Chemical Formula 1. The base represented by "W" is a base (C3 linker-DNA) in which a linker (C3 linker) was introduced at the C3 position, and is represented by Chemical Formula 2. The base represented by "n" is a base (BzdU) in which a benzyl group was introduced at the C5 position of a pyrimidine group of deoxyuridine, and is represented by Chemical Formula 3. The base represented by "S" is a base substituted with gemcitabine.

The prepared modified aptamers were subjected to protein binding analysis using MST according to the method of Example 3-2, cell binding analysis according to the method of Example 2-1, and cellular internalization analysis in HepG2 and A431 cells according to the method of Example 2-2.

As a result, as shown in FIG. 18, when three gemcitabines were bound to combi 4 and combi 5, their Kd values were similar to that of 12-12 aptamer, but when five gemcitabines were bound thereto, low binding abilities were observed.

As in FIG. 19, combi 4 and combi 5 bound with three gemcitabines (Combi 4 Gem(3), Combi 5 Gem(3)) showed excellent cell binding ability, as compared with combi 4 and combi 5 bound with five gemcitabines (Combi 4 Gem(5), Combi 5 Gem(5)). When cell binding ability was compared between combi 4 and combi 5, combi 5 showed excellent cell binding ability, like the cell binding ability when no gemcitabine was bound. In FIGS. 20 to 22, combi 4 and combi 5 bound with three gemcitabines (Combi 4 Gem(3), Combi 5 Gem(3)) showed excellent cellular internalization.

To analyze whether combi 4 and combi 5 bound with three or five gemcitabines and combi 11 bound with three gemcitabines exhibit GPC3 selective cell-killing effects against hepatoma cells and squamous cell carcinoma cells, cell-killing effects were analyzed according to the method of Example 1-3.

As a result, as in FIG. 23, combi 4 and combi 5 bound with three or five gemcitabines (Combi 4_G(3), Combi 5_G(3), Combi 4_G(5), Combi 5_G(5)) showed no cell-killing effect up to 500 nM against A431 squamous cell carcinoma cells, but showed the cell-killing effect from 100 nM against GPC3-expressing hepatoma cells. It was confirmed that the number of gemcitabine bound to the aptamer increases, the cell-killing effect became strong.

Further, as shown in FIG. 24, it was confirmed that combi 11 bound with three gemcitabines showed the cell-killing effect from 200 nM against hepatoma cells.

4-2. Cell Cycle Analysis

To analyze the effects of combi 4 and combi 5 bound with three or five gemcitabines on the cell cycle of hepatoma cells, cell cycle analysis was performed. In detail, Hep3B, HepG2, and A431 cells were seeded in a 6-well plate at a density of $1 \times 10^6$/ml, and cultured using a DMEM medium containing 10% FBS and 1% antibiotics (penicillin/streptomycin) under conditions of 5% $CO_2$ and 37° C., respectively. Next day, 100 μM of the modified aptamer stock was mixed with 5×SB18 buffer to prepare the aptamer at a concentration of 80 μM, and heated at 95° C. for 5 min, and then cooled at room temperature for 15 min or more. The medium was removed from the cultured cells, and replaced by a serum-free medium, and cultured under conditions of 37° C. and 5% $CO_2$ for 1 hr. The serum-free medium was removed, and then the cells were washed with 2 ml of 1×PBS. 2 ml of KRPH buffer was added, and cultured under conditions of 37° C. and 5% $CO_2$ for 1 hr. The aptamer was added, and cultured under conditions of 37° C. and 5% $CO_2$ for 4 hr. The KRPH buffer was removed, and 2 ml of 1×PBS was added thereto to perform washing, and then PBS was removed. 2 ml of 1×PBS was added, and cells were scraped using a scraper, and collected in FACs tubes, followed by centrifugation at 4° C. and 2000 rpm for 4 minutes. 1/500-fold diluted RNAase A and propidium iodide diluted with PBS at a concentration of 50 μg/ml were added to the FACs tubes at a volume of 500 μL, followed by pipetting. Incubation was performed at room temperature for 30 min while blocking the light, and then cell cycle was measured.

As a result, as shown in FIGS. 25 to 27, combi 4 and combi 5 bound with three or five gemcitabines (Combi 4_G(3), Combi 5_G(3), Combi 4_G(5), Combi 5_G(5)) arrested hepatoma cells at the G1/S phase of the cell cycle, but showed no cell cycle arrest in squamous cell carcinoma cells. These results showed that the effect of the cell cycle arrest was increased according to the increase in the number of gemcitabine, and no cell cycle arrest was observed in other cancer cells expressing no GPC3 when treated with gemcitabine alone as the comparative group, indicating selectivity for GPC3-expressing cells.

4-3. Serum Stability Analysis

To examine whether 12-12, combi 5 aptamer, combi 4 and combi 5 modified aptamers bound with three or five gemcitabines are stable in the human serum, serum stability was analyzed. In detail, 10 μL of 10 μL modified aptamer was added to 100% human serum, followed by incubation at 37° C. for 0 hr, 1 hr, 3 hr, 6 hr, 12 hr, and 24 hr. After incubation, 5 μL of 10 μL control aptamer was added, and distilled water was added to a volume of 250 μL. 250 μL of phenol:chloroform:isoamyl alcohol (25:24:1) was added in the equal volume, followed by stirring. Each sample was centrifuged at 16000×g for 10 min. The supernatant was transferred to a new tube, and completely dried. The resultant was diluted with 5× sample buffer and distilled water, and boiled at 95° C. for 5 min, and cooled. The sample was separated by urea PAGE (Polyacrylamide gel Electrophoresis) at 220 V for 25 min, and then stained with SYBR gold and examined using a Gel Doc™ EZ system.

As a result, as shown in FIG. 28, 12-12 aptamer maintained a half-life of 6 hr in the human serum, whereas chemically optimized Combi 5 G(3) had a half-life of about 64 hr to show increased stability, indicating about 10 times or more improvement, as compared with 12-12 aptamer before optimization.

These results of Examples confirmed the selective anticancer effect according to the presence or absence of GPC3 and the gemcitabine number-dependent cell-killing effect.

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds are therefore intended to be embraced by the claims.

The invention claimed is:

1. A modified aptamer comprising a nucleic acid aptamer specifically binding to glypican-3 (GPC3) and an anticancer agent, wherein the nucleic acid aptamer consists of any one selected from the group consisting of SEQ ID NO: 6 to SEQ ID NO: 11 and SEQ ID NO: 13 to SEQ ID NO: 25.

2. The modified aptamer of claim 1, wherein one or more anticancer agents are bound to the nucleic acid aptamer.

3. The modified aptamer of claim 2, wherein the anticancer agents are bound by substituting any one or more bases in the nucleotide sequence of the nucleic acid aptamer.

4. The modified aptamer of claim 3, wherein the base is cytosine or guanine.

5. The modified aptamer of claim 2, wherein the anticancer agent is any one or more selected from the group consisting of gemcitabine, cytarabine, carboplatin, cisplatin, crizotinib, cyclophosphamide, docetaxel, doxorubicin, erlotinib, etoposide, 5-fluorouracil (5-FU), imatinib mesylate, irinotecan, liposome-encapsulated doxorubicin, methotrexate, paclitaxel, sorafinib, sunitinib, topotecan, trabectidin, vincristine, and vinblastine.

6. The modified aptamer of claim 5, wherein the anticancer agent is gemcitabine.

7. A pharmaceutical composition for preventing or treating hepatoma, the pharmaceutical composition comprising the modified aptamer of claim 1 as an active ingredient.

8. A nucleic acid aptamer specifically binding to glypican-3, the nucleic acid aptamer consisting of any one nucleotide sequence selected from the group consisting of SEQ ID NO: 6 to SEQ ID NO: 11 and SEQ ID NO: 13 to SEQ ID NO: 25.

9. A composition for detecting glypican-3, the composition comprising the nucleic acid aptamer of claim 8 as an active ingredient, wherein the nucleic acid aptamer is conjugated to a detectable label.

10. A method of detecting glypican-3, the method comprising, in order to provide information needed for diagnosis or prognosis of hepatoma:

detecting a content of glypican-3 in a biological sample derived from a test subject using the composition for detecting of claim 9;

comparing the result of detecting the content with the result of detecting a content of glypican-3 in a control sample; and associating the subject with diagnosis or prognosis of hepatoma, when a change in the content in the sample derived from the subject is observed, as compared with the control sample.

11. A kit for diagnosing hepatoma, the kit comprising (a) the composition for detecting of claim 9, (b) one or more of a buffer, a control sample, and instructions for use.

\*   \*   \*   \*   \*